US007977464B2

(12) United States Patent
Athwal et al.

(10) Patent No.: US 7,977,464 B2

(45) **Date of Patent: *Jul. 12, 2011**

(54) ANTIBODY MOLECULES SPECIFIC TO HUMAN TUMOUR NECROSIS FACTOR ALPHA

(75) Inventors: Diljeet Singh Athwal, London (GB); Derek Thomas Brown, Beenham (GB); Andrew Neil Charles Weir, Reading (GB); Andrew George Popplewell, Staines (GB); Andrew Paul Chapman, Hampton (GB); David John King, Belmont (GB)

(73) Assignee: UCB Pharma S.A., Brussels (BE)

( * ) Notice: Subject to any disclaimer, the term of this patent is extended or adjusted under 35 U.S.C. 154(b) by 252 days.

This patent is subject to a terminal disclaimer.

(21) Appl. No.: 12/141,667

(22) Filed: Jun. 18, 2008

(65) Prior Publication Data

US 2008/0269465 A1 Oct. 30, 2008

Related U.S. Application Data

(63) Continuation of application No. 11/374,231, filed on Mar. 13, 2006, now Pat. No. 7,402,662, which is a continuation of application No. 09/949,559, filed on Sep. 10, 2001, now Pat. No. 7,186,820, which is a continuation of application No. 09/875,221, filed on Jun. 6, 2001, now Pat. No. 7,012,135.

(30) Foreign Application Priority Data

Jun. 6, 2000 (GB) .................................. 0013810.7

(51) Int. Cl.

| | |
|---|---|
| ***C12P 21/08*** | (2006.01) |
| ***C07K 16/00*** | (2006.01) |
| *A61K 39/395* | (2006.01) |
| *C12P 21/04* | (2006.01) |
| *C07H 21/04* | (2006.01) |

(52) U.S. Cl. ............ 530/388.23; 530/387.3; 530/388.1; 424/133.1; 424/141.1; 424/145.1; 424/179.1

(58) Field of Classification Search ........................ None
See application file for complete search history.

(56) References Cited

U.S. PATENT DOCUMENTS

| | | | |
|---|---|---|---|
| 5,919,452 | A | 7/1999 | Le et al. |
| 6,350,860 | B1 | 2/2002 | Buyse et al. |
| 7,012,135 | B2 | 3/2006 | Athwal et al. |

FOREIGN PATENT DOCUMENTS

| | | | |
|---|---|---|---|
| EP | 0 239 400 A2 | | 9/1987 |
| EP | 0 392 745 A2 | | 10/1990 |
| GB | 2 297 145 A | | 7/1996 |
| WO | WO 86/01533 | | 3/1986 |
| WO | WO 89/00195 | | 1/1989 |
| WO | WO 89/01476 | | 2/1989 |
| WO | WO 90/07861 | | 7/1990 |
| WO | WO 91/09967 | | 7/1991 |
| WO | WO 92/11383 | | 7/1992 |
| WO | WO 92/22583 | | 12/1992 |
| WO | WO 93/06231 | | 4/1993 |
| WO | WO 96/33204 | | 10/1996 |
| WO | WO 97/29131 | | 8/1997 |
| WO | WO 98/20734 | | 5/1998 |
| WO | WO 98/25971 | | 6/1998 |
| WO | WO 99/09055 | | 2/1999 |
| WO | WO 99/15549 | | 4/1999 |
| WO | WO 99/45964 | | 9/1999 |
| WO | WO 9964460 A1 | * | 12/1999 |

OTHER PUBLICATIONS

Adorini, L. and Sinigaglia, F., "Pathogenesis and immunotherapy of autoimmune diseases," *Trends in Immunology Today*, 18(5):209-211, (1997).

Arnett, F.C., et al., "The American Rheumatism Association 1987 Revised Criteria for the Classification of Rheumatoid Arthritis," *Arthritis and Rheumatism*, 31(3):315-324, (Mar. 1988).

Ausubel (Ed.), Current Protocols in Molecular Biology, Wiley, NY (1999).

Beutler, et al., "Shock and tissue injury induced by recombinant human cachetin," *Science*, 234:470-474, (1985).

Bodmer, M, et al., "Preclinical review of anti-tumor necrosis factor monoclonal antibodies," *Critical Care Medicine*, 21(10):S441-S446, (1993).

Boers, M., et al., "World Health Organization and International League of Associations for Rheumatology Core Endpoints for Symptom Modifying Antirheumatic Drugs in Rheumatoid Arthritis Clinical Trials," *The Journal of Rheumatology*, (Supplement 41), 21:86-89, (1994).

Chapman, A.P., "Therapeutic antibody fragments with prolonged in vivo half-lives," *Nature Biotechnology*, 17:780-783, (Aug. 1999).

Crameri, A., et al., "DNA shuffling of a family of genes from diverse species accelerates directed evolution," *Nature*, 391(6664):288-291, (Jan. 1988).

Elliott, M.J., et al., "Randomised double-blind comparison of chimeric monoclonal antibody to tumour necrosis factor α (cA2) versus placebo in rheumatoid arthritis," *The Lancet*, 344:1105-1110, (Oct. 22, 1994).

Feldman, M., et al., "Anti-TNFα Therapy Is Useful in rheumatoid Arthritis and Crohn's Disease: Analysis of the Mechanism of Action Predicts Utility in Other Diseases," *Transplantation Proceedings*, 30:4126-4127, (1998).

Feldmann, M., et al., "Anti-Tumor Necrosis Factor-α Therapy of Rheumatoid Arthritis," *Advances in Immunology*, 64:283-350, (1997).

Felson, D.T., "American College of Rheumatology Preliminary Definition of Improvement in Rheumatoid Arthritis," *Arthritis and Rheumatism*, 38(6):727-735, (Jun. 1995).

Fendly, B.M., et al., "Murine Monoclonal Antibodies Defining Neutralizing Epitopes on Tumor Necrosis Factor," *Hybridoma*, 6(4):359-370, (1987).

(Continued)

*Primary Examiner* — David J. Blanchard

(74) *Attorney, Agent, or Firm* — Cozen O'Connor

(57) ABSTRACT

There is disclosed antibody molecules containing at least one CDR derived from a mouse monoclonal antibody having specificity for human TNFα. There is also disclosed a CDR grafted antibody wherein at least one of the CDRs is a hybrid CDR. Further disclosed are DNA sequences encoding the chains of the antibody molecules, vectors, transformed host cells and uses of the antibody molecules in the treatment of diseases mediated by TNFα.

22 Claims, 27 Drawing Sheets

OTHER PUBLICATIONS

Flanagan, J.G. and Rabbitts, T.H., "Arrangement of human immunoglobulin heavy chain constant region genes implies evolutionary duplication of a segment containing γ, ϵ and α genes," *Nature*, 300(5894):709-713, (Dec. 1982).

Genebank Accession No. J00241, version J00241.1 Gl:185938, "Human Ig germline kappa-L chain, C region (inv3 allele)," accessed by PTO on Apr. 6, 2002, (Jan. 5, 1995).

Hieter, P.A., et al., "Cloned Human and Mouse Kappa Immunoglobulin Constant and J Region Genes Conserve Homology in Functional Segments," *Cell*, 22(Part 1):197-207, (Nov. 1980).

Keffer, J., et al., "Transgenic mice expressing human tumour necrosis factor: a predictive genetic model of arthritis," *The EMBO Journal*, 10(13):4025-4031, (1991).

Kirschenbaum, L., et al., "Antibodies to TNF-α: Too little, too late?," *Critical Care Medicine*, 26(10):1625-1626, (1998).

Low, N.M., et al., "Mimicking Somatic Hypermutation: Affinity Maturation of Antibodies Displayed on Bacteriophage Using a Bacterial Mutator Strain," *J. Mol. Biol.*, 260:359-368, (1996).

Maini, R.N., et al., "Clinical Response of Rheumatoid Arthritis (RA) to Anti-TNFα (cA2) Monoclonal Antibody (mab) is Related to Administered Dose and Persistence of Circulating Antibody," *Arthritis Rheum.*, 38(9) (Supplement):S186, (1995).

Maini, R., et al., "Infliximab (chimeric anti-tumour necrosis factor α monoclonal antibody) versus placebo in rheumatoid arthritis patients receiving concomitant methotrexate: a randomised phase III trial," *The Lancet*, 354:1932-1939, (Dec. 4, 1999).

Marks, J.D., et al., "By-Passing Immunization: Building High Affinity Human Antibodies by Chain Shuffling," Bio/Technology, 10:779-783, (Jul. 1992).

McKown, K.M., et al., "Lack of Efficacy of Oral Bovine Type II Collagen Added to Existing Therapy in Rheumatoid Arthritis," *Cancer Research*, 60:3088-3095, (Jun. 2000).

Meager, A., et al., "Preparation and Characterization of Monoclonal Antibodies Directed Against Antigenic Determinants of Recombinant Human Tumour Necrosis Factor (rTNF)," *Hybridoma*, 6(3):305-311, (1987).

Monaco-Malbet, S., et al., "Mutual Conformational Adaptations in Antigen and Antibody upon Complex Formation between an Fab and HIV-1 Capsid Protein p24," *Structure*, 8:1069-1077, (Oct. 2000).

Moreland, L.W., et al., "Etanercept Therapy in Rheumatoid Arthritis: A Randomized, Controlled Trial," *Ann Intern Med.*, 130:478-486, (1999).

Patten, P.A., et al., "Applications of DNA shuffling to pharmaceuticals and vaccines," *Current Opinion in Biotechnology*, 87:724-733, (1997).

Paul, W.E., "Structure and Function of Immunoglobulins," *Fundamental Immunology*, 3rd ed., pp. 292-295, (1993).

Prevoo, M.L.L., "Modified Disease Activity Scores That Include Twenty-Eight-Joint Counts," *Arthritis and Rheumatism*, 38(1):44-48, (Jan. 1995).

Rankin, E.C.C., et al., "The Therapeutic Effects of an Engineered Human Anti-Tumour Necrosis Factor Alpha Antibody (CDP571) in Rheumatoid Arthritis," *British Journal of Rheumatology*, 34:334-342, (1995).

Riechmann, L., et al., "Reshaping human antibodies for therapy," *Nature*, 332:323-327, (Mar. 1988).

Rudikoff, S., et al., "Single amino acid substitution altering antigen-binding specificity," *Proc. Natl. Acad. Sci. USA*, 79:1979-1983, (Mar. 1982).

Scott, D.L., et al., "Disease activity in rheumatoid arthritis: preliminary report of the Consensus Study Group of the European Workshop for Rheumatology Research," *Clinical and Experimental Rheumatology*, 10:521-525, (1992).

Shimamoto, Y., et al., "Monoclonal antibodies against human recombinant tumor necrosis factor: prevention of endotoxic shock," *Immunology Letters*, 17:311-318, (1988).

Stephens, S., et al., "Comprehensive pharmacokinetics of a humanized antibody and analysis of residual anti-idiotypic responses," *Immunology*, 85:668-674, (1995).

Thompson, J., et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," *J. Mol. Biol.*, 256:77-88, (1996).

Vaughan, T., et al., "Human antibodies by design," *Nature Biotechnology*, 16:535-539, (Jun. 1998).

Verhoeyen, M., et al, "Reshaping Human Antibodies: Grafting an Antilysozyme Activity," *Science*, 239:1534-1536, (Mar. 25, 1988).

Waltenberger, J., et al., "Different Signal Transduction Properties of KDR and Flt1, Two Receptors for Vascular Endothelial Growth Factor," *J. Biol. Chem.*, 269(43):26988-26995, (Oct. 1994).

Wherry, J.C., "Tumor necrosis factor and the therapeutic potential of anti-tumor necrosis factor antibodies," *Critical Care Medicine*, 21(10):S436-S440, (Oct. 1993).

Williams, R.O., et al., "Anti-tumor necrosis factor ameliorates joint disease in murine collagen-induced arthritis," Proc. Natl. Acad. Sci. USA, 89:9784-9788, (Oct. 1992).

Wu, T.T. and Kabat, E.A., "An Analysis of the Sequences of the Variable Regions of Bence Jones Proteins and Myeloma Light Chains and Their Implications for Antibody Complementarity," *J. Exp. Med.*, 132:211-250, (1970).

Yang, W.P., et al., "CDR Walking Mutagenesis for the Affinity Maturation of a Potent Human Anti-HIV-1 Antibody into the Picomolar Range," *J. Mol. Biol.*, 254:392-403, (1995).

Winger, G and Harris, WJ, "Humanized antibodies" Trends Pharmacol Sci., vol. 14 No. 5, pp. 139-143, 1993.

Humphreys DP, et al., "Formation of dimeric Fabs in *Escherichia coli*: effect of hinge size and isotype, presence of interchain disulphide bond, Fab' expression levels, tail piece sequence and growth conditions" Journal of Immunolological Methods, vol. 209, pp. 193-202, 1997.

Humphreys DP, et al., "F(ab')2 molecules made from *Escherichia coli* produced Fab' with hinge sequences conferring increased serum survival in an animal model" Journal of Immunolological Methods, vol. 217, pp. 1-10, 1998.

Milton, Harris J., "Laboratory synthesis of polyethylene glycol derivatives" J. Macromol. Sceince-Rev. Macromol. Chem. Phys., vol. C25, vol. 3, pp. 325-378, 1985.

Mattson, G "A practical approach to crosslinking", Molecular Biology Reports, vol. 17, No. 3, pp. 167-1783, 1993.

Schreiber, S., et al., CDP870 Crohn's Disease study group, "A randomized, placebo-controlled trial of Certolizumab pegol (CDP870) for treatment of Crohn's disease" Gastroenterology, vol. 129, pp. 807-818, 2005—Erratum in: Gastroenterology, vol. 129 No. 5, p. 180 2005.

Lund, J., et al., "Expression and characterization of truncated forms of humanized L243 IgG1. Architectural features can influence synthesis of its oligosaccharide chains and affect superoxide production triggered through human Fcy gamma receptor I" European Journal of Biochemistry, vol. 267, pp. 7246-7256, 2000.

Plückthun, et al., New protein engineering approaches to multivalent and bispecific antibody fragments, Immunotechology, vol. 3, pp. 83-105, 1997.

* cited by examiner

FIG. 1

Comparisons of framework regions of light chain of antibody hTNF40 and human group 1 consensus sequences Hu group 1 consensus : DIQMTQSPSSLSASVGDRVTITC (SEQ ID NO: 87)
hTNF40 : DIVMTQSQKFMSTSVGDRVSVTC (SEQ ID NO: 88)

Hu Group 1 consensus : WYQQKPGKAPKLLIY (SEQ ID NO: 89)
hTNF40 : WYQQKPGQSPKALIY (SEQ ID NO: 90)

Hu Group 1 consensus : GVPSRFSGSGSGTDFTLTISSLQPEDFATYYC (SEQ ID NO: 91)
hTNF40 : GVPYRFTGSGSGTDFTLTISTVQSEDLAEYFC (SEQ ID NO: 92)

Hu Group 1 consensus : FGQGTKVEIKR (SEQ ID NO: 93)
hTNF40 : FGAGTKLELKR (SEQ ID NO: 94)

FIG. 3 Sequence of CDRs of hTNF40

H1 DYGMN (SEQ ID NO:1)

H2 WINTYIGEPIYVDDFKG (SEQ ID NO:7)

H2' WINTYIGEPIYADSVKG (SEQ ID NO:2)

H3 GYRSYAMDY (SEQ ID NO:3)

L1 KASQNVGTNVA (SEQ ID NO:4)

L2 SASFLYS (SEQ ID NO:5)

L3 QQYNIYPLT (SEQ ID NO:6)

FIG. 2

Comparisons of framework regions of heavy chain of antibody hTNF40 and human group 1 and group 3 consensus sequences Hu Group 1 consensus : QVQLVQSGAEVKKPGASVKVSCKASGYTFT (SEQ ID NO: 95)
hTNF40 : QIQLVQSGPELKKPGETVKISCKASGYVFT (SEQ ID NO: 96)

Hu Group 1 consensus : WVRQAPGQGLEWMG (SEQ ID NO: 97)
hTNF40 : WVKQAPGKAFKWMG (SEQ ID NO: 98)

Hu Group 1 consensus :RVTITRDTSTSTAYMELSSLRSEDTAVYYCAR (SEQ ID NO: 99)
hTNF40 :RFAFSLETSASTAFLQINNLKNEDTATYFCAR (SEQ ID NO: 100)

Hu Group 1 consensus : WGQGTLVTVSS (SEQ ID NO: 101)
hTNF40 : WGQGTTLTVSS (SEQ ID NO: 102)

Hu Group 3 consensus : EVQLVESGGGLVQPGGSLRLSCAASGFTFS (SEQ ID NO: 121)
hTNF40 : QIQLVQSGPELKKPGETVKISCKASGYVFT (SEQ ID NO: 96)

Hu Group 3 consensus : WVRQAPGKGLEWVS (SEQ ID NO: 122)
hTNF40 : WVKQAPGKAFKWMG (SEQ ID NO: 98)

Hu Group 3 consensus :RFTISRDNSKNTLYLQMNSLRAEDTAVYYCAR (SEQ ID NO: 123)
hTNF40 :RFAFSLETSASTAFLQINNLKNEDTATYFCAR (SEQ ID NO: 100)

Hu Group 3 consensus : WGQGTLVTVSS (SEQ ID NO: 124)
hTNF40 : WGQGTTLTVSS (SEQ ID NO: 102)

FIG. 6 Murine Vl Sequence of hTNF40 (SEQ ID NOS: 103 and 104)

```
              10                  20                  30                  40                  50
GAC ATT GTG ATG ACC CAG TCT CAA AAA TTC ATG TCC ACA TCA GTA GGA GAC AGG
CTG TAA CAC TAC TGG GTC AGA GTT TTT AAG TAC AGG TGT AGT CAT CCT CTG TCC
 D   I   V   M   T   Q   S   Q   K   F   M   S   T   S   V   G   D   R>

        60                  70                  80                  90                 100
GTC AGC GTC ACC TGC AAG GCC AGT CAG AAT GTG GGT ACT AAT GTA GCC TGG TAT
CAG TCG CAG TGG ACG TTC CGG TCA GTC TTA CAC CCA TGA TTA CAT CGG ACC ATA
 V   S   V   T   C   K   A   S   Q   N   V   G   T   N   V   A   W   Y>

110                120                 130                140                 150                 160
CAA CAG AAA CCA GGA CAA TCT CCT AAA GCA CTG ATT TAC TCG GCA TCC TTC CTA
GTT GTC TTT GGT CCT GTT AGA GGA TTT CGT GAC TAA ATG AGC CGT AGG AAG GAT
 Q   Q   K   P   G   Q   S   P   K   A   L   I   Y   S   A   S   F   L>

           170                 180                 190                 200                 210
TAT AGT GGA GTC CCT TAT CGC TTC ACA GGC AGT GGA TCT GGG ACA GAT TTC ACT
ATA TCA CCT CAG GGA ATA GCG AAG TGT CCG TCA CCT AGA CCC TGT CTA AAG TGA
 Y   S   G   V   P   Y   R   F   T   G   S   G   S   G   T   D   F   T>

  220                 230                 240                 250                 260                 270
CTC ACC ATC AGC ACT GTG CAG TCT GAA GAC TTG GCA GAG TAT TTC TGT CAG CAA
GAG TGG TAG TCG TGA CAC GTC AGA CTT CTG AAC CGT CTC ATA AAG ACA GTC GTT
 L   T   I   S   T   V   Q   S   E   D   L   A   E   Y   F   C   Q   Q>

              280                 290                 300                 310                 320
TAT AAC ATC TAT CCT CTC ACG TTC GGT GCT GGG ACC AAG CTG GAG CTG AAA CGT
ATA TTG TAG ATA GGA GAG TGC AAG CCA CGA CCC TGG TTC GAC CTC GAC TTT GCA
 Y   N   I   Y   P   L   T   F   G   A   G   T   K   L   E   L   K   R>
```

FIG. 7 Murine Vh Sequence of hTNF40 (SEQ ID NOS: 105 and 106)

```
              10                  20                  30                  40                  50
CAG ATC CAG TTG GTG CAG TCT GGA CCT GAG CTG AAG AAG CCT GGA GAG ACA GTC
GTC TAG GTC AAC CAC GTC AGA CCT GGA CTC GAC TTC TTC GGA CCT CTC TGT CAG
 Q   I   Q   L   V   Q   S   G   P   E   L   K   K   P   G   E   T   V>

       60                  70                  80                  90                 100
AAG ATC TCC TGC AAG GCT TCT GGA TAT GTT TTC ACA GAC TAT GGA ATG AAT TGG
TTC TAG AGG ACG TTC CGA AGA CCT ATA CAA AAG TGT CTG ATA CCT TAC TTA ACC
 K   I   S   C   K   A   S   G   Y   V   F   T   D   Y   G   M   N   W>

110                 120                 130                 140                 150                 160
GTG AAG CAG GCT CCA GGA AAG GCT TTC AAG TGG ATG GGC TGG ATA AAC ACC TAC
CAC TTC GTC CGA GGT CCT TTC CGA AAG TTC ACC TAC CCG ACC TAT TTG TGG ATG
 V   K   Q   A   P   G   K   A   F   K   W   M   G   W   I   N   T   Y>

          170                 180                 190                 200                 210
ATT GGA GAG CCA ATA TAT GTT GAT GAC TTC AAG GGA CGA TTT GCC TTC TCT TTG
TAA CCT CTC GGT TAT ATA CAA CTA CTG AAG TTC CCT GCT AAA CGG AAG AGA AAC
 I   G   E   P   I   Y   V   D   D   F   K   G   R   F   A   F   S   L>

  220                 230                 240                 250                 260                 270
GAA ACC TCT GCC AGC ACT GCC TTT TTG CAG ATC AAC AAC CTC AAA AAT GAG GAC
CTT TGG AGA CGG TCG TGA CGG AAA AAC GTC TAG TTG TTG GAG TTT TTA CTC CTG
 E   T   S   A   S   T   A   F   L   Q   I   N   N   L   K   N   E   D>

              280                 290                 300                 310                 320
ACG GCT ACA TAT TTC TGT GCA AGA GGT TAC CGG TCC TAT GCT ATG GAC TAC TGG
TGC CGA TGT ATA AAG ACA CGT TCT CCA ATG GCC AGG ATA CGA TAC CTG ATG ACC
 T   A   T   Y   F   C   A   R   G   Y   R   S   Y   A   M   D   Y   W>

       330                 340                 350
GGT CAA GGA ACC TCA GTC ACC GTC TCT TCA
CCA GTT CCT TGG AGT CAG TGG CAG AGA AGT
 G   Q   G   T   S   V   T   V   S   S>
```

FIG. 8 Grafted Vl Sequence of hTNF40 (SEQ ID NOS: 8 and 9)

```
                 10                  20                  30                  40                  50
GAC ATT CAA ATG ACC CAG AGC CCA TCC AGC CTG AGC GCA TCT GTA GGA GAC CGG
CTG TAA GTT TAC TGG GTC TCG GGT AGG TCG GAC TCG CGT AGA CAT CCT CTG GCC
 D   I   Q   M   T   Q   S   P   S   S   L   S   A   S   V   G   D   R>

         60                  70                  80                  90                 100
GTC ACC ATC ACT TGT AAA GCC AGT CAG AAC GTA GGT ACT AAC GTA GCC TGG TAT
CAG TGG TAG TGA ACA TTT CGG TCA GTC TTG CAT CCA TGA TTG CAT CGG ACC ATA
 V   T   I   T   C   K   A   S   Q   N   V   G   T   N   V   A   W   Y>

110                 120                 130                 140                 150                 160
CAG CAA AAA CCA GGT AAA GCC CCA AAA GCC CTC ATC TAC AGT GCC TCT TTC CTC
GTC GTT TTT GGT CCA TTT CGG GGT TTT CGG GAG TAG ATG TCA CGG AGA AAG GAG
 Q   Q   K   P   G   K   A   P   K   A   L   I   Y   S   A   S   F   L>

            170                 180                 190                 200                 210
TAT AGT GGT GTA CCA TAC AGG TTC AGC GGA TCC GGT AGT GGT ACT GAT TTC ACC
ATA TCA CCA CAT GGT ATG TCC AAG TCG CCT AGG CCA TCA CCA TGA CTA AAG TGG
 Y   S   G   V   P   Y   R   F   S   G   S   G   S   G   T   D   F   T>

  220                 230                 240                 250                 260                 270
CTC ACG ATC AGT AGC CTC CAG CCA GAA GAT TTC GCC ACT TAT TAC TGT CAA CAG
GAG TGC TAG TCA TCG GAG GTC GGT CTT CTA AAG CGG TGA ATA ATG ACA GTT GTC
 L   T   I   S   S   L   Q   P   E   D   F   A   T   Y   Y   C   Q   Q>

                280                 290                 300                 310                 320
TAT AAC ATC TAC CCA CTC ACA TTC GGT CAG GGT ACT AAA GTA GAA ATC AAA
ATA TTG TAG ATG GGT GAG TGT AAG CCA GTC CCA TGA TTT CAT CTT TAG TTT
 Y   N   I   Y   P   L   T   F   G   Q   G   T   K   V   E   I   K>
```

FIG. 9 Grafted Vl sequence of hTNF40 (SEQ ID NOS: 10 and 11)

```
                10                20                30                40                50
GAC ATT CAA ATG ACC CAG AGC CCA TCC AGC CTG AGC GCA TCT GTA GGA GAC CGG
CTG TAA GTT TAC TGG GTC TCG GGT AGG TCG GAC TCG CGT AGA CAT CCT CTG GCC
 D   I   Q   M   T   Q   S   P   S   S   L   S   A   S   V   G   D   R>

     60                70                80                90                100
GTC ACC ATC ACT TGT AAA GCC AGT CAG AAC GTA GGT ACT AAC GTA GCC TGG TAT
CAG TGG TAG TGA ACA TTT CGG TCA GTC TTG CAT CCA TGA TTG CAT CGG ACC ATA
 V   T   I   T   C   K   A   S   Q   N   V   G   T   N   V   A   W   Y>

110             120               130               140               150               160
CAG CAA AAA CCA GGT AAA GCC CCA AAA CTC CTC ATC TAC AGT GCC TCT TTC CTC
GTC GTT TTT GGT CCA TTT CGG GGT TTT GAG GAG TAG ATG TCA CGG AGA AAG GAG
 Q   Q   K   P   G   K   A   P   K   L   L   I   Y   S   A   S   F   L>

        170               180               190               200               210
TAT AGT GGT GTA CCA TAC AGG TTC AGC GGA TCC GGT AGT GGT ACT GAT TTC ACC
ATA TCA CCA CAT GGT ATG TCC AAG TCG CCT AGG CCA TCA CCA TGA CTA AAG TGG
 Y   S   G   V   P   Y   R   F   S   G   S   G   S   G   T   D   F   T>

  220               230               240               250               260               270
CTC ACG ATC AGT AGC CTC CAG CCA GAA GAT TTC GCC ACT TAT TAC TGT CAA CAG
GAG TGC TAG TCA TCG GAG GTC GGT CTT CTA AAG CGG TGA ATA ATG ACA GTT GTC
 L   T   I   S   S   L   Q   P   E   D   F   A   T   Y   Y   C   Q   Q>

            280               290               300               310               320
TAT AAC ATC TAC CCA CTC ACA TTC GGT CAG GGT ACT AAA GTA GAA ATC AAA
ATA TTG TAG ATG GGT GAG TGT AAG CCA GTC CCA TGA TTT CAT CTT TAG TTT
 Y   N   I   Y   P   L   T   F   G   Q   G   T   K   V   E   I   K>
```

FIG. 10 Grafted Vh sequence of hTNF40 (SEQ ID NOS: 12 and 13)

```
    10          20          30          40          50
CAG GTG CAG CTG GTC CAG TCA GGA GCA GAG GTT AAG AAG CCT GGT GCT TCC GTC
GTC CAC GTC GAC CAG GTC AGT CCT CGT CTC CAA TTC TTC GGA CCA CGA AGG CAG
 Q   V   Q   L   V   Q   S   G   A   E   V   K   K   P   G   A   S   V>

    60          70          80          90         100
AAA GTT TCG TGT AAG GCC TCA GGC TAC GTG TTC ACA GAC TAT GGT ATG AAT TGG
TTT CAA AGC ACA TTC CGG AGT CCG ATG CAC AAG TGT CTG ATA CCA TAC TTA ACC
 K   V   S   C   K   A   S   G   Y   V   F   T   D   Y   G   M   N   W>

110        120         130         140         150         160
GTC AGA CAG GCC CCG GGA CAA GGC CTG GAA TGG ATG GGT TGG ATT AAT ACT TAC
CAG TCT GTC CGG GGC CCT GTT CCG GAC CTT ACC TAC CCA ACC TAA TTA TGA ATG
 V   R   Q   A   P   G   Q   G   L   E   W   M   G   W   I   N   T   Y>

       170         180         190         200         210
ATT GGA GAG CCT ATT TAT GCT CAA AAG TTC CAG GGC AGA GTC ACG TTC ACT CTA
TAA CCT CTC GGA TAA ATA CGA GTT TTC AAG GTC CCG TCT CAG TGC AAG TGA GAT
 I   G   E   P   I   Y   A   Q   K   F   Q   G   R   V   T   F   T   L>

 220         230         240         250         260         270
GAC ACC TCC ACA AGC ACT GCA TAC ATG GAG CTG TCA TCT CTG AGA TCC GAG GAC
CTG TGG AGG TGT TCG TGA CGT ATG TAC CTC GAC AGT AGA GAC TCT AGG CTC CTG
 D   T   S   T   S   T   A   Y   M   E   L   S   S   L   R   S   E   D>

        280         290         300         310         320
ACC GCA GTG TAC TAT TGT GCT AGA GGA TAC AGA TCT TAT GCC ATG GAC TAC TGG
TGG CGT CAC ATG ATA ACA CGA TCT CCT ATG TCT AGA ATA CGG TAC CTG ATG ACC
 T   A   V   Y   Y   C   A   R   G   Y   R   S   Y   A   M   D   Y   W>

    330         340         350
GGC CAG GGT ACC CTA GTC ACA GTC TCC TCA
CCG GTC CCA TGG GAT CAG TGT CAG AGG AGT
 G   Q   G   T   L   V   T   V   S   S>
```

FIG. 11 Grafted Vh Sequence of hTNF40.4 (SEQ ID NOS: 14 and 15)

```
                  10                  20                  30                  40                  50
GAG GTT CAG CTG GTC GAG TCA GGA GGC GGT CTC GTG CAG CCT GGC GGA TCA CTG
CTC CAA GTC GAC CAG CTC AGT CCT CCG CCA GAG CAC GTC GGA CCG CCT AGT GAC
 E   V   Q   L   V   E   S   G   G   G   L   V   Q   P   G   G   S   L>

      60                  70                  80                  90                 100
AGA TTG TCC TGT GCT GCA TCT GGT TAC GTC TTC ACA GAC TAT GGA ATG AAT TGG
TCT AAC AGG ACA CGA CGT AGA CCA ATG CAG AAG TGT CTG ATA CCT TAC TTA ACC
 R   L   S   C   A   A   S   G   Y   V   F   T   D   Y   G   M   N   W>

110                 120                 130                 140                 150                 160
GTT AGA CAG GCC CCG GGA AAG GGC CTG GAA TGG ATG GGT TGG ATT AAT ACT TAC
CAA TCT GTC CGG GGC CCT TTC CCG GAC CTT ACC TAC CCA ACC TAA TTA TGA ATG
 V   R   Q   A   P   G   K   G   L   E   W   M   G   W   I   N   T   Y>

        170                 180                 190                 200                 210
ATT GGA GAG CCT ATT TAT GCT GAC AGC GTC AAG GGC AGA TTC ACG TTC TCT CTA
TAA CCT CTC GGA TAA ATA CGA CTG TCG CAG TTC CCG TCT AAG TGC AAG AGA GAT
 I   G   E   P   I   Y   A   D   S   V   K   G   R   F   T   F   S   L>

  220                 230                 240                 250                 260                 270
GAC ACA TCC AAG TCA ACA GCA TAC CTC CAA ATG AAT AGC CTG AGA GCA GAG GAC
CTG TGT AGG TTC AGT TGT CGT ATG GAG GTT TAC TTA TCG GAC TCT CGT CTC CTG
 D   T   S   K   S   T   A   Y   L   Q   M   N   S   L   R   A   E   D>

            280                 290                 300                 310                 320
ACC GCA GTG TAC TAT TGT GCT AGA GGA TAC AGA TCT TAT GCC ATG GAC TAC TGG
TGG CGT CAC ATG ATA ACA CGA TCT CCT ATG TCT AGA ATA CGG TAC CTG ATG ACC
 T   A   V   Y   Y   C   A   R   G   Y   R   S   Y   A   M   D   Y   W>

      330                 340                 350
GGC CAG GGT ACC CTA GTC ACA GTC TCC TCA
CCG GTC CCA TGG GAT CAG TGT CAG AGG AGT
 G   Q   G   T   L   V   T   V   S   S>
```

FIG. 15

Sequence of OmpA Oligonucleotide Adapter (SEQ ID NOS: 107 and 108)

```
                                                  OmpA Leader
                                           ┌──────►
           10          20          30          40
            *           *          |*           *
XhoI       XbaI        S.D.        |
T CGA GTT CTA GAT AAC GAG GCG TAA AAA ATG AAA AAG ACA
      CAA GAT CTA TTG CTC CGC ATT TTT TAC TTT TTC TGT
                                        M   K   K   T>

          50          60          70          80
           *           *           *           *
           MunI          StyI          SplI
GCT ATC GCA ATT GCA GTG GCC TTG GCT CTG ACG TAC GAG TCA
CGA TAG CGT TAA CGT CAC CGG AAC CGA GAC TGC ATG CTC AGT
 A   I   A   I   A   V   A   L   A

       90
        *
  EcoRI
GG
CCT TAA
```

- Internal restriction sites are shown in bold
- The 5' XhoI cohesive end ligates into the Vector SalI site, blocking it
- S.D. represents the OmpA Shine Dalgarno sequence FIG. 20 OLIGONUCLEOTIDE CASSETTES ENCODING DIFFERENT INTERGENIC SEQUENCES FOR E. Coli Fab' EXPRESSION IGS CASSETTE-1; Intergenic space = -1

Figure 20:
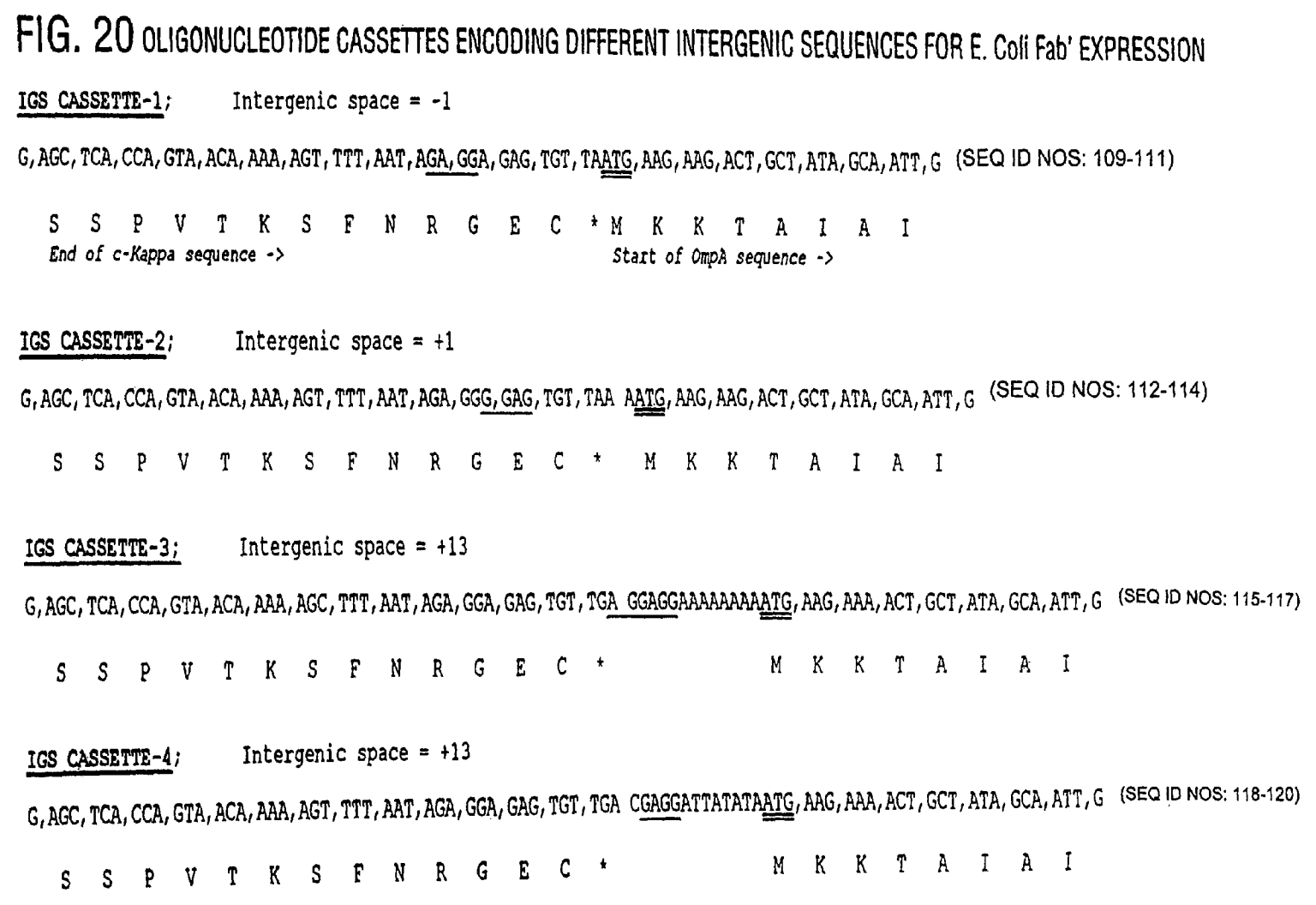

G,AGC,TCA,CCA,GTA,ACA,AAA,AGT,TTT,AAT,AGA,GGA,GAG,TGT,TAATG,AAG,AAG,ACT,GCT,ATA,GCA,ATT,G (SEQ ID NOS: 109-111)

S S P V T K S F N R G E C * M K K T A I A I

*End of c-Kappa sequence ->* *Start of OmpA sequence ->*

IGS CASSETTE-2; Intergenic space = +1

G,AGC,TCA,CCA,GTA,ACA,AAA,AGT,TTT,AAT,AGA,GGG,GAG,TGT,TAA AATG,AAG,AAG,ACT,GCT,ATA,GCA,ATT,G (SEQ ID NOS: 112-114)

S S P V T K S F N R G E C * M K K T A I A I

IGS CASSETTE-3; Intergenic space = +13

G,AGC,TCA,CCA,GTA,ACA,AAA,AGC,TTT,AAT,AGA,GGA,GAG,TGT,TGA GGAGGAAAAAAAAATG,AAG,AAA,ACT,GCT,ATA,GCA,ATT,G (SEQ ID NOS: 115-117)

S S P V T K S F N R G E C * M K K T A I A I

IGS CASSETTE-4; Intergenic space = +13

G,AGC,TCA,CCA,GTA,ACA,AAA,AGT,TTT,AAT,AGA,GGA,GAG,TGT,TGA CGAGGATTATATAATG,AAG,AAA,ACT,GCT,ATA,GCA,ATT,G (SEQ ID NOS: 118-120)

S S P V T K S F N R G E C * M K K T A I A I

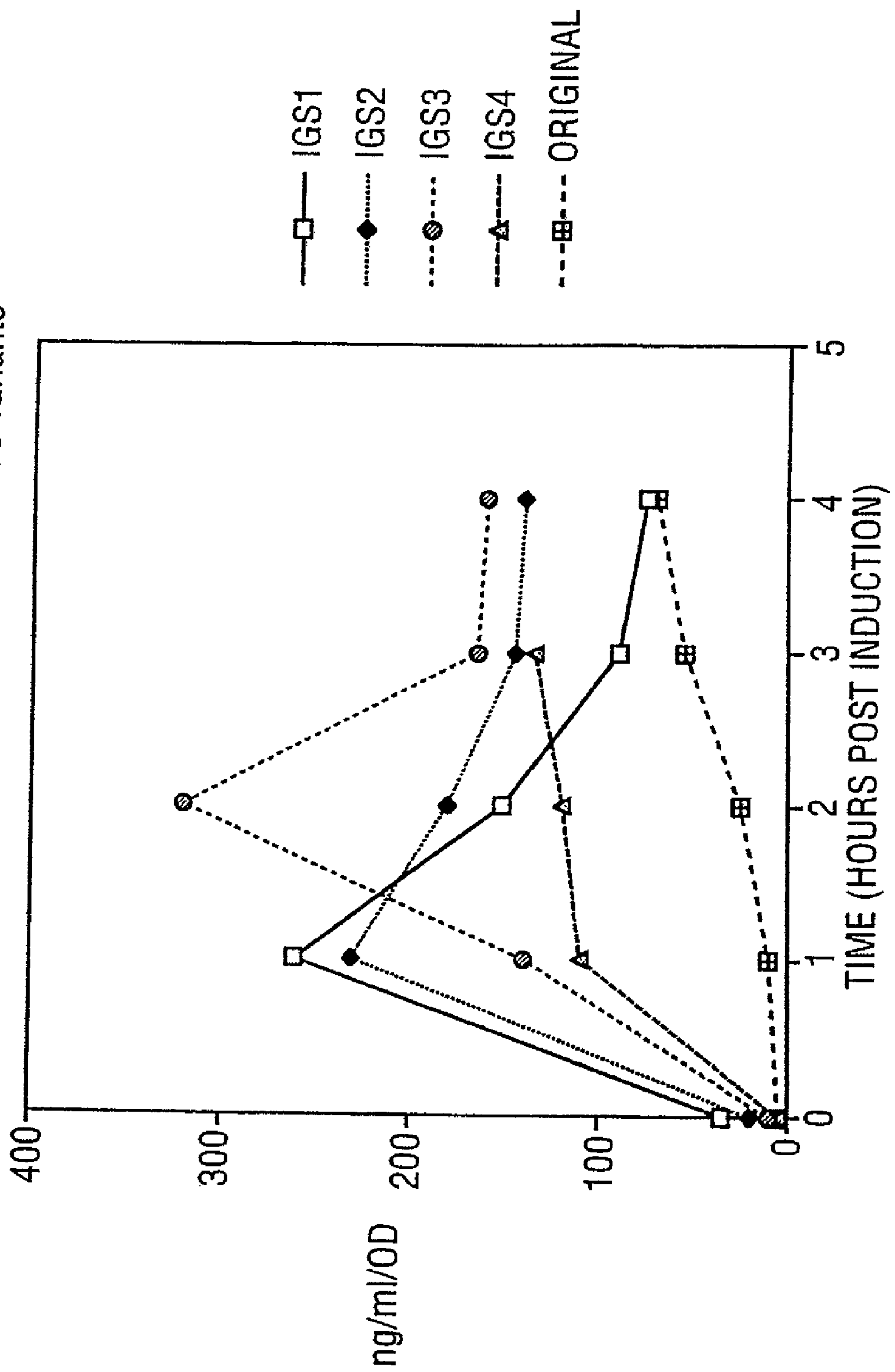
FIG. 21 Periplasmic Fab' accumulation - IGS variants

TENDER JOINTS
30
25
20
15
10
5
0
-2
0
2
4
6
8
WEEKS

SEQUENCE LISTING

```
<160> NUMBER OF SEQ ID NOS: 130

<210> SEQ ID NO 1
<211> LENGTH: 5
<212> TYPE: PRT
<213> ORGANISM: Artificial Sequence
<220> FEATURE:
<223> OTHER INFORMATION: hTNF40  CDRH1

<400> SEQUENCE: 1
```

```
Asp Tyr Gly Met Asn
1               5


<210> SEQ ID NO 2
<211> LENGTH: 17
<212> TYPE: PRT
<213> ORGANISM: Artificial Sequence
<220> FEATURE:
<223> OTHER INFORMATION: hTNF40/human hybrid CDRH2

<400> SEQUENCE: 2

Trp Ile Asn Thr Tyr Ile Gly Glu Pro Ile Tyr Ala Asp Ser Val Lys
1               5                   10                  15

Gly


<210> SEQ ID NO 3
<211> LENGTH: 9
<212> TYPE: PRT
<213> ORGANISM: Artificial Sequence
<220> FEATURE:
<223> OTHER INFORMATION: hTNF40  CDRH3

<400> SEQUENCE: 3

Gly Tyr Arg Ser Tyr Ala Met Asp Tyr
1               5


<210> SEQ ID NO 4
<211> LENGTH: 11
<212> TYPE: PRT
<213> ORGANISM: Artificial Sequence
<220> FEATURE:
<223> OTHER INFORMATION: hTNF40  CDRL1

<400> SEQUENCE: 4

Lys Ala Ser Gln Asn Val Gly Thr Asn Val Ala
1               5                   10


<210> SEQ ID NO 5
<211> LENGTH: 7
<212> TYPE: PRT
<213> ORGANISM: Artificial Sequence
<220> FEATURE:
<223> OTHER INFORMATION: hTNF40  CDRL2

<400> SEQUENCE: 5

Ser Ala Ser Phe Leu Tyr Ser
1               5


<210> SEQ ID NO 6
<211> LENGTH: 9
<212> TYPE: PRT
<213> ORGANISM: Artificial Sequence
<220> FEATURE:
<223> OTHER INFORMATION: hTNF40  CDRL3

<400> SEQUENCE: 6

Gln Gln Tyr Asn Ile Tyr Pro Leu Thr
1               5


<210> SEQ ID NO 7
<211> LENGTH: 17
<212> TYPE: PRT
<213> ORGANISM: Artificial Sequence
<220> FEATURE:
<223> OTHER INFORMATION: hTNF40  CDRH2

<400> SEQUENCE: 7
```

```
Trp Ile Asn Thr Tyr Ile Gly Glu Pro Ile Tyr Val Asp Asp Phe Lys
1               5                   10                  15

Gly


<210> SEQ ID NO 8
<211> LENGTH: 321
<212> TYPE: DNA
<213> ORGANISM: Artificial Sequence
<220> FEATURE:
<223> OTHER INFORMATION: hTF40-gL1
<220> FEATURE:
<221> NAME/KEY: CDS
<222> LOCATION: (1)..(321)
<223> OTHER INFORMATION:

<400> SEQUENCE: 8

gac att caa atg acc cag agc cca tcc agc ctg agc gca tct gta gga       48
Asp Ile Gln Met Thr Gln Ser Pro Ser Ser Leu Ser Ala Ser Val Gly
1               5                   10                  15

gac cgg gtc acc atc act tgt aaa gcc agt cag aac gta ggt act aac       96
Asp Arg Val Thr Ile Thr Cys Lys Ala Ser Gln Asn Val Gly Thr Asn
            20                  25                  30

gta gcc tgg tat cag caa aaa cca ggt aaa gcc cca aaa gcc ctc atc      144
Val Ala Trp Tyr Gln Gln Lys Pro Gly Lys Ala Pro Lys Ala Leu Ile
        35                  40                  45

tac agt gcc tct ttc ctc tat agt ggt gta cca tac agg ttc agc gga      192
Tyr Ser Ala Ser Phe Leu Tyr Ser Gly Val Pro Tyr Arg Phe Ser Gly
    50                  55                  60

tcc ggt agt ggt act gat ttc acc ctc acg atc agt agc ctc cag cca      240
Ser Gly Ser Gly Thr Asp Phe Thr Leu Thr Ile Ser Ser Leu Gln Pro
65                  70                  75                  80

gaa gat ttc gcc act tat tac tgt caa cag tat aac atc tac cca ctc      288
Glu Asp Phe Ala Thr Tyr Tyr Cys Gln Gln Tyr Asn Ile Tyr Pro Leu
                85                  90                  95

aca ttc ggt cag ggt act aaa gta gaa atc aaa                          321
Thr Phe Gly Gln Gly Thr Lys Val Glu Ile Lys
            100                 105


<210> SEQ ID NO 9
<211> LENGTH: 107
<212> TYPE: PRT
<213> ORGANISM: Artificial Sequence
<220> FEATURE:
<223> OTHER INFORMATION: hTF40-gL1

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105
```

```
<210> SEQ ID NO 10
<211> LENGTH: 321
<212> TYPE: DNA
<213> ORGANISM: Artificial Sequence
<220> FEATURE:
<223> OTHER INFORMATION: hNF40-gL2
<220> FEATURE:
<221> NAME/KEY: CDS
<222> LOCATION: (1)..(321)
<223> OTHER INFORMATION:

<400> SEQUENCE: 10

gac att caa atg acc cag agc cca tcc agc ctg agc gca tct gta gga       48
Asp Ile Gln Met Thr Gln Ser Pro Ser Ser Leu Ser Ala Ser Val Gly
1               5                   10                  15

gac cgg gtc acc atc act tgt aaa gcc agt cag aac gta ggt act aac       96
Asp Arg Val Thr Ile Thr Cys Lys Ala Ser Gln Asn Val Gly Thr Asn
            20                  25                  30

gta gcc tgg tat cag caa aaa cca ggt aaa gcc cca aaa ctc ctc atc      144
Val Ala Trp Tyr Gln Gln Lys Pro Gly Lys Ala Pro Lys Leu Leu Ile
        35                  40                  45

tac agt gcc tct ttc ctc tat agt ggt gta cca tac agg ttc agc gga      192
Tyr Ser Ala Ser Phe Leu Tyr Ser Gly Val Pro Tyr Arg Phe Ser Gly
    50                  55                  60

tcc ggt agt ggt act gat ttc acc ctc acg atc agt agc ctc cag cca      240
Ser Gly Ser Gly Thr Asp Phe Thr Leu Thr Ile Ser Ser Leu Gln Pro
65                  70                  75                  80

gaa gat ttc gcc act tat tac tgt caa cag tat aac atc tac cca ctc      288
Glu Asp Phe Ala Thr Tyr Tyr Cys Gln Gln Tyr Asn Ile Tyr Pro Leu
                85                  90                  95

aca ttc ggt cag ggt act aaa gta gaa atc aaa                          321
Thr Phe Gly Gln Gly Thr Lys Val Glu Ile Lys
            100                 105


<210> SEQ ID NO 11
<211> LENGTH: 107
<212> TYPE: PRT
<213> ORGANISM: Artificial Sequence
<220> FEATURE:
<223> OTHER INFORMATION: hNF40-gL2

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105


<210> SEQ ID NO 12
<211> LENGTH: 354
<212> TYPE: DNA
<213> ORGANISM: Artificial Sequence
<220> FEATURE:
<223> OTHER INFORMATION: gh1hTNF40.4  (Figure  10)
<220> FEATURE:
```

```
<221> NAME/KEY: CDS
<222> LOCATION: (1)..(354)
<223> OTHER INFORMATION:

<400> SEQUENCE: 12

cag gtg cag ctg gtc cag tca gga gca gag gtt aag aag cct ggt gct      48
Gln Val Gln Leu Val Gln Ser Gly Ala Glu Val Lys Lys Pro Gly Ala
1               5                   10                  15

tcc gtc aaa gtt tcg tgt aag gcc tca ggc tac gtg ttc aca gac tat      96
Ser Val Lys Val Ser Cys Lys Ala Ser Gly Tyr Val Phe Thr Asp Tyr
            20                  25                  30

ggt atg aat tgg gtc aga cag gcc ccg gga caa ggc ctg gaa tgg atg     144
Gly Met Asn Trp Val Arg Gln Ala Pro Gly Gln Gly Leu Glu Trp Met
        35                  40                  45

ggt tgg att aat act tac att gga gag cct att tat gct caa aag ttc     192
Gly Trp Ile Asn Thr Tyr Ile Gly Glu Pro Ile Tyr Ala Gln Lys Phe
    50                  55                  60

cag ggc aga gtc acg ttc act cta gac acc tcc aca agc act gca tac     240
Gln Gly Arg Val Thr Phe Thr Leu Asp Thr Ser Thr Ser Thr Ala Tyr
65                  70                  75                  80

atg gag ctg tca tct ctg aga tcc gag gac acc gca gtg tac tat tgt     288
Met Glu Leu Ser Ser Leu Arg Ser Glu Asp Thr Ala Val Tyr Tyr Cys
                85                  90                  95

gct aga gga tac aga tct tat gcc atg gac tac tgg ggc cag ggt acc     336
Ala Arg Gly Tyr Arg Ser Tyr Ala Met Asp Tyr Trp Gly Gln Gly Thr
            100                 105                 110

cta gtc aca gtc tcc tca                                             354
Leu Val Thr Val Ser Ser
        115


<210> SEQ ID NO 13
<211> LENGTH: 118
<212> TYPE: PRT
<213> ORGANISM: Artificial Sequence
<220> FEATURE:
<223> OTHER INFORMATION: gh1hTNF40.4  (Figure  10)

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Val Phe Thr Asp Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ile Gly Glu Pro Ile Tyr Ala Gln Lys Phe
    50                  55                  60

Gln Gly Arg Val Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115


<210> SEQ ID NO 14
<211> LENGTH: 354
<212> TYPE: DNA
<213> ORGANISM: Artificial Sequence
<220> FEATURE:
<223> OTHER INFORMATION: gh3hTNF40.4  (Figure 11)
<220> FEATURE:
```

```
<221> NAME/KEY: CDS
<222> LOCATION: (1)..(354)
<223> OTHER INFORMATION:

<400> SEQUENCE: 14

gag gtt cag ctg gtc gag tca gga ggc ggt ctc gtg cag cct ggc gga       48
Glu Val Gln Leu Val Glu Ser Gly Gly Gly Leu Val Gln Pro Gly Gly
1               5                   10                  15

tca ctg aga ttg tcc tgt gct gca tct ggt tac gtc ttc aca gac tat       96
Ser Leu Arg Leu Ser Cys Ala Ala Ser Gly Tyr Val Phe Thr Asp Tyr
            20                  25                  30

gga atg aat tgg gtt aga cag gcc ccg gga aag ggc ctg gaa tgg atg      144
Gly Met Asn Trp Val Arg Gln Ala Pro Gly Lys Gly Leu Glu Trp Met
        35                  40                  45

ggt tgg att aat act tac att gga gag cct att tat gct gac agc gtc      192
Gly Trp Ile Asn Thr Tyr Ile Gly Glu Pro Ile Tyr Ala Asp Ser Val
    50                  55                  60

aag ggc aga ttc acg ttc tct cta gac aca tcc aag tca aca gca tac      240
Lys Gly Arg Phe Thr Phe Ser Leu Asp Thr Ser Lys Ser Thr Ala Tyr
65                  70                  75                  80

ctc caa atg aat agc ctg aga gca gag gac acc gca gtg tac tat tgt      288
Leu Gln Met Asn Ser Leu Arg Ala Glu Asp Thr Ala Val Tyr Tyr Cys
                85                  90                  95

gct aga gga tac aga tct tat gcc atg gac tac tgg ggc cag ggt acc      336
Ala Arg Gly Tyr Arg Ser Tyr Ala Met Asp Tyr Trp Gly Gln Gly Thr
            100                 105                 110

cta gtc aca gtc tcc tca                                              354
Leu Val Thr Val Ser Ser
        115


<210> SEQ ID NO 15
<211> LENGTH: 118
<212> TYPE: PRT
<213> ORGANISM: Artificial Sequence
<220> FEATURE:
<223> OTHER INFORMATION: gh3hTNF40.4  (Figure 11)

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115


<210> SEQ ID NO 16
<211> LENGTH: 9
<212> TYPE: DNA
<213> ORGANISM: Artificial Sequence
<220> FEATURE:
<223> OTHER INFORMATION: Primer
```

<400> SEQUENCE: 16 gccgccacc 9

<210> SEQ ID NO 17
<211> LENGTH: 26
<212> TYPE: DNA
<213> ORGANISM: Artificial Sequence
<220> FEATURE:
<223> OTHER INFORMATION: Primer CH1

<400> SEQUENCE: 17
atgaaatgca gctgggtcat sttctt 26

<210> SEQ ID NO 18
<211> LENGTH: 26
<212> TYPE: DNA
<213> ORGANISM: Artificial Sequence
<220> FEATURE:
<223> OTHER INFORMATION: Primer CH2

<400> SEQUENCE: 18
atgggatgga gctrtatcat sytctt 26

<210> SEQ ID NO 19
<211> LENGTH: 26
<212> TYPE: DNA
<213> ORGANISM: Artificial Sequence
<220> FEATURE:
<223> OTHER INFORMATION: Primer CH3

<400> SEQUENCE: 19
atgaagwtgt ggttaaactg ggtttt 26

<210> SEQ ID NO 20
<211> LENGTH: 23
<212> TYPE: DNA
<213> ORGANISM: Artificial Sequence
<220> FEATURE:
<223> OTHER INFORMATION: Primer CH4

<400> SEQUENCE: 20
atgractttg ggytcagctt grt 23

<210> SEQ ID NO 21
<211> LENGTH: 26
<212> TYPE: DNA
<213> ORGANISM: Artificial Sequence
<220> FEATURE:
<223> OTHER INFORMATION: Primer CH5

<400> SEQUENCE: 21
atggactcca ggctcaattt agtttt 26

<210> SEQ ID NO 22
<211> LENGTH: 26
<212> TYPE: DNA
<213> ORGANISM: Artificial Sequence
<220> FEATURE:
<223> OTHER INFORMATION: Primer CH6

<400> SEQUENCE: 22
atggctgtcy trgsgctrct cttctg 26

<210> SEQ ID NO 23
<211> LENGTH: 26
<212> TYPE: DNA

<213> ORGANISM: Artificial Sequence
<220> FEATURE:
<223> OTHER INFORMATION: Primer CH7

<400> SEQUENCE: 23
atggratgga gckggrtctt tmtctt 26

<210> SEQ ID NO 24
<211> LENGTH: 23
<212> TYPE: DNA
<213> ORGANISM: Artificial Sequence
<220> FEATURE:
<223> OTHER INFORMATION: Primer CH8

<400> SEQUENCE: 24
atgagagtgc tgattctttt gtg 23

<210> SEQ ID NO 25
<211> LENGTH: 26
<212> TYPE: DNA
<213> ORGANISM: Artificial Sequence
<220> FEATURE:
<223> OTHER INFORMATION: Primer CH9

<400> SEQUENCE: 25
atggmttggg tgtggamctt gctatt 26

<210> SEQ ID NO 26
<211> LENGTH: 26
<212> TYPE: DNA
<213> ORGANISM: Artificial Sequence
<220> FEATURE:
<223> OTHER INFORMATION: Primer CH10

<400> SEQUENCE: 26
atgggcagac ttacattctc attcct 26

<210> SEQ ID NO 27
<211> LENGTH: 28
<212> TYPE: DNA
<213> ORGANISM: Artificial Sequence
<220> FEATURE:
<223> OTHER INFORMATION: Primer CH11

<400> SEQUENCE: 27
atggattttg ggctgatttt ttttattg 28

<210> SEQ ID NO 28
<211> LENGTH: 26
<212> TYPE: DNA
<213> ORGANISM: Artificial Sequence
<220> FEATURE:
<223> OTHER INFORMATION: Primer CH12

<400> SEQUENCE: 28
atgatggtgt taagtcttct gtacct 26

<210> SEQ ID NO 29
<211> LENGTH: 21
<212> TYPE: DNA
<213> ORGANISM: Artificial Sequence
<220> FEATURE:
<223> OTHER INFORMATION: 5' end

<400> SEQUENCE: 29
gcgcgcaagc ttgccgccac c 21

<210> SEQ ID NO 30
<211> LENGTH: 29
<212> TYPE: DNA
<213> ORGANISM: Artificial Sequence
<220> FEATURE:
<223> OTHER INFORMATION: Primer CL1

<400> SEQUENCE: 30
atgaagttgc ctgttaggct gttggtgct 29

<210> SEQ ID NO 31
<211> LENGTH: 29
<212> TYPE: DNA
<213> ORGANISM: Artificial Sequence
<220> FEATURE:
<223> OTHER INFORMATION: Primer CL2

<400> SEQUENCE: 31
atggagwcag acacactcct gytatgggt 29

<210> SEQ ID NO 32
<211> LENGTH: 23
<212> TYPE: DNA
<213> ORGANISM: Artificial Sequence
<220> FEATURE:
<223> OTHER INFORMATION: Primer CL3

<400> SEQUENCE: 32
atgagtgtgc tcactcaggt cct 23

<210> SEQ ID NO 33
<211> LENGTH: 26
<212> TYPE: DNA
<213> ORGANISM: Artificial Sequence
<220> FEATURE:
<223> OTHER INFORMATION: Primer CL4

<400> SEQUENCE: 33
atgaggrccc ctgctcagwt tyttgg 26

<210> SEQ ID NO 34
<211> LENGTH: 29
<212> TYPE: DNA
<213> ORGANISM: Artificial Sequence
<220> FEATURE:
<223> OTHER INFORMATION: Primer CL5

<400> SEQUENCE: 34
atggatttwc aggtgcagat twtcagctt 29

<210> SEQ ID NO 35
<211> LENGTH: 29
<212> TYPE: DNA
<213> ORGANISM: Artificial Sequence
<220> FEATURE:
<223> OTHER INFORMATION: Primer CL5A

<400> SEQUENCE: 35
atggatttwc argtgcagat twtcagctt 29

<210> SEQ ID NO 36
<211> LENGTH: 26
<212> TYPE: DNA
<213> ORGANISM: Artificial Sequence
<220> FEATURE:
<223> OTHER INFORMATION: Primer CL6

<400> SEQUENCE: 36
atgaggtkcy ytgytsagyt yctgrg 26

<210> SEQ ID NO 37
<211> LENGTH: 23
<212> TYPE: DNA
<213> ORGANISM: Artificial Sequence
<220> FEATURE:
<223> OTHER INFORMATION: Primer CL7

<400> SEQUENCE: 37
atgggcwtca agatggagtc aca 23

<210> SEQ ID NO 38
<211> LENGTH: 29
<212> TYPE: DNA
<213> ORGANISM: Artificial Sequence
<220> FEATURE:
<223> OTHER INFORMATION: Primer CL8

<400> SEQUENCE: 38
atgtggggay ctktttycmm tttttcaat 29

<210> SEQ ID NO 39
<211> LENGTH: 24
<212> TYPE: DNA
<213> ORGANISM: Artificial Sequence
<220> FEATURE:
<223> OTHER INFORMATION: Primer CL9

<400> SEQUENCE: 39
atggtrtccw casctcagtt cctt 24

<210> SEQ ID NO 40
<211> LENGTH: 26
<212> TYPE: DNA
<213> ORGANISM: Artificial Sequence
<220> FEATURE:
<223> OTHER INFORMATION: Primer CL10

<400> SEQUENCE: 40
atgtatatat gtttgttgtc tatttc 26

<210> SEQ ID NO 41
<211> LENGTH: 26
<212> TYPE: DNA
<213> ORGANISM: Artificial Sequence
<220> FEATURE:
<223> OTHER INFORMATION: Primer CL11

<400> SEQUENCE: 41
atggaagccc cagctcagct tctctt 26

<210> SEQ ID NO 42
<211> LENGTH: 26
<212> TYPE: DNA
<213> ORGANISM: Artificial Sequence
<220> FEATURE:
<223> OTHER INFORMATION: Primer CL12A

<400> SEQUENCE: 42
atgragtywc agacccaggt cttyrt 26

<210> SEQ ID NO 43
<211> LENGTH: 26
<212> TYPE: DNA

<213> ORGANISM: Artificial Sequence
<220> FEATURE:
<223> OTHER INFORMATION: Primer CL12B

<400> SEQUENCE: 43
atggagacac attctcaggt ctttgt 26

<210> SEQ ID NO 44
<211> LENGTH: 26
<212> TYPE: DNA
<213> ORGANISM: Artificial Sequence
<220> FEATURE:
<223> OTHER INFORMATION: Primer CL13

<400> SEQUENCE: 44
atggattcac aggcccaggt tcttat 26

<210> SEQ ID NO 45
<211> LENGTH: 26
<212> TYPE: DNA
<213> ORGANISM: Artificial Sequence
<220> FEATURE:
<223> OTHER INFORMATION: Primer CL14

<400> SEQUENCE: 45
atgatgagtc ctgcccagtt cctgtt 26

<210> SEQ ID NO 46
<211> LENGTH: 29
<212> TYPE: DNA
<213> ORGANISM: Artificial Sequence
<220> FEATURE:
<223> OTHER INFORMATION: Primer CL15

<400> SEQUENCE: 46
atgaatttgc ctgttcatct cttggtgct 29

<210> SEQ ID NO 47
<211> LENGTH: 29
<212> TYPE: DNA
<213> ORGANISM: Artificial Sequence
<220> FEATURE:
<223> OTHER INFORMATION: Primer CL16

<400> SEQUENCE: 47
atggattttc aattggtcct catctcctt 29

<210> SEQ ID NO 48
<211> LENGTH: 26
<212> TYPE: DNA
<213> ORGANISM: Artificial Sequence
<220> FEATURE:
<223> OTHER INFORMATION: Primer CL17A

<400> SEQUENCE: 48
atgaggtgcc tarctsagtt cctgrg 26

<210> SEQ ID NO 49
<211> LENGTH: 26
<212> TYPE: DNA
<213> ORGANISM: Artificial Sequence
<220> FEATURE:
<223> OTHER INFORMATION: Primer CL17B

<400> SEQUENCE: 49
atgaagtact ctgctcagtt tctagg 26

<210> SEQ ID NO 50
<211> LENGTH: 26
<212> TYPE: DNA
<213> ORGANISM: Artificial Sequence
<220> FEATURE:
<223> OTHER INFORMATION: Primer CL17C

<400> SEQUENCE: 50
atgaggcatt ctcttcaatt cttggg 26

<210> SEQ ID NO 51
<211> LENGTH: 21
<212> TYPE: DNA
<213> ORGANISM: Artificial Sequence
<220> FEATURE:
<223> OTHER INFORMATION: 5' end

<400> SEQUENCE: 51
ggactgttcg aagccgccac c 21

<210> SEQ ID NO 52
<211> LENGTH: 30
<212> TYPE: DNA
<213> ORGANISM: Artificial Sequence
<220> FEATURE:
<223> OTHER INFORMATION: Primer CL12

<400> SEQUENCE: 52
ggatacagtt ggtgcagcat ccgtacgttt 30

<210> SEQ ID NO 53
<211> LENGTH: 37
<212> TYPE: DNA
<213> ORGANISM: Artificial Sequence
<220> FEATURE:
<223> OTHER INFORMATION: Primer R2155

<400> SEQUENCE: 53
gcagatgggc ccttcgttga ggctgmrgag acdgtga 37

<210> SEQ ID NO 54
<211> LENGTH: 24
<212> TYPE: DNA
<213> ORGANISM: Artificial Sequence
<220> FEATURE:
<223> OTHER INFORMATION: Primer R1053

<400> SEQUENCE: 54
gctgacagac taacagactg ttcc 24

<210> SEQ ID NO 55
<211> LENGTH: 18
<212> TYPE: DNA
<213> ORGANISM: Artificial Sequence
<220> FEATURE:
<223> OTHER INFORMATION: Primer R720

<400> SEQUENCE: 55
gctctcggag gtgctcct 18

<210> SEQ ID NO 56
<211> LENGTH: 70
<212> TYPE: DNA
<213> ORGANISM: Artificial Sequence
<220> FEATURE:
<223> OTHER INFORMATION: Oligonucletide P7982

<400> SEQUENCE: 56
gaattcaggg tcaccatcac ttgtaaagcc agtcagaacg taggtactaa cgtagcctgg 60
tatcagcaaa 70

<210> SEQ ID NO 57
<211> LENGTH: 71
<212> TYPE: DNA
<213> ORGANISM: Artificial Sequence
<220> FEATURE:
<223> OTHER INFORMATION: Oligonucleotide P7983

<400> SEQUENCE: 57
atagaggaaa gaggcactgt agatgagggc ttttggggct ttacctggtt tttgctgata 60
ccaggctacg t 71

<210> SEQ ID NO 58
<211> LENGTH: 71
<212> TYPE: DNA
<213> ORGANISM: Artificial Sequence
<220> FEATURE:
<223> OTHER INFORMATION: Oligonucletide P7984

<400> SEQUENCE: 58
tacagtgcct ctttcctcta tagtggtgta ccatacaggt tcagcggatc cggtagtggt 60
actgatttca c 71

<210> SEQ ID NO 59
<211> LENGTH: 71
<212> TYPE: DNA
<213> ORGANISM: Artificial Sequence
<220> FEATURE:
<223> OTHER INFORMATION: Oligonucleotide P7985

<400> SEQUENCE: 59
gacagtaata agtggcgaaa tcttctggct ggaggctact gatcgtgagg gtgaaatcag 60
taccactacc g 71

<210> SEQ ID NO 60
<211> LENGTH: 89
<212> TYPE: DNA
<213> ORGANISM: Artificial Sequence
<220> FEATURE:
<223> OTHER INFORMATION: Oligonucleotide P7986

<400> SEQUENCE: 60
atttcgccac ttattactgt caacagtata acatctaccc actcacattc ggtcagggta 60
ctaaagtaga aatcaaacgt acggaattc 89

<210> SEQ ID NO 61
<211> LENGTH: 30
<212> TYPE: DNA
<213> ORGANISM: Artificial Sequence
<220> FEATURE:
<223> OTHER INFORMATION: Oligonucleotide P7981

<400> SEQUENCE: 61
gaattcaggg tcaccatcac ttgtaaagcc 30

<210> SEQ ID NO 62
<211> LENGTH: 30
<212> TYPE: DNA
<213> ORGANISM: Artificial Sequence
<220> FEATURE:

<223> OTHER INFORMATION: Oligonucleotide P7980

<400> SEQUENCE: 62
gaattccgta cgtttgattt ctactttagt 30

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide R1053

<400> SEQUENCE: 63
gctgacagac taacagactg ttcc 24

<210> SEQ ID NO 64
<211> LENGTH: 57
<212> TYPE: DNA
<213> ORGANISM: Artificial Sequence
<220> FEATURE:
<223> OTHER INFORMATION: Oligonucleotide R5350

<400> SEQUENCE: 64
tctagatggc acaccatctg ctaagtttga tgcagcatag atcaggagct taggagc 57

<210> SEQ ID NO 65
<211> LENGTH: 59
<212> TYPE: DNA
<213> ORGANISM: Artificial Sequence
<220> FEATURE:
<223> OTHER INFORMATION: Oligonucleotide R5349

<400> SEQUENCE: 65
gcagatggtg tgccatctag attcagtggc agtggatcag gcacagactt taccctaac 59

<210> SEQ ID NO 66
<211> LENGTH: 18
<212> TYPE: DNA
<213> ORGANISM: Artificial Sequence
<220> FEATURE:
<223> OTHER INFORMATION: Oligonucleotide R684

<400> SEQUENCE: 66
ttcaactgct catcagat 18

<210> SEQ ID NO 67
<211> LENGTH: 65
<212> TYPE: DNA
<213> ORGANISM: Artificial Sequence
<220> FEATURE:
<223> OTHER INFORMATION: Primer P7989

<400> SEQUENCE: 67
gaagcaccag gcttcttaac ctctgctcct gactggacca gctgcacctg agagtgcacg 60
aattc 65

<210> SEQ ID NO 68
<211> LENGTH: 71
<212> TYPE: DNA
<213> ORGANISM: Artificial Sequence
<220> FEATURE:
<223> OTHER INFORMATION: Primer P7990

<400> SEQUENCE: 68
ggttaagaag cctggtgctt ccgtcaaagt ttcgtgtaag gcctcaggct acgtgttcac 60
agactatggt a 71

<210> SEQ ID NO 69
<211> LENGTH: 71
<212> TYPE: DNA
<213> ORGANISM: Artificial Sequence
<220> FEATURE:
<223> OTHER INFORMATION: Primer P7991

<400> SEQUENCE: 69
ccaacccatc catttcaggc cttgtcccgg ggcctgcttg acccaattca taccatagtc 60
tgtgaacacg t 71

<210> SEQ ID NO 70
<211> LENGTH: 81
<212> TYPE: DNA
<213> ORGANISM: Artificial Sequence
<220> FEATURE:
<223> OTHER INFORMATION: Primer P7995

<400> SEQUENCE: 70
ggcctgaaat ggatgggttg gattaatact tacattggag agcctattta tgttgacgac 60
ttcaagggca gattcacgtt c 81

<210> SEQ ID NO 71
<211> LENGTH: 56
<212> TYPE: DNA
<213> ORGANISM: Artificial Sequence
<220> FEATURE:
<223> OTHER INFORMATION: Primer P7992

<400> SEQUENCE: 71
ccatgtatgc agtgcgttgt ggaggtgtct agagtgaacg tgaatctgcc cttgaa 56

<210> SEQ ID NO 72
<211> LENGTH: 62
<212> TYPE: DNA
<213> ORGANISM: Artificial Sequence
<220> FEATURE:
<223> OTHER INFORMATION: Primer P7993

<400> SEQUENCE: 72
ccacaagcac tgcatacatg gagctgtcat ctctgagatc cgaggacacc gcagtgtact 60
at 62

<210> SEQ ID NO 73
<211> LENGTH: 78
<212> TYPE: DNA
<213> ORGANISM: Artificial Sequence
<220> FEATURE:
<223> OTHER INFORMATION: Primer P7994

<400> SEQUENCE: 73
gaattcggta ccctggcccc agtagtccat ggcataagat ctgtatcctc tagcacaata 60
gtacactgcg gtgtcctc 78

<210> SEQ ID NO 74
<211> LENGTH: 30
<212> TYPE: DNA
<213> ORGANISM: Artificial Sequence
<220> FEATURE:
<223> OTHER INFORMATION: Primer 7988

<400> SEQUENCE: 74

```
gaattcgtgc actctcaggt gcagctggtc                                        30


<210> SEQ ID NO 75
<211> LENGTH: 30
<212> TYPE: DNA
<213> ORGANISM: Artificial Sequence
<220> FEATURE:
<223> OTHER INFORMATION: Primer P7987

<400> SEQUENCE: 75

gaattcggta ccctggcccc agtagtccat                                        30


<210> SEQ ID NO 76
<211> LENGTH: 65
<212> TYPE: DNA
<213> ORGANISM: Artificial Sequence
<220> FEATURE:
<223> OTHER INFORMATION: Primer P7999

<400> SEQUENCE: 76

gatccgccag gctgcacgag accgcctcct gactcgacca gctgaacctc agagtgcacg       60

aattc                                                                   65


<210> SEQ ID NO 77
<211> LENGTH: 71
<212> TYPE: DNA
<213> ORGANISM: Artificial Sequence
<220> FEATURE:
<223> OTHER INFORMATION: Primer P8000

<400> SEQUENCE: 77

tctcgtgcag cctggcggat cgctgagatt gtcctgtgct gcatctggtt acgtcttcac       60

agactatgga a                                                            71


<210> SEQ ID NO 78
<211> LENGTH: 71
<212> TYPE: DNA
<213> ORGANISM: Artificial Sequence
<220> FEATURE:
<223> OTHER INFORMATION: Primer P8001

<400> SEQUENCE: 78

ccaacccatc catttcaggc cctttcccgg ggcctgctta acccaattca ttccatagtc       60

tgtgaagacg t                                                            71


<210> SEQ ID NO 79
<211> LENGTH: 55
<212> TYPE: DNA
<213> ORGANISM: Artificial Sequence
<220> FEATURE:
<223> OTHER INFORMATION: Primer P7997

<400> SEQUENCE: 79

ggaggtatgc tgttgacttg gatgtgtcta gagagaacgt gaatctgccc ttgaa            55


<210> SEQ ID NO 80
<211> LENGTH: 62
<212> TYPE: DNA
<213> ORGANISM: Artificial Sequence
<220> FEATURE:
<223> OTHER INFORMATION: Primer P7998

<400> SEQUENCE: 80

ccaagtcaac agcatacctc caaatgaata gcctgagagc agaggacacc gcagtgtact       60
```

at 62

<210> SEQ ID NO 81
<211> LENGTH: 78
<212> TYPE: DNA
<213> ORGANISM: Artificial Sequence
<220> FEATURE:
<223> OTHER INFORMATION: Primer P7993

<400> SEQUENCE: 81
gaattcggta ccctggcccc agtagtccat ggcataagat ctgtatcctc tagcacaata 60
gtacactgcg gtgtcctc 78

<210> SEQ ID NO 82
<211> LENGTH: 30
<212> TYPE: DNA
<213> ORGANISM: Artificial Sequence
<220> FEATURE:
<223> OTHER INFORMATION: Primer P7996

<400> SEQUENCE: 82
gaattcgtgc actctgaggt tcagctggtc 30

<210> SEQ ID NO 83
<211> LENGTH: 74
<212> TYPE: DNA
<213> ORGANISM: Artificial Sequence
<220> FEATURE:
<223> OTHER INFORMATION: 5' Primer

<400> SEQUENCE: 83
cgcgcggcaa ttgcagtggc cttggctggt ttcgctaccg tagcgcaagc tgacattcaa 60
atgacccaga gccc 74

<210> SEQ ID NO 84
<211> LENGTH: 20
<212> TYPE: DNA
<213> ORGANISM: Artificial Sequence
<220> FEATURE:
<223> OTHER INFORMATION: 3' Primer

<400> SEQUENCE: 84
ttcaactgct catcagatgg 20

<210> SEQ ID NO 85
<211> LENGTH: 78
<212> TYPE: DNA
<213> ORGANISM: Artificial Sequence
<220> FEATURE:
<223> OTHER INFORMATION: 5' Primer

<400> SEQUENCE: 85
gctatcgcaa ttgcagtggc gctagctggt ttcgccaccg tggcgcaagc tgaggttcag 60
ctggtcgagt caggaggc 78

<210> SEQ ID NO 86
<211> LENGTH: 18
<212> TYPE: DNA
<213> ORGANISM: Artificial Sequence
<220> FEATURE:
<223> OTHER INFORMATION: 3' Primer

<400> SEQUENCE: 86
gcctgagttc cacgacac 18

<210> SEQ ID NO 87
<211> LENGTH: 23
<212> TYPE: PRT
<213> ORGANISM: Artificial Sequence
<220> FEATURE:
<223> OTHER INFORMATION: Human Group 1 consensus framework L1

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 88
<211> LENGTH: 69
<212> TYPE: PRT
<213> ORGANISM: Artificial Sequence
<220> FEATURE:
<223> OTHER INFORMATION: hTNF40 framework L1

<400> SEQUENCE: 88

```
Ala Ser Pro Ile Leu Glu Val Ala Leu Met Glu Thr Thr His Arg Gly
1               5                   10                  15

Leu Asn Ser Glu Arg Gly Leu Asn Leu Tyr Ser Pro His Glu Met Glu
            20                  25                  30

Thr Ser Glu Arg Thr His Arg Ser Glu Arg Val Ala Leu Gly Leu Tyr
        35                  40                  45

Ala Ser Pro Ala Arg Gly Val Ala Leu Ser Glu Arg Val Ala Leu Thr
    50                  55                  60

His Arg Cys Tyr Ser
65
```

<210> SEQ ID NO 89
<211> LENGTH: 15
<212> TYPE: PRT
<213> ORGANISM: Artificial Sequence
<220> FEATURE:
<223> OTHER INFORMATION: Human group 1 consensus framework L2

<400> SEQUENCE: 89

```
Trp Tyr Gln Gln Lys Pro Gly Lys Ala Pro Lys Leu Leu Ile Tyr
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: hTNF40 framework L2

<400> SEQUENCE: 90

```
Trp Tyr Gln Gln Lys Pro Gly Gln Ser Pro Lys Ala Leu Ile Tyr
1               5                   10                  15
```

<210> SEQ ID NO 91
<211> LENGTH: 32
<212> TYPE: PRT
<213> ORGANISM: Artificial Sequence
<220> FEATURE:
<223> OTHER INFORMATION: Human group 1 consensus framework L3

<400> SEQUENCE: 91

```
Gly Val Pro Ser Arg Phe Ser Gly Ser Gly Ser Gly Thr Asp Phe Thr
1               5                   10                  15
```

```
Leu Thr Ile Ser Ser Leu Gln Pro Glu Asp Phe Ala Thr Tyr Tyr Cys
            20                  25                  30


<210> SEQ ID NO 92
<211> LENGTH: 32
<212> TYPE: PRT
<213> ORGANISM: Artificial Sequence
<220> FEATURE:
<223> OTHER INFORMATION: hTNF40 framework L3

<400> SEQUENCE: 92

Gly Val Pro Tyr Arg Phe Thr Gly Ser Gly Ser Gly Thr Asp Phe Thr
1               5                   10                  15

Leu Thr Ile Ser Thr Val Gln Ser Glu Asp Leu Ala Glu Tyr Phe Cys
            20                  25                  30


<210> SEQ ID NO 93
<211> LENGTH: 11
<212> TYPE: PRT
<213> ORGANISM: Artificial Sequence
<220> FEATURE:
<223> OTHER INFORMATION: Human group 1 consensus framework L4

<400> SEQUENCE: 93

Phe Gly Gln Gly Thr Lys Val Glu Ile Lys Arg
1               5                   10


<210> SEQ ID NO 94
<211> LENGTH: 11
<212> TYPE: PRT
<213> ORGANISM: Artificial Sequence
<220> FEATURE:
<223> OTHER INFORMATION: hTNF40 framework L4

<400> SEQUENCE: 94

Phe Gly Ala Gly Thr Lys Leu Glu Leu Lys Arg
1               5                   10


<210> SEQ ID NO 95
<211> LENGTH: 30
<212> TYPE: PRT
<213> ORGANISM: Artificial Sequence
<220> FEATURE:
<223> OTHER INFORMATION: Human group 1 consensus framework H1

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 96
<211> LENGTH: 30
<212> TYPE: PRT
<213> ORGANISM: Artificial Sequence
<220> FEATURE:
<223> OTHER INFORMATION: hTNF40 framework H1

<400> SEQUENCE: 96

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Val Phe Thr
            20                  25                  30


<210> SEQ ID NO 97
<211> LENGTH: 14
```

<212> TYPE: PRT
<213> ORGANISM: Artificial Sequence
<220> FEATURE:
<223> OTHER INFORMATION: Human group 1 consensus framework H2

<400> SEQUENCE: 97

```
Trp Val Arg Gln Ala Pro Gly Gln Gly Leu Glu Trp Met Gly
1               5                   10
```

<210> SEQ ID NO 98
<211> LENGTH: 14
<212> TYPE: PRT
<213> ORGANISM: Artificial Sequence
<220> FEATURE:
<223> OTHER INFORMATION: hTNF40 framework H2

<400> SEQUENCE: 98

```
Trp Val Lys Gln Ala Pro Gly Lys Ala Phe Lys Trp Met Gly
1               5                   10
```

<210> SEQ ID NO 99
<211> LENGTH: 32
<212> TYPE: PRT
<213> ORGANISM: Artificial Sequence
<220> FEATURE:
<223> OTHER INFORMATION: Human group 1 consensus framework H3

<400> SEQUENCE: 99

```
Arg Val Thr Ile Thr Arg Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 100
<211> LENGTH: 32
<212> TYPE: PRT
<213> ORGANISM: Artificial Sequence
<220> FEATURE:
<223> OTHER INFORMATION: hTNF40 framework H3

<400> SEQUENCE: 100

```
Arg Phe Ala Phe Ser Leu Glu Thr Ser Ala Ser Thr Ala Phe Leu Gln
1               5                   10                  15

Ile Asn Asn Leu Lys Asn Glu Asp Thr Ala Thr Tyr Phe Cys Ala Arg
            20                  25                  30
```

<210> SEQ ID NO 101
<211> LENGTH: 11
<212> TYPE: PRT
<213> ORGANISM: Artificial Sequence
<220> FEATURE:
<223> OTHER INFORMATION: Human group 1 consensus framework H4

<400> SEQUENCE: 101

```
Trp Gly Gln Gly Thr Leu Val Thr Val Ser Ser
1               5                   10
```

<210> SEQ ID NO 102
<211> LENGTH: 11
<212> TYPE: PRT
<213> ORGANISM: Artificial Sequence
<220> FEATURE:
<223> OTHER INFORMATION: hTNF40 framework H4

<400> SEQUENCE: 102

```
Trp Gly Gln Gly Thr Thr Leu Thr Val Ser Ser
1               5                   10
```

```
<210> SEQ ID NO 103
<211> LENGTH: 324
<212> TYPE: DNA
<213> ORGANISM: Murine
<220> FEATURE:
<221> NAME/KEY: CDS
<222> LOCATION: (1)..(324)
<223> OTHER INFORMATION:

<400> SEQUENCE: 103

gac att gtg atg acc cag tct caa aaa ttc atg tcc aca tca gta gga       48
Asp Ile Val Met Thr Gln Ser Gln Lys Phe Met Ser Thr Ser Val Gly
1               5                   10                  15

gac agg gtc agc gtc acc tgc aag gcc agt cag aat gtg ggt act aat       96
Asp Arg Val Ser Val Thr Cys Lys Ala Ser Gln Asn Val Gly Thr Asn
            20                  25                  30

gta gcc tgg tat caa cag aaa cca gga caa tct cct aaa gca ctg att      144
Val Ala Trp Tyr Gln Gln Lys Pro Gly Gln Ser Pro Lys Ala Leu Ile
        35                  40                  45

tac tcg gca tcc ttc cta tat agt gga gtc cct tat cgc ttc aca ggc      192
Tyr Ser Ala Ser Phe Leu Tyr Ser Gly Val Pro Tyr Arg Phe Thr Gly
    50                  55                  60

agt gga tct ggg aca gat ttc act ctc acc atc agc act gtg cag tct      240
Ser Gly Ser Gly Thr Asp Phe Thr Leu Thr Ile Ser Thr Val Gln Ser
65                  70                  75                  80

gaa gac ttg gca gag tat ttc tgt cag caa tat aac atc tat cct ctc      288
Glu Asp Leu Ala Glu Tyr Phe Cys Gln Gln Tyr Asn Ile Tyr Pro Leu
                85                  90                  95

acg ttc ggt gct ggg acc aag ctg gag ctg aaa cgt                      324
Thr Phe Gly Ala Gly Thr Lys Leu Glu Leu Lys Arg
            100                 105


<210> SEQ ID NO 104
<211> LENGTH: 108
<212> TYPE: PRT
<213> ORGANISM: Murine

<400> SEQUENCE: 104

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Phe Leu Tyr Ser Gly Val Pro Tyr Arg Phe Thr Gly
    50                  55                  60

Ser Gly Ser Gly Thr Asp Phe Thr Leu Thr Ile Ser Thr Val Gln Ser
65                  70                  75                  80

Glu Asp Leu Ala Glu Tyr Phe Cys Gln Gln Tyr Asn Ile Tyr Pro Leu
                85                  90                  95

Thr Phe Gly Ala Gly Thr Lys Leu Glu Leu Lys Arg
            100                 105


<210> SEQ ID NO 105
<211> LENGTH: 354
<212> TYPE: DNA
<213> ORGANISM: Artificial Sequence
<220> FEATURE:
<223> OTHER INFORMATION: hTNF40 heavy chain variable domain
<220> FEATURE:
<221> NAME/KEY: CDS
<222> LOCATION: (1)..(354)
```

<223> OTHER INFORMATION:

<400> SEQUENCE: 105

```
cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15

aca gtc aag atc tcc tgc aag gct tct gga tat gtt ttc aca gac tat       96
Thr Val Lys Ile Ser Cys Lys Ala Ser Gly Tyr Val Phe Thr Asp Tyr
            20                  25                  30

gga atg aat tgg gtg aag cag gct cca gga aag gct ttc aag tgg atg      144
Gly Met Asn Trp Val Lys Gln Ala Pro Gly Lys Ala Phe Lys Trp Met
        35                  40                  45

ggc tgg ata aac acc tac att gga gag cca ata tat gtt gat gac ttc      192
Gly Trp Ile Asn Thr Tyr Ile Gly Glu Pro Ile Tyr Val Asp Asp Phe
    50                  55                  60

aag gga cga ttt gcc ttc tct ttg gaa acc tct gcc agc act gcc ttt      240
Lys Gly Arg Phe Ala Phe Ser Leu Glu Thr Ser Ala Ser Thr Ala Phe
65                  70                  75                  80

ttg cag atc aac aac ctc aaa aat gag gac acg gct aca tat ttc tgt      288
Leu Gln Ile Asn Asn Leu Lys Asn Glu Asp Thr Ala Thr Tyr Phe Cys
                85                  90                  95

gca aga ggt tac cgg tcc tat gct atg gac tac tgg ggt caa gga acc      336
Ala Arg Gly Tyr Arg Ser Tyr Ala Met Asp Tyr Trp Gly Gln Gly Thr
            100                 105                 110

tca gtc acc gtc tct tca                                              354
Ser Val Thr Val Ser Ser
        115
```

<210> SEQ ID NO 106
<211> LENGTH: 118
<212> TYPE: PRT
<213> ORGANISM: Artificial Sequence
<220> FEATURE:
<223> OTHER INFORMATION: hTNF40 heavy chain variable domain

<400> SEQUENCE: 106

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Val Phe Thr Asp Tyr
            20                  25                  30

Gly Met Asn Trp Val Lys Gln Ala Pro Gly Lys Ala Phe Lys Trp Met
        35                  40                  45

Gly Trp Ile Asn Thr Tyr Ile Gly Glu Pro Ile Tyr Val Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Gly Tyr Arg Ser Tyr Ala Met Asp Tyr Trp Gly Gln Gly Thr
            100                 105                 110

Ser Val Thr Val Ser Ser
        115
```

<210> SEQ ID NO 107
<211> LENGTH: 84
<212> TYPE: DNA
<213> ORGANISM: Artificial Sequence
<220> FEATURE:
<223> OTHER INFORMATION: OmpA oligonucleotide adaptor
<220> FEATURE:
<221> NAME/KEY: CDS
<222> LOCATION: (29)..(67)

```
<223> OTHER INFORMATION:

<400> SEQUENCE: 107

tcgagttcta gataacgagg cgtaaaaa atg aaa aag aca gct atc gca att        52
                               Met Lys Lys Thr Ala Ile Ala Ile
                               1               5

gca gtg gcc ttg gct ctgacgtacg agtcagg                                84
Ala Val Ala Leu Ala
    10


<210> SEQ ID NO 108
<211> LENGTH: 13
<212> TYPE: PRT
<213> ORGANISM: Artificial Sequence
<220> FEATURE:
<223> OTHER INFORMATION: OmpA oligonucleotide adaptor

<400> SEQUENCE: 108

Met Lys Lys Thr Ala Ile Ala Ile Ala Val Ala Leu Ala
1               5                   10


<210> SEQ ID NO 109
<211> LENGTH: 67
<212> TYPE: DNA
<213> ORGANISM: Artificial Sequence
<220> FEATURE:
<223> OTHER INFORMATION: IGS cassette-1
<220> FEATURE:
<221> NAME/KEY: CDS
<222> LOCATION: (2)..(40)
<223> OTHER INFORMATION:
<220> FEATURE:
<221> NAME/KEY: CDS
<222> LOCATION: (43)..(66)
<223> OTHER INFORMATION:

<400> SEQUENCE: 109

g agc tca cca gta aca aaa agt ttt aat aga gga gag tgt ta atg aag      48
  Ser Ser Pro Val Thr Lys Ser Phe Asn Arg Gly Glu Cys    Met Lys
  1               5                   10                     15

aag act gct ata gca att g                                             67
Lys Thr Ala Ile Ala Ile
                20


<210> SEQ ID NO 110
<211> LENGTH: 13
<212> TYPE: PRT
<213> ORGANISM: Artificial Sequence
<220> FEATURE:
<223> OTHER INFORMATION: IGS cassette-1

<400> SEQUENCE: 110

Ser Ser Pro Val Thr Lys Ser Phe Asn Arg Gly Glu Cys
1               5                   10


<210> SEQ ID NO 111
<211> LENGTH: 8
<212> TYPE: PRT
<213> ORGANISM: Artificial Sequence
<220> FEATURE:
<223> OTHER INFORMATION: IGS cassette-1

<400> SEQUENCE: 111

Met Lys Lys Thr Ala Ile Ala Ile
1               5


<210> SEQ ID NO 112
<211> LENGTH: 69
```

```
<212> TYPE: DNA
<213> ORGANISM: Artificial Sequence
<220> FEATURE:
<223> OTHER INFORMATION: IGS cassette-2
<220> FEATURE:
<221> NAME/KEY: CDS
<222> LOCATION: (2)..(43)
<223> OTHER INFORMATION:
<220> FEATURE:
<221> NAME/KEY: CDS
<222> LOCATION: (45)..(68)
<223> OTHER INFORMATION:

<400> SEQUENCE: 112

g agc tca cca gta aca aaa agt ttt aat aga ggg gag tgt taa a atg       47
  Ser Ser Pro Val Thr Lys Ser Phe Asn Arg Gly Glu Cys       Met
  1               5                   10

aag aag act gct ata gca att g                                         69
Lys Lys Thr Ala Ile Ala Ile
15                  20


<210> SEQ ID NO 113
<211> LENGTH: 13
<212> TYPE: PRT
<213> ORGANISM: Artificial Sequence
<220> FEATURE:
<223> OTHER INFORMATION: IGS cassette-2

<400> SEQUENCE: 113

Ser Ser Pro Val Thr Lys Ser Phe Asn Arg Gly Glu Cys
1               5                   10


<210> SEQ ID NO 114
<211> LENGTH: 8
<212> TYPE: PRT
<213> ORGANISM: Artificial Sequence
<220> FEATURE:
<223> OTHER INFORMATION: IGS cassette-2

<400> SEQUENCE: 114

Met Lys Lys Thr Ala Ile Ala Ile
1               5


<210> SEQ ID NO 115
<211> LENGTH: 81
<212> TYPE: DNA
<213> ORGANISM: Artificial Sequence
<220> FEATURE:
<223> OTHER INFORMATION: IGS cassette-3
<220> FEATURE:
<221> NAME/KEY: CDS
<222> LOCATION: (2)..(43)
<223> OTHER INFORMATION:
<220> FEATURE:
<221> NAME/KEY: CDS
<222> LOCATION: (57)..(80)
<223> OTHER INFORMATION:

<400> SEQUENCE: 115

g agc tca cca gta aca aaa agc ttt aat aga gga gag tgt tga             43
  Ser Ser Pro Val Thr Lys Ser Phe Asn Arg Gly Glu Cys
  1               5                   10

ggaggaaaaa aaa atg aag aaa act gct ata gca att g                      81
               Met Lys Lys Thr Ala Ile Ala Ile
                   15                  20


<210> SEQ ID NO 116
<211> LENGTH: 13
<212> TYPE: PRT
<213> ORGANISM: Artificial Sequence
```

```
<220> FEATURE:
<223> OTHER INFORMATION: IGS cassette-3

<400> SEQUENCE: 116

Ser Ser Pro Val Thr Lys Ser Phe Asn Arg Gly Glu Cys
1               5                   10


<210> SEQ ID NO 117
<211> LENGTH: 8
<212> TYPE: PRT
<213> ORGANISM: Artificial Sequence
<220> FEATURE:
<223> OTHER INFORMATION: IGS cassette-3

<400> SEQUENCE: 117

Met Lys Lys Thr Ala Ile Ala Ile
1               5


<210> SEQ ID NO 118
<211> LENGTH: 81
<212> TYPE: DNA
<213> ORGANISM: Artificial Sequence
<220> FEATURE:
<223> OTHER INFORMATION: IGS cassette-4
<220> FEATURE:
<221> NAME/KEY: CDS
<222> LOCATION: (2)..(43)
<223> OTHER INFORMATION:
<220> FEATURE:
<221> NAME/KEY: CDS
<222> LOCATION: (57)..(80)
<223> OTHER INFORMATION:

<400> SEQUENCE: 118

g agc tca cca gta aca aaa agt ttt aat aga gga gag tgt tga            43
  Ser Ser Pro Val Thr Lys Ser Phe Asn Arg Gly Glu Cys
  1               5                   10

cgaggattat ata atg aag aaa act gct ata gca att g                     81
               Met Lys Lys Thr Ala Ile Ala Ile
                   15                  20


<210> SEQ ID NO 119
<211> LENGTH: 13
<212> TYPE: PRT
<213> ORGANISM: Artificial Sequence
<220> FEATURE:
<223> OTHER INFORMATION: IGS cassette-4

<400> SEQUENCE: 119

Ser Ser Pro Val Thr Lys Ser Phe Asn Arg Gly Glu Cys
1               5                   10


<210> SEQ ID NO 120
<211> LENGTH: 8
<212> TYPE: PRT
<213> ORGANISM: Artificial Sequence
<220> FEATURE:
<223> OTHER INFORMATION: IGS cassette-4

<400> SEQUENCE: 120

Met Lys Lys Thr Ala Ile Ala Ile
1               5


<210> SEQ ID NO 121
<211> LENGTH: 30
<212> TYPE: PRT
<213> ORGANISM: Artificial Sequence
<220> FEATURE:
<223> OTHER INFORMATION: Human group 3 consensus framework H1
```

<400> SEQUENCE: 121

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 122
<211> LENGTH: 14
<212> TYPE: PRT
<213> ORGANISM: Artificial Sequence
<220> FEATURE:
<223> OTHER INFORMATION: Human group 3 consensus framework H2

<400> SEQUENCE: 122

Trp Val Arg Gln Ala Pro Gly Lys Gly Leu Glu Trp Val Ser
1 5 10

<210> SEQ ID NO 123
<211> LENGTH: 32
<212> TYPE: PRT
<213> ORGANISM: Artificial Sequence
<220> FEATURE:
<223> OTHER INFORMATION: Human group 3 consensus framework H3

<400> SEQUENCE: 123

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 124
<211> LENGTH: 11
<212> TYPE: PRT
<213> ORGANISM: Artificial Sequence
<220> FEATURE:
<223> OTHER INFORMATION: Human group 3 consensus framework H4

<400> SEQUENCE: 124

Trp Gly Gln Gly Thr Leu Val Thr Val Ser Ser
1 5 10

<210> SEQ ID NO 125
<211> LENGTH: 648
<212> TYPE: DNA
<213> ORGANISM: Artificial Sequence
<220> FEATURE:
<223> OTHER INFORMATION: Grafted heavy chain for fab

<400> SEQUENCE: 125
gaggttcagc tggtcgagtc aggaggcggt ctcgtgcagc ctggcggatc actgagattg 60
tcctgtgctg catctggtta cgtcttcaca gactatggaa tgaattgggt tagacaggcc 120
ccgggaaagg gcctggaatg gatgggttgg attaatactt acattggaga gcctatttat 180
gctgacagcg tcaagggcag attcacgttc tctctagaca catccaagtc aacagcatac 240
ctccaaatga atagcctgag agcagaggac accgcagtgt actattgtgc tagaggatac 300
agatcttatg ccatggacta ctggggccag ggtaccctag tcacagtctc ctcagcttcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600

```
tgcaacgtga atcacaagcc cagcaacacc aaggtcgaca agaaagtt               648


<210> SEQ ID NO 126
<211> LENGTH: 216
<212> TYPE: PRT
<213> ORGANISM: Artificial Sequence
<220> FEATURE:
<223> OTHER INFORMATION: Grafted heavy chain for fab

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val
    210                 215


<210> SEQ ID NO 127
<211> LENGTH: 642
<212> TYPE: DNA
<213> ORGANISM: Artificial Sequence
<220> FEATURE:
<223> OTHER INFORMATION: Grafted light chain for fab and modified fab

<400> SEQUENCE: 127

gacattcaaa tgacccagag cccatccagc ctgagcgcat ctgtaggaga ccgggtcacc     60

atcacttgta aagccagtca gaacgtaggt actaacgtag cctggtatca gcaaaaacca    120

ggtaaagccc caaaagccct catctacagt gcctctttcc tctatagtgg tgtaccatac    180

aggttcagcg gatccggtag tggtactgat ttcaccctca cgatcagtag cctccagcca    240

gaagatttcg ccacttatta ctgtcaacag tataacatct acccactcac attcggtcag    300

ggtactaaag tagaaatcaa acgtacggta gcggccccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480
```

```
gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcac cagtaacaaa aagctttaat agaggagagt gt                       642


<210> SEQ ID NO 128
<211> LENGTH: 214
<212> TYPE: PRT
<213> ORGANISM: Artificial Sequence
<220> FEATURE:
<223> OTHER INFORMATION: Grafted light chain for fab and modified fab

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 129
<211> LENGTH: 687
<212> TYPE: DNA
<213> ORGANISM: Artificial Sequence
<220> FEATURE:
<223> OTHER INFORMATION: Grafted heavy chain for modified fab

<400> SEQUENCE: 129

gaggttcagc tggtcgagtc aggaggcggt ctcgtgcagc ctggcggatc actgagattg     60

tcctgtgctg catctggtta cgtcttcaca gactatggaa tgaattgggt tagacaggcc    120

ccgggaaagg gcctggaatg gatgggttgg attaatactt acattggaga gcctatttat    180

gctgacagcg tcaagggcag attcacgttc tctctagaca catccaagtc aacagcatac    240

ctccaaatga atagcctgag agcagaggac accgcagtgt actattgtgc tagaggatac    300

agatcttatg ccatggacta ctggggccag ggtaccctag tcacagtctc ctcagcttcc    360
```

```
accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtcgaca agaaagttga gcccaaatct    660

tgtgacaaaa ctcacacatg cgccgcg                                        687


<210> SEQ ID NO 130
<211> LENGTH: 229
<212> TYPE: PRT
<213> ORGANISM: Artificial Sequence
<220> FEATURE:
<223> OTHER INFORMATION: Grafted heavy chain for modified fab

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```

ANTIBODY MOLECULES SPECIFIC TO HUMAN TUMOUR NECROSIS FACTOR ALPHA

CROSS-REFERENCE TO RELATED APPLICATIONS

This application is a Continuation of application Ser. No. 11/374,231 filed Mar. 13, 2006 now U.S. Pat. No. 7,402,662 which is a Continuation of application Ser. No. 09/949,559, filed Sep. 10, 2001, now U.S. Pat. No. 7,186,820, issued Mar. 6, 2007, which is a Continuation of application Ser. No. 09/875,221, filed Jun. 6, 2001, now U.S. Pat. No. 7,012,135, issued Mar. 14, 2006, and claims priority under 35 U.S.C. §119(a) to United Kingdom Patent Application 0013810.7, filed Jun. 6, 2000, which are incorporated in their entirety by reference herein.

FIELD OF THE INVENTION

The present invention relates to humanized antibody molecules specific to human TNFα, to processes for their production using recombinant DNA technology, and to their therapeutic uses.

BACKGROUND OF THE INVENTION

The present invention relates to an antibody molecule having specificity for antigenic determinants of human tumour necrosis factor alpha (TNFα). The present invention also relates to the therapeutic uses of the antibody molecule and methods for producing the antibody molecule.

This invention relates to antibody molecules. In an antibody molecule, there are two heavy chains and two light chains. Each heavy chain and each light chain has at its N-terminal end a variable domain. Each variable domain is composed of four framework regions (FRs) alternating with three complementarily determining regions (CDRs). The residues in the variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDRH1), residues 50-65 (CDRH2) and residues 95-102 (CDRH3)) according to the Kabat numbering.

The CDRs of the light chain variable domain are located at residues 24-34 (CDRL1), residues 50-56 (CDRL2) and residues 89-97 (CDRL3) according to the Kabat numbering.

Construction of CDR-grafted antibodies is described in European Patent Application EP-A-0239400, which discloses a process in which the CDRs of a mouse monoclonal antibody are grafted onto the framework regions of the variable domains of a human immunoglobulin by site directed mutagenesis using long oligonucleotides. The CDRs determine the antigen binding specificity of antibodies and are relatively short peptide sequences carried on the framework regions of the variable domains.

The earliest work on humanising monoclonal antibodies by CDR-grafting was carried out on monoclonal antibodies recognizing synthetic antigens, such as NP. However, examples in which a mouse monoclonal antibody recognizing lysozyme and a rat monoclonal antibody recognizing an antigen on human T-cells were humanised by CDR-grafting have been described by Verhoeyen et al. (Science, 239, 1534-1536, 1988) and Riechmann et al. (Nature, 332, 323-324, 1988), respectively.

Riechmann et al., found that the transfer of the CDRs alone (as defined by Kabat (Kabat et al. (supra) and Wu et al., J. Exp. Med., 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application WO 90/07861.

A number of reviews discussing CDR-grafted antibodies have been published, including Vaughan et al. (Nature Biotechnology, 16, 535 539, 1998).

TNFα is a pro-inflammatory cytokine that is released by and interacts with cells of the immune system. Thus, TNFα is released by macrophages that have been activated by lipopolysaccharides (LPS) of gram negative bacteria. As such, TNFα appears to be an endogenous mediator of central importance involved in the development and pathogenesis of endotoxic shock associated with bacterial sepsis. TNFα has also been shown to be up-regulated in a number of human diseases, including chronic diseases such as rheumatoid arthritis, Crohn's disease, ulcerative colitis and multiple sclerosis. Mice transgenic for human TNFα produce high levels of TNFα constitutively and develop a spontaneous, destructive polyarthritis resembling rheumatoid arthritis (Kaffer et al., EMBO J., 10, 4025 4031, 1991). TNFα is therefore referred to as a pro-inflammatory cytokine.

Monoclonal antibodies against TNFα have been described in the prior art. Meager et al., (Hybridoma, 6, 305-311, 1987) describe murine monoclonal antibodies against recombinant TNFα Fendly et al., (Hybridoma, 6, 359-370, 1987) describe the use of murine monoclonal antibodies against recombinant TNFα in defining neutralizing epitopes on TNF. Shimamoto et al., (Immunology Letters, 17, 311-318, 1988) describe the use of murine monoclonal antibodies against TNFγ and their use in preventing endotoxic shock in mice. Furthermore, in International Patent Application WO 92/11383, rccombinant antibodies, including CDR-grafted antibodies, specific for TNFα are disclosed. Rankin et al., (British J. Rheumatology, 34, 334-342, 1995) describe the use of such CDR-grafted antibodies in the treatment of rheumatoid arthritis. U.S. Pat. No. 5,919,452 discloses anti-TNF chimeric antibodies and their use in treating pathologies associated with the presence of TNF.

Antibodies to TNFα have been proposed for the prophylaxis and treatment of endotoxic shock (Beutler et al., Science, 234, 470-474, 1985). Bodmer et al., (Critical Care Medicine, 21, S441-S446, 1993) and Wherry et al., (Critical Care Medicine, 21, S436-S440, 1993) discuss the therapeutic potential of anti-TNFα antibodies in the treatment of septic shock. The use of anti-TNFα antibodies in the treatment of septic shock is also discussed by Kirschenbaum et al., (Critical Care Medicine, 26, 1625-1626, 1998). Collagen-induced arthritis can be treated effectively using an anti-TNFα monoclonal antibody (Williams et al. (PNAS—USA, 89, 9784-9788, 1992)).

Increased levels of TNFα are found in both the synovial fluid and peripheral blood of patients suffering from rheumatoid arthritis. When TNFα blocking agents are administered to patients suffering from rheumatoid arthritis, they reduce inflammation, improve symptoms and retard joint damage (McKown et al. (Arthritis Rheum., 42, 1204-1208, 1999).

The use of anti-TNFα antibodies in the treatment of rheumatoid arthritis and Crohn's disease is discussed in Feldman et al., (Transplantation Proceedings, 30, 4126-4127, 1998), Adorini et al., (Trends in Immunology Today, 18, 209-211, 1997) and in Feldman et al., (Advances in Immunology, 64, 283-350, 1997). The antibodies to TNFα used in such treatments are generally chimeric antibodies, such as those described in U.S. Pat. No. 5,919,452.

Two TNFα blocking products are currently licensed for the treatment of rheumatoid arthritis. The first, called etanercept, is marketed by Immunex Corporation as ENBREL. It is a recombinant fusion protein comprising two p75 soluble TNF-receptor domains linked to the Fc portion of a human immunoglobulin. The second, called infliximab, is marketed by Centocor Corporation as REMICADE. It is a chimeric antibody having murine anti-TNFα variable domains and human IgG1 constant domains.

The prior art recombinant anti-TNFα antibody molecules generally have a reduced affinity for TNFα compared to the antibodies from which the variable regions or CDRs are derived, generally have to be produced in mammalian cells and are expensive to manufacture. Prior art anti-TNFα antibodies are described in Stephens et al., (Immunology, 85, 668-674, 1995), GB-A-2 246 570 and GB A-2 297 145.

There is a need for an antibody molecule to treat chronic inflammatory diseases which can be used repeatedly and produced easily and efficiently. There is also a need for an antibody molecule which has high affinity for TNFα and low immunogenicity in humans.

SUMMARY OF THE INVENTION

In a first aspect, the present invention provides an antibody molecule having specificity for TNFα, comprising a heavy chain wherein the variable domain comprises a CDR (as defined by Kabat et al., (supra)) having the sequence given as H1 in FIG. 3 (SEQ ID NO:1) for CDRH1, as H2' in FIG. 3 (SEQ ID NO:2) or as H2 in FIG. 3 (SEQ ID NO:7) for CDRH2 or as H3 in FIG. 3 (SEQ ID NO:3) for CDRH3.

The antibody molecule of the first aspect of the present invention comprises at least one CDR selected from H1, H2' or H2 and H3 (SEQ ID NO:1; SEQ ID NO:2 or SEQ ID NO:7 and SEQ ID NO:3) for the heavy chain variable domain. Preferably, the antibody molecule comprises at least two and more preferably all three CDRs in the heavy chain variable domain.

In a second aspect of the present invention, there is provided an antibody molecule having specificity for human TNFα, comprising a light chain wherein the variable domain comprises a CDR (as defined by Kabat et al., (supra)) having the sequence given as L1 in FIG. 3 (SEQ ID NO:4) for CDRL1, L2 in FIG. 3 (SEQ ID NO:5) for CDRL2 or L3 in FIG. 3 (SEQ ID NO:6) for CDRL3.

The antibody molecule of the second aspect of the present invention comprises at least one CDR selected from L1, L2 and L3 (SEQ ID NO:4 to SEQ ID NO:6) for the light chain variable domain. Preferably, the antibody molecule comprises at least two and more preferably all three CDRs in the light chain variable domain.

The antibody molecules of the first and second aspects of the present invention preferably have a complementary light chain or a complementary heavy chain, respectively.

Preferably, the antibody molecule of the first or second aspect of the present invention comprises a heavy chain wherein the variable domain comprises a CDR (as defined by Kabat et al., (supra)) having the sequence given as H1 in FIG. 3 (SEQ ID NO:1) for CDRH1, as H2' or H2 in FIG. 3 (SEQ ID NO:2 or SEQ ID NO:7) for CDRH2 or as H3 in FIG. 3 (SEQ ID NO:3) for CDRH3 and a light chain wherein the variable domain comprises a CDR (as defined by Kabat et al., (supra)) having the sequence given as L1 in FIG. 3 (SEQ ID NO:4) for CDRL1, as L2 in FIG. 3 (SEQ ID NO:5) for CDRL2 or as L3 in FIG. 3 (SEQ ID NO:6) for CDRL3.

BRIEF DESCRIPTION OF THE DRAWINGS

FIG. 1 shows the framework regions of the human light chain subgroup 1 compared to the framework regions of the hTNF40 light chain (SEQ ID NOS:87 to 94).

FIG. 2 shows the framework regions of the human heavy chain subgroup and subgroup 3 compared to the framework regions of the hTNF40 heavy chain (SEQ ID NOS:95 to 102 and 121, 96, 122, 98, 123, 100, 124, and 102).

FIG. 3 shows the amino acid sequence of the CDRs of hTNF40 (SEQ ID NOS:1 to 7), wherein CDR H2' is a hybrid CDR wherein the C-terminal six amino acids are from the H2 CDR sequence of a human subgroup 3 germline antibody and the amino acid changes to the sequence resulting from this hybridisation are underlined.

FIG. 6 shows the nucleotide and predicted amino acid sequence of the murine hTNF40Vl (SEQ ID NOS:103 and 104).

FIG. 7 shows the nucleotide and predicted amino acid sequence of the murine hTNF40Vh (SEQ ID NOS: 5 105 AND 106).

FIG. 8 shows the nucleotide and predicted amino acid sequence of hTNF40-gL1 (SEQ ID NOS:8 AND 9).

FIG. 9 shows the nucleotide and predicted amino acid sequence of hTNF40-gL2 (SEQ ID NOS:10 AND 11).

FIG. 10 shows the nucleotide and predicted amino acid sequence of gh1hTNF40.4 (SEQ ID NO:12).

FIG. 11 shows the nucleotide and predicted amino acid sequence of gh3hTNF40.4 (SEQ ID NOS:14 and 15).

FIG. 15 shows the sequence of the OmpA oligonucleotide adapter (SEQ ID NO:107). Internal restriction sites are shown in bold. The 5' XhoI cohesive end ligates into the vector SalI site, blocking it. S.D. represents the OmpA Shine Dalgarno sequence.

FIG. 20 shows the oligonucleotide cassettes encoding different intergenic sequences for *E. coli* modified Fab expression (SEQ ID NOS: 109-120).

FIG. 21 shows periplasmic modified Fab accumulation of IGS variants.

DETAILED DESCRIPTION OF THE INVENTION

Figure 4:
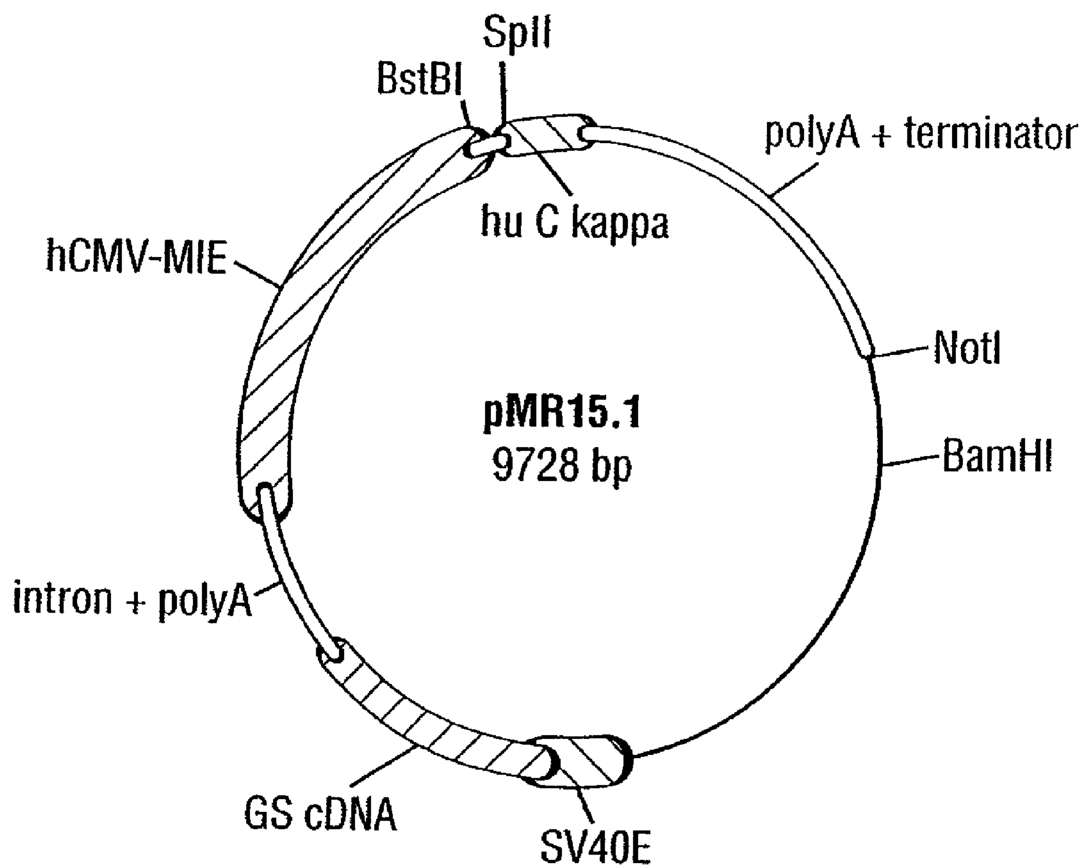
FIG. 4 shows vector pMR15.1.

The CDRs given in SEQ IDS NOS:1 and 3 to 7 and in FIG. 3 referred to above are derived from a mouse monoclonal antibody hTNF40. However, SEQ ID NO:2 consists of a hybrid CDR. The hybrid CDR comprises part of heavy chain CDR2 from mouse monoclonal antibody hTNF40 (SEQ ID NO:7) and part of heavy chain CDR2 from a human group 3 germline V region sequence.

The complete sequences of the variable domains of the mouse hTNF40 antibody are shown in FIG. 6 (light chain) (SEQ ID NO:103) and FIG. 7 (heavy chain) (SEQ ID NO:105). This mouse antibody is referred to below as "the donor antibody."

A first alternatively preferred embodiment of the first or second aspect of the present invention is the mouse monoclonal antibody hTNF40 having the light and heavy chain variable domain sequences shown in FIG. 6 (SEQ ID NO:103) and FIG. 7 (SEQ ID NO:105), respectively. The light chain constant region of hTNF40 is kappa and the heavy chain constant region is IgG2a.

In a second alternatively preferred embodiment, the antibody according to either of the first and second aspects of the present invention is a chimeric mouse/human antibody molecule, referred to herein as the chimeric hTNF40 antibody molecule. The chimeric antibody molecule comprises the variable domains of the mouse monoclonal antibody hTNF40 (SEQ ID NOS:103 and 105) and human constant domains. Preferably, the chimeric hTNF40 antibody molecule comprises the human C kappa domain (Hieter et al., Cell, 22, 197-207, 1980; Genbank accession number J00241) in the light chain and the human gamma 4 domains (Flanagan et al., Nature, 300, 709-713, 1982) in the heavy chain.

In a third alternatively preferred embodiment, the antibody according to either of the first and second aspects of the present invention is a CDR-grafted antibody molecule. The term "a CDR-grafted antibody molecule" as used herein refers to an antibody molecule wherein the heavy and/or light chain contains one or more CDRs (including, if desired, a hybrid CDR) from the donor antibody (e.g., a murine monoclonal antibody) grafted into a heavy and/or light chain variable region framework of an acceptor antibody (e.g., a human antibody).

Preferably, such a CDR-grafted antibody has a variable domain comprising human acceptor framework regions as well as one or more of the donor CDRs referred to above.

When the CDRs are grafted, any appropriate acceptor variable region framework sequence may be used having regard to the class/type of the donor antibody from which the CDRs are derived, including mouse, primate and human framework regions. Examples of human frameworks which can be used in the present invention are KOL, NEWM, REI, EU, TUR, TEI, LAY and POM (Kabat et al. (supra)). For example, KOL and NEWM can be used for the heavy chain, REI can be used for the light chain and EU, LAY and POM can be used for both the heavy chain and the light chain. The preferred framework regions for the light chain are the human group 1 framework regions shown in FIG. 1 (SEQ ID NOS:87, 89, 91 and 93). The preferred framework regions for the heavy chain are the human group 1 and group 3 framework regions shown in FIG. 2 (SEQ ID NOS:95, 97, 99 and 101 and SEQ ID NOS: 121, 122, 123, and 124), respectively.

In a CDR-grafted antibody of the present invention, it is preferred to use as the acceptor antibody one having chains which are homologous to the chains of the donor antibody. The acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody. Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has human group 1 framework regions (shown in FIG. 2) (SEQ ID NOS: 95, 97, 99 and 101), then the acceptor framework regions of the heavy chain comprise, in addition to one or more donor CDRs, donor residues at positions 28, 69 and 71 (according to Kabat et al. (supra)).

Alternatively, if the acceptor heavy chain has group 1 framework regions, then the acceptor framework regions of the heavy chain comprise, in addition to one or more donor CDRs, donor residues at positions 28, 38, 46, 67, 69 and 71 (according to Kabat et al. (supra).

Preferably, in a CDR-grafted antibody molecule of the present invention, if the acceptor heavy chain has human group 3 framework regions (shown in FIG. 2) (SEQ ID NOS: 121, 122, 123 and 124), then the acceptor framework regions of the heavy chain comprise, in addition to one or more donor CDRs, donor residues at positions 27, 28, 30, 48, 49, 69, 71, 73, 76 and 78 (according to Kabat et al. (supra)).

Preferably, in a CDR-grafted antibody molecule according to the present invention, if the acceptor light chain has human group 1 framework regions (shown in FIG. 1) (SEQ ID NOS: 87, 89, 91 and 93) then the acceptor framework regions of the light chain comprise donor residues at positions 46 and 60 (according to Kabat et al. (supra)).

Donor residues are residues from the donor antibody, i.e., the antibody from which the CDRs were originally derived.

The antibody molecule of the present invention may comprise: a complete antibody molecule, having full length heavy and light chains; a fragment thereof, such as a Fab, modified Fab, Fab', $F(ab')_2$ or Fv fragment; a light chain or heavy chain monomer or dimer; a single chain antibody, e.g., a single chain Fv in which the heavy and light chain variable domains are joined by a peptide linker. Similarly, the heavy and light chain variable regions may be combined with other antibody domains as appropriate.

Preferably the antibody molecule of the present invention is a Fab fragment. Preferably the Fab fragment has a heavy chain having the sequence given as SEQ ID NO:126 and a light chain having the sequence given as SEQ ID NO:128. The amino acid sequences given in SEQ ID NO:126 and SEQ ID NO:128 are preferably encoded by the nucleotide sequences given in SEQ ID NO:125 and SEQ ID NO:127, respectively.

Alternatively, it is preferred that the antibody molecule of the present invention is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residue to which the effector or reporter molecule may be attached. Such a modified Fab fragment preferably has a heavy chain having the sequence given as SEQ ID NO:130 and the light chain having the sequence given as SEQ ID NO:128. The amino acid sequence given in SEQ ID NO:130 is preferably encoded by the nucleotide sequence given in SEQ ID NO:129.

A preferred effector group is a polymer molecule, which may be attached to the modified Fab fragment to increase its half-life in vivo.

The polymer molecule may, in general, be a synthetic or a naturally occurring polymer, for example, an optionally substituted straight or branched chain polyalkylene, polyalkenylene or polyoxyalkylene polymer or a branched or unbranched polysaccharide, e.g., a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly (ethyleneglycol) or derivatives thereof. Particular naturally occurring polymers include lactose, amylose, dextran, glycogen or derivatives thereof. “Derivatives” as used herein is intended to include reactive derivatives, for example, thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500_Da to 50000_Da, preferably from 5000 to 40000_Da and more preferably from 25000 to 40000_Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000_Da. For applications where the product remains in the circulation, it may be advantageous to use a higher molecular weight polymer, for example having a molecular weight in the range from 25000_Da to 40000_Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000_Da to about 40000_Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example, any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g., iodoacetamide, an imide, e.g., maleimide, a vinyl sulphone or a disulphide. Such starting materials may be obtained commercially (for example, from Shearwater Polymers Inc., Huntsville, Ala., USA) or may be prepared from commercially available starting materials using conventional chemical procedures.

As regards attaching poly(ethyleneglycol) (PEG) moieties, reference is made to “Poly(ethyleneglycol) Chemistry, Biotechnical and Biomedical Applications,” 1992, J. Milton Harris (ed), Plenum Press, New York, “Poly(ethyleneglycol) Chemistry and Biological Applications,” 1997, J. Milton Harris and S. Zalipsky (eds), American Chemical Society, Washington D.C. and “Bioconjugation Protein Coupling Techniques for the Biomedical Sciences,” 1998, M. Aslam and A. Dent, Grove Publishers, New York.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/06231, WO 92/22583, WO 89/00195 and WO 89/01476. Alternatively, where the effector or reporter molecule is a protein or polypeptide the linkage may be achieved using recombinant DNA procedures, for example, as described in WO 86/01533 and EP-A-0392745.

Figure 13:
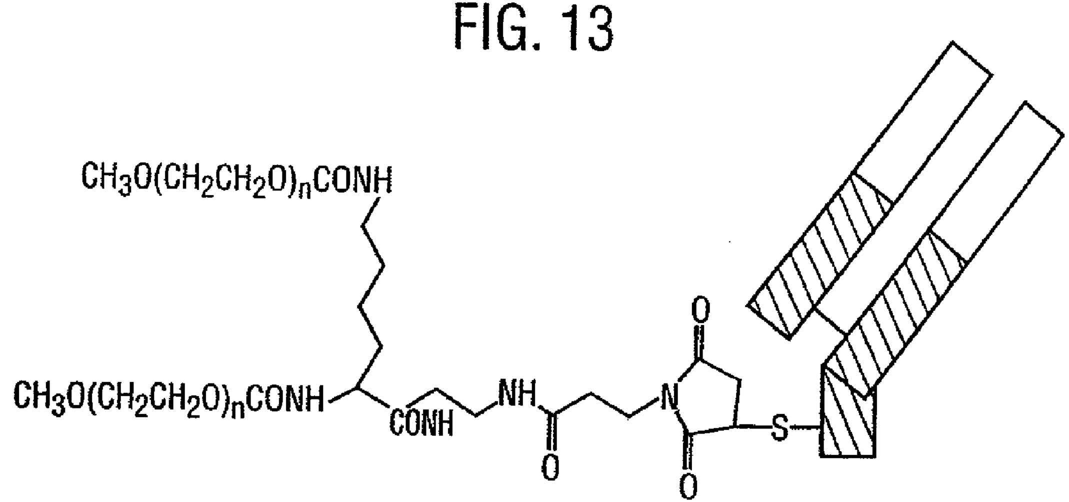
FIG. 13 shows the structure of a compound called CDP870 comprising a modified Fab fragment derived from antibody hTNF40 covalently linked via a cysteine residue to a lysyl-maleimide linker wherein each amino group on the lysyl residue has covalently attached to it a methoxy PEG residue wherein n is about 420.

Preferably, the modified Fab fragment of the present invention is PEGylated (i.e., has PEG (poly(ethyleneglycol)) covalently attached thereto) according to the method disclosed in EP-A-0948544. Preferably the antibody molecule of the present invention is a PEGylated modified Fab fragment as shown in FIG. 13. As shown in FIG. 13, the modified Fab fragment has a maleimide group covalently linked to a single thiol group in a modified hinge region. A lysine residue is covalently linked to the maleimide group. To each of the amine groups on the lysine residue is attached a methoxypoly (ethyleneglycol) polymer having a molecular weight of approximately 20,000 Da. The total molecular weight of the entire effector molecule is therefore approximately 40,000 Da.

Preferably, in the compound shown in FIG. 13, the heavy chain of the antibody part has the sequence given as SEQ ID NO:130 and the light chain has the sequence given in SEQ ID NO:128. This compound is referred to herein as CDP870.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g., for simply blocking TNFα activity.

Also, the antibody molecule of the present invention may have an effector or a reporter molecule attached to it. For instance, it may have a macrocycle, for chelating a heavy metal atom, or a toxin, such as ricin, attached to it by a covalent bridging structure. Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has (have) been replaced by, or has attached thereto by peptide linkage, a functional non-immunoglobulin protein, such as an enzyme or toxin molecule.

The antibody molecule of the present invention preferably has a binding affinity of at least $0.85\times10^{-10}$ M, more preferably at least $0.75\times10^{-10}$ M and most preferably at least $0.5\times10^{-10}$ M. (It is worth noting that the preferred humanised antibody molecule of the present invention, as, described below, has an affinity of about $0.5\times10^{-10}$ M, which is better than the affinity of the murine monoclonal antibody from which it is derived. The murine antibody has an affinity of about $0.85\times10^{-10}$M.)

Preferably, the antibody molecule of the present invention comprises the light chain variable domain hTNF40-gLI (SEQ ID NO:8) and the heavy chain variable domain gh3hTNF40.4 (SEQ ID NO:15). The sequences of the variable domains of these light and heavy chains are shown in FIGS. 8 and 11, respectively.

The present invention also relates to variants of the antibody molecule of the present invention, which have an improved affinity for TNFα. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides a DNA sequence encoding the heavy and/or light chain(s) of the antibody molecule of the present invention.

Preferably, the DNA sequence encodes the heavy or the light chain of the antibody molecule of the present invention.

In one preferred embodiment, the DNA sequence encodes a light chain and comprises the sequence shown in SEQ ID NO:8 (hTNF40-gL1) or SEQ ID NO:10 (h-TNF-40-gL2) or a degenerate equivalent thereof.

In an alternatively preferred embodiment, the DNA sequence encodes a heavy chain and comprises the sequence shown in SEQ ID NO:12 (gh1hTNF40.4) or SEQ ID NO:14 (gh3hTNF40.4) or a degenerate equivalent thereof.

The DNA sequence of the present invention may comprise synthetic DNA, for instance produced by chemical processing, cDNA, genomic DNA or any combination thereof.

The present invention also relates to a cloning or expression vector comprising one or more DNA sequences of the present invention. Preferably, the cloning or expression vector comprises two DNA sequences, encoding the light chain and the heavy chain of the antibody molecule of the present invention, respectively.

In a preferred embodiment, the present invention provides an *E. coli* expression vector comprising a DNA sequence of the present invention. Preferably the expression vector is pTTO(CDP870) as shown schematically in FIG. 22.

Figure 19:
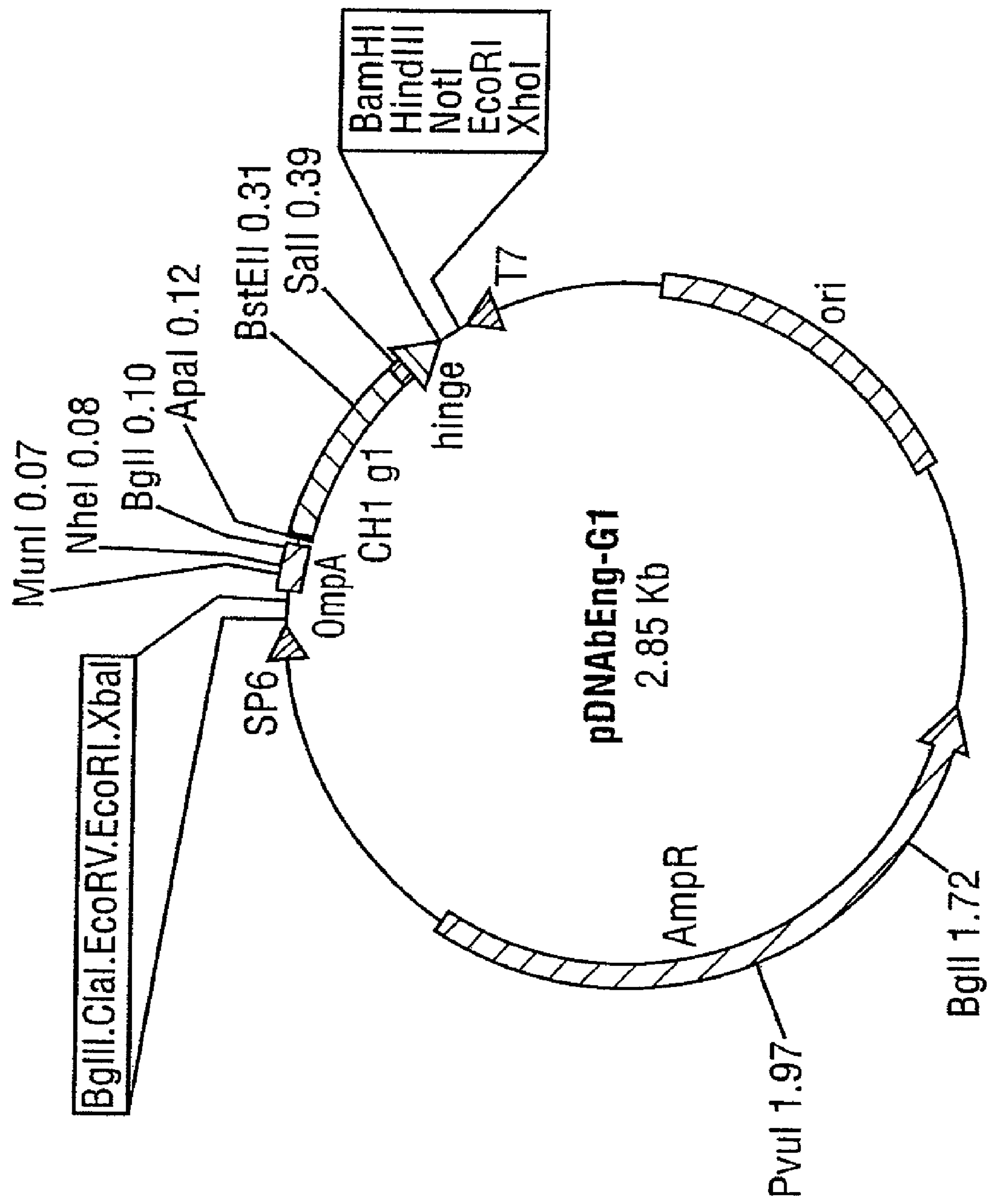
FIG. 19 shows vector pDNAbEng-G1.

The present invention also comprises vector pDNAbEng-G1 as shown in FIG. 19.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

DNA sequences which encode the antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecule of the present invention. Bacterial, for example, *E. coli*, and other microbial systems may be used, in part, for expression of antibody fragments such as Fab and $F(ab')_2$ fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include CHO, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule.

Preferably the process for the production of the antibody molecule of the present invention comprises culturing *E. coli* comprising an *E. coli* expression vector comprising the DNA sequence of the present invention under conditions suitable for leading to expression of protein from the DNA sequence and isolating the antibody molecule. The antibody molecule may be secreted from the cell or targeted to the periplasm by suitable signal sequences. Alternatively, the antibody molecules may accumulate within the cell's cytoplasm. Preferably the antibody molecule is targeted to the periplasm. Depending on the antibody molecule being produced and the process used, it is desirable to allow the antibody molecules to refold and adopt a functional conformation. Procedures for allowing antibody molecules to refold are well known to those skilled in the art.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The present invention also provides a therapeutic or diagnostic composition comprising an antibody molecule of the present invention in combination with a pharmaceutically acceptable excipient, diluent or carrier.

The present invention also provides a process for preparation of a therapeutic or diagnostic composition comprising admixing the antibody molecule of the present invention together with a pharmaceutically acceptable excipient, diluent or carrier.

The antibody molecule may be the sole active ingredient in the therapeutic or diagnostic composition or may be accompanied by other active ingredients including other antibody ingredients, for example, anti-T cell, anti-IFNγ or anti-LPS antibodies, or non-antibody ingredients such as xanthines.

The pharmaceutical compositions should preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, an effective dose will be from 0.0 1 mg/kg to 50 mg/kg, preferably 0.1 mg/kg to 20 mg/kg, more preferably about 15 mg/kg. As shown in the Examples below, doses of 1, 5 and 20 mg/kg have been used to treat patients suffering, from rheumatoid arthritis.

Compositions may be administered individually to a patient or may be administered in combination with other agents, drugs or hormones.

The dose at which the antibody molecule of the present invention is administered depends on the nature of the condition to be treated, the degree to which the level of TNFα to be neutralised is, or is expected to be, raised above a desirable level, and on whether the antibody molecule is being used prophylactically or to treat an existing condition.

Thus, for example, where the product is for treatment or prophylaxis of a chronic inflammatory disease, such as rheumatoid arthritis, suitable doses of the antibody molecule of the present invention lie in the range of between 0.5 and 50 mg/kg, more preferably between 1 and 20 mg/kg and most preferably about 15 mg/kg. The frequency of dose will depend on the half-life of the antibody molecule and the duration of its effect.

If the antibody molecule has a short half-life (e.g., 2 to 10 hours) it may be necessary to give one or more doses per day. Alternatively, if the antibody molecule has a long half-life (e.g., 2 to 15 days) it may only be necessary to give a dosage once per day, per week or even once every 1 or 2 months.

A pharmaceutical composition may also contain a pharmaceutically acceptable carrier for administration of the antibody. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example, mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g., by injection or infusion, for example, by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intraarterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides the antibody molecule of the present invention for use in treating a disease mediated by TNFα.

The present invention further provides the use of the antibody molecule according to the present invention in the manufacture of a medicament for the treatment of a disease mediated by TNFα.

The antibody molecule of the present invention may be utilised in any therapy where it is desired to reduce the level of biologically active TNFα present in the human or animal body. The TNFα may be circulating in the body or present in an undesirably high level localised at a particular site in the body.

For example, elevated levels of TNFα are implicated in acute and chronic immune and immunoregulatory disorders, infections including septic, endotoxic and cardiovascular shock, inflammatory disorders, neurodegenerative diseases, malignant diseases and alcohol induced hepatitis. Details of the numerous disorders associated with elevated levels of TNFα are set out in U.S. Pat. No. 5,919,452. The antibody molecule of the present invention may be utilised in the therapy of diseases mediated by TNFα. Particularly relevant diseases which may be treated by the antibody molecule of the present invention include sepsis, congestive heart failure, septic or endotoxic shock, cachexia, adult respiratory distress syndrome, AIDS, allergies, psoriasis, TB, inflammatory bone disorders, blood coagulation disorders, burns, rejection episodes following organ or tissue transplant, Crohn's disease and autoimmune diseases, such as thyroiditis and rheumatoid- and osteo-arthritis.

Additionally, the antibody molecule or composition may be used: to reduce side effects associated with TNFα generation during neoplastic therapy; to eliminate or reduce shock-related symptoms associated with the treatment or prevention of graft rejection by use of an anti-lymphocyte antibody; or for treating multi-organ failure.

The antibody molecule of the present invention is preferably used for treatment of rheumatoid- or osteo-arthritis.

The present invention also provides a method of treating human or animal subjects suffering from or at risk of a disorder mediated by TNFα, the method comprising administering to the subject an effective amount of the antibody molecule of the present invention.

The antibody molecule of the present invention may also be used in diagnosis, for example, in the in vivo diagnosis and imaging of disease states involving elevated levels of TNFα.

The present invention also provides an antibody molecule comprising a hybrid CDR comprising a truncated donor CDR sequence wherein the missing portion of the truncated donor CDR is replaced by a different sequence and forms a functional CDR. The term "hybrid CDR" as used herein means a CDR comprising a donor CDR which has been truncated at one or more positions, for example, at one or both of its ends. The missing portion of the truncated donor CDR is replaced by a different sequence to form a complete and functional CDR. The hybrid CDR has at least one amino acid change compared to the complete donor CDR. The sequence replacing the truncated portion of the CDR can be any sequence. Preferably the non-donor part of the CDR sequence is from the antibody from which the framework regions of the antibody molecule are derived, such as a germline antibody sequence.

It has been found that antibody molecules comprising a hybrid CDR retain substantially the same binding affinity as an antibody molecule comprising complete donor CDRs. The term "substantially the same binding affinity" as used herein means at least 70%, more preferably at least 85% and most preferably at least 95% of the binding affinity of the corresponding antibody molecule comprising complete donor CDRs. As noted above, in certain cases, the affinity of the antibody of the invention may be greater than that of the donor antibody. The use of a hybrid CDR provides the advantages of reducing the amount of foreign (i.e., donor) sequence present in the antibody molecule and may increase the binding affinity of the antibody molecule compared to the corresponding antibody molecule comprising complete donor CDRs.

Any of the CDRs of the antibody molecule can be hybrid. Preferably CDR2 of the heavy chain is hybrid in the antibody molecule.

Preferably the truncation of the donor CDR is from 1 to 8 amino acids, more preferably from 4 to 6 amino acids. It is further preferred that the truncation is made at the C-terminus of the CDR.

Depending on the sequence of the truncated portion of the CDR and the sequence of the different sequence replacing the missing portion, a number of amino acid changes may be made. Preferably at least 2 amino acid changes are made, more preferably at least 3 amino acid changes are made and most preferably at least 4 amino acid changes are made.

A particular embodiment of this aspect of the invention is an antibody according to the first aspect of the invention wherein the second CDR in the heavy chain has the sequence given as SEQ ID NO:2. This has better affinity for its antigen than does the donor antibody from which part of the CDR is derived.

The present invention also provides a nucleic acid sequence which encodes the antibody molecule comprising a hybrid CDR of the present invention.

The present invention also provides an expression vector containing the nucleic acid sequence encoding the antibody molecule comprising a hybrid CDR of the present invention.

The present invention also provides a host cell transformed with the vector of the present invention.

The present invention also provides a process for the production of an antibody molecule comprising a hybrid CDR comprising culturing the host cell of the present invention and isolating the antibody molecule.

The present invention is further described by way of illustration only in the following examples which refer to the accompanying Figures, in which:

EXAMPLES

Gene Cloning and Expression of a Chimeric hTNF40 Antibody Molecule

RNA Preparation from hTNF40 Hybridoma Cells

Total RNA was prepared from $3\times10^7$ hTNF40 hybridoma cells as described below. Cells were washed in physiological saline and dissolved in RNAzol (0.2 ml per $10^6$ cells). Chloroform (0.2 ml per 2 ml homogenate) was added, the mixture shaken vigorously for 15 seconds and then left on ice for 15 minutes. The resulting aqueous and organic phases were separated by centrifugation for 15 minutes in an Eppendorf centrifuge and RNA was precipitated from the aqueous phase by the addition of an equal volume of isopropanol. After 15 minutes on ice, the RNA was pelleted by centrifugation, washed with 70% ethanol, dried and dissolved in sterile, RNAse free water. The yield of RNA was 400 µg.

PCR Cloning of hTNF40 Vh and V1 cDNA sequences coding for the variable domains of hTNF40 heavy and light chains were synthesised using reverse transcriptase to produce single stranded cDNA copies of the mRNA present in the total RNA, followed by Polymerase Chain Reaction (PCR) on the cDNAs with specific oligonucleotide primers.

a) cDNA Synthesis cDNA was synthesised in a 20 µl reaction volume containing the following reagents: 50 mM Tris-HCl pH 8.3, 75 mM KCl, 10 mM dithiothreitol, 3 mM $MgCl_2$, 0.5 mM each deoxyribonucleoside triphosphate, 20 units RNAsin, 75 ng random hexanucleotide primer, 2 µg hTNF40 RNA and 200 units Moloney Murine Leukemia Virus reverse transcriptase. After incubation at 42° C. for 60 minutes, the reaction was terminated by heating at 95° C. for 5 minutes.

b) PCR

Aliquots of the cDNA were subjected to PCR using combinations of primers specific for the heavy and light chains. The nucleotide sequences of the 5' primers for the heavy and light chains are shown in Tables 1 and 2 respectively. These sequences all contain, in order, a restriction site starting 7 nucleotides from their 5' ends, the sequence GCCGCCACC (SEQ ID. NO:16), to allow optimal translation of the resulting mRNAs, an initiation codon and 20-30 nucleotides based on the leader peptide sequences of known mouse antibodies (Kabat et al., Sequences of Proteins of Immunological Interest, 5$^{th}$ Edition, 1991, U.S. Department of Health and Human Services, Public Health Service, National Institutes of Health).

The 3' primers are shown in Table 3. The light chain primer spans the J-C junction of the antibody and contains a restriction site for the enzyme SplI to facilitate cloning of the VI PCR fragment. The heavy chain 3' primers are a mixture designed to span the J-C junction of the antibody. The 3' primer includes an ApaI restriction site to facilitate cloning. The 3' region of the primers contains a mixed sequence based on those found in known mouse antibodies (Kabat et al., 1991, supra).

The combinations of primers described above enable the PCR products for Vh and V1 to be cloned directly into an appropriate expression vector (see below) to produce chimeric (mouse-human) heavy and light chains and for these genes to be expressed in mammalian cells to produce chimeric antibodies of the desired isotype.

Incubations (100 µl) for the PCR were set up as follows. Each reaction contained 10 mM Tris-HCl pH 8.3, 1.5 mM $MgCl_2$, 50 mM KCl, 0.01% w/v gelatin, 0.25 mM each deoxyribonucleoside triphosphate, 10 pmoles 5' primer mix (Table 4), 10 pmoles 3' primer (CL12 (light chain) or R2155 (heavy chain) (Table 3)), 1 µl cDNA and 1 unit Taq polymerase. Reactions were incubated at 95° C. for 5 minutes and then cycled through 94° C. for 1 minute, 55° C. for 1 minute and 72° C. for 1 minute. After 30 cycles, aliquots of each reaction were analysed by electrophoresis on an agarose gel. Light chain reactions containing 5' primer mixes from light chain pools 1, 2 and 7 produced bands with sizes consistent with full length V1 fragments while the reaction from heavy chain reaction pool 3 produced a fragment with a size expected of a Vh gene. The band produced by the light chain pool 1 primers was not followed up as previous results had shown that this band corresponds to a light chain pseudogene produced by the hybridoma cell. The band produced by the light chain pool 7 primers was weaker than the band from the pool 2 primers and therefore was not followed up. Only the band from light chain reaction pool 2, which was the strongest band, was followed up.

c) Molecular Cloning of the PCR Fragments

The DNA fragments produced in the light chain reaction pool 2 were digested with the enzymes BstBI and SplI, concentrated by ethanol precipitation, electrophoresed on a 1.4% agarose gel and DNA bands in the range of 400 base pairs recovered. These were cloned by ligation into the vector pMR15.1 (FIG. 4) that had been restricted with BstBI and SplI. After ligation, mixtures were transformed into *E. coli* LM 1035 and plasmids from the resulting bacterial colonies screened for inserts by digestion with BstBI and SplI. Representatives with inserts from each ligation were analysed further by nucleotide sequencing.

Figure 5:
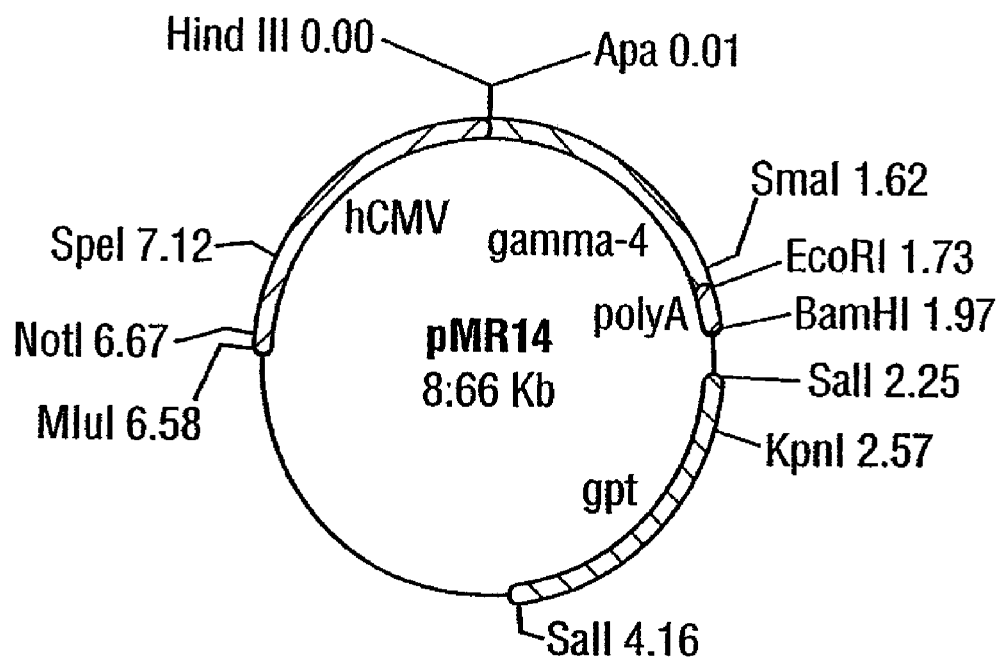
FIG. 5 shows vector pMR14.

In a similar manner, the DNA fragments produced in heavy chain reaction pool 3 were digested with HindIII and ApaI and cloned into the vector pMR14 (FIG. 5) that had been restricted with HindIII and ApaI. Again, representative plasmids containing inserts were analysed by nucleotide sequencing.

d) Nucleotide Sequence Analysis

Plasmid DNA from a number of isolates containing Vh inserts was sequenced using the primers R1053 (see Table 5) (which primes in the 3' region of the HCMV promoter in pMR14) and R720 (see Table 5) (which primes in the 5' region of human C-gamma 4 and allows sequencing through the DNA insert on pMR14). It was found that the nucleotide sequences of the Vh insert in a number of clones were identical, except for differences in the signal peptide and J regions. This indicated that the clones examined are independent isolates arising from the use of different primers from the mixture of oligonucleotides during the PCR stage. The determined nucleotide sequence and predicted amino acid sequence of the variable domain of the heavy chain of antibody hTNF40 (hTNF40Vh) are given in FIG. 7 (SEQ ID NO:105).

To analyse the light chain clones, the sequence derived from priming with RI053 (see Table 5) and R684 (SEQ ID NO:66) (which primes in the 5' region of human C-kappa and allows sequencing through the DNA insert on pMR15.1) was examined. The nucleotide sequence and predicted amino acid sequence of the VI genes arising from reactions in pool 2 were similarly analysed. Again it was found that the nucleotide sequences of the VI insert in a number of clones were identical, except for differences in the signal peptide and J regions, indicating that the clones examined were independent isolates arising from the use of different primers from the mixture of oligonucleotides used during the PCR stage. The determined nucleotide sequence and predicted amino acid sequence of the variable domain of the light chain of antibody hTNF40 (hTNF40VI) are given in FIG. 6 (SEQ ID NO:103).

TABLE I

Oligonucleotide primers for the 5' region of mouse heavy chains.

| | | |
|---|---|---|
| CH1: | 5'ATGAAATGCAGCTGGGTCAT(G,C)T TCTT3' | (SEQ ID NO: 17) |
| CH2: | 5'ATGGGATGGAGCT(A,G)TATCAT (C,G)(C,T)TCTT3' | (SEQ ID NO: 18) |

TABLE I-continued

| Oligonucleotide primers for the 5' region of mouse heavy chains. | | |
|---|---|---|
| CH3: | 5'ATGAAG(A,T)TGTGGTTAAACTGGG TTTT3' | (SEQ ID NO: 19) |
| CH4: | 5'ATG(G,A)ACTTTGGG(T,C)TCAGC TTG(G,A)T3' | (SEQ ID NO: 20) |
| CH5: | 5'ATGGACTCCAGGCTCAATTTAGTT TT3' | (SEQ ID NO: 21) |
| CH6: | 5'ATGGCTGTC(C,T)T(G,A)G (G,C)GCT(G,A)CTCTTCTG3' | (SEQ ID NO: 22) |
| CH7: | 5'ATGG(G,A)ATGGAGC(G,T)GG (G,A)TCTTT(A,C)TCTT3' | (SEQ ID NO: 23) |
| CH8: | 5'ATGAGAGTGCTGATTCTTTTGTG3' | (SEQ ID NO: 24) |
| CH9: | 5'ATGG(C,A)TTGGGTGTGGA(A,C) CTTGCTATT3' | (SEQ ID NO: 25) |
| CH10: | 5'ATGGGCAGACTTACATTCTCATTC CT3' | (SEQ ID NO: 26) |
| CH11: | 5'ATGGATTTTGGGCTGATTTTTTTTAT TG3' | (SEQ ID NO: 27) |
| CH12: | 5'ATGATGGTGTTAAGTCTTCTGTAC CT3' | (SEQ ID NO: 28) |

Each of the above primers has the sequence 5'GCGCGCAAGCTTGCCGCCACC3' (SEQ ID NO:29) added to its 5' end.

TABLE 2

| Oligonucleotide primers for the 5' region of mouse light chains. | | |
|---|---|---|
| CL1: | 5'ATGAAGTTGCCTGTTAGGCTGTTGGT GCT3' | (SEQ ID NO: 30) |
| CL2: | 5'ATGGAG(T,A)CAGACACACTCCTG (T,C)TATGGGT3' | (SEQ ID NO: 31) |
| CL3: | 5'ATGAGTGTGCTCACTCAGGTCCT3' | (SEQ ID NO: 32) |
| CL4: | 5'ATGAGG(G,A)CCCCTGCTCAG (A,T)TT(C,T)TTGG3' | (SEQ ID NO: 33) |
| CL5: | 5'ATGGATTT(T,A)CAGGTGCAGATT (T,A)TCAGCTT3' | (SEQ ID NO: 34) |
| CL5A: | 5'ATGGATTT(T,A)CA(A,G)GTGCAG ATT(T,A)TCAGCTT3' | (SEQ ID NO: 35) |
| CL6: | 5'ATGAGGT(T,G)C(T,C)(T,C)TG (T,C)T(G,C)AG(T,C)T(T,C)CTG (A,G)G3' | (SEQ ID NO: 36) |
| CL7: | 5'ATGGGC(T,A)TCAAGATGGAGTCAC A3' | (SEQ ID NO: 37) |
| CL8: | 5'ATGTGGGGA(T,C)CT(G,T)TTT (T,C)C(A,C)(A,C)TTTTTCAAT3' | (SEQ ID NO: 38) |
| CL9: | 5'ATGGT(G,A)TCC(T,A)CA(G,C)C TCAGTTCCTT3' | (SEQ ID NO: 39) |
| CL10: | 5'ATGTATATATGTTTGTTGTCTATT TC3' | (SEQ ID NO: 40) |
| CL11: | 5'ATGGAAGCCCCAGCTCAGCTTCTC TT3' | (SEQ ID NO :41) |

TABLE 2-continued

| Oligonucleotide primers for the 5' region of mouse light chains. | | |
|---|---|---|
| CL12A: | 5'ATG(A,G)AGT(T,C)(A,T)CAGAC CCAGGTCTT(T,C)(A,G)T3' | (SEQ ID NO: 42) |
| C12B: | 5'ATGGAGACACATTCTCAGGTCTTT GT3' | (SEQ ID NO: 43) |
| CL13: | 5'ATGGATTCACAGGCCCAGGTTCTT AT3' | (SEQ ID NO: 44) |
| CL14: | 5'ATGATGAGTCCTGCCCAGTTCCTG TT3' | (SEQ ID NO: 45) |
| CL15: | 5'ATGAATTTGCCTGTTCATCTCTTGGT GCT3' | (SEQ ID NO: 46) |
| CL16: | 5'ATGGATTTTCAATTGGTCCTCATCTC CTT3' | (SEQ ID NO: 47) |
| CL17A: | 5'ATGAGGTGCCTA(A,G)CT(C,G)AG TTCCTG(A,G)G3' | (SEQ ID NO: 48) |
| CL17B: | 5'ATGAAGTACTCTGCTCAGTTTCTA GG3' | (SEQ ID NO: 49) |
| CL17C: | 5'ATGAGGCATTCTCTTCAATTCTTG GG3' | (SEQ ID NO: 50 |

Each of the above primers has the sequence 5'GGACTGTTCGAAGCCGCCACC3' (SEQ ID NO:51) added to its 5' end.

TABLE 3

| Oligonucleotide primers for the 3' ends of mouse Vh and Vl genes. |
|---|
| Light chain (CL12): 5'GGATACAGTTGGTGCAGCATCCGTACGTTT3' (SEQ ID NO: 52) |
| Heavy chain (R2155): 5'GCAGATGGGCCCTTCGTTGAGGCTG(A,C)(A,G)GAGAC(G,T,A)GTGA3' (SEQ ID NO: 53) |

TABLE 4

| a) 5' Primer mixtures for light chain PCR reactions | |
|---|---|
| pool 1: | CL2. |
| pool 2: | CL7. |
| pool 3: | CL13. |
| pool 4: | CL6. |
| pool 5: | CL5A, CL9, CL17A. |
| pool 6: | CL8. |
| pool 7: | CL12A. |
| pool 8: | CL1, CL3, CL4, CL5, CL10, CL11, CL2B, CL14, CL15, CL16, CL17B, CL17C. |
| b) 5' Primer mixtures for heavy chain PCR reactions | |
| pool 1: | CHI, CH2, CH3, CH4. |
| pool 2: | CH5, CH6, CH7, CH8. |
| pool 3: | CH9, CH10, CH11, CH12. |

TABLE 5

| Primers used in nucleotide sequence analysis | | |
|---|---|---|
| R1053: | 5'GCTGACAGACTAACAGACTGTTCC3' | (SEQ ID NO: 54) |
| R720: | 5'GCTCTCGGAGGTGCTCCT3' | (SEQ ID NO: 55) |

Evaluation of Activities of Chimeric Genes

The activities of the chimeric genes were evaluated by expressing them in mammalian cells and purifying and quantitating the newly synthesised antibodies. The methodology for this is described below, followed by a description of the biochemical and cell based assays used for the biological characterisation of the antibodies.

a) Production of Chimeric hTNF40 Antibody Molecule

Chimeric antibody for biological evaluation was produced by transient expression of the appropriate heavy and light chain pairs after co-transfection into Chinese Hamster Ovary (CHO) cells using calcium phosphate precipitation.

On the day prior to transfection, semi-confluent flasks of CHO-L761 cells were trypsinised, the cells counted and T75 flasks set up each with $10^7$ cells.

On the next day, the culture medium was changed 3 hours before transfection. For transfection, the calcium phosphate precipitate was prepared by mixing 1.25 ml of 0.25 M $CaCl_2$ containing 50 μg of each of heavy and light chain expression vectors with 1.25 ml of 2×HBS (16.36 g NaCl, 11.0 g HEPES and 0.4 g $Na_2HPO_4$ in 1 litre water with the pH adjusted to 7.1 with NaOH) and adding immediately into the medium of the cells. After 3 hours at 37° C. in a $CO_2$ incubator, the medium and precipitate were removed and the cells shocked by the addition of 15 ml 15% glycerol in phosphate buffered saline (PBS) for 1 minute. The glycerol was removed, the cells washed once with PBS and incubated for 48-96 hours in 25 ml medium containing 10 mM sodium butyrate. Antibody could be purified from the culture medium by binding to and elution from protein A-Sepharose.

b) ELISA

For the ELISA, Nunc ELISA plates were coated overnight at 4° C. with a $F(ab)_2$ fragment of a polyclonal goat anti-human Fc fragment specific antibody (Jackson Immunoresearch, code 109-006-098) at 5 μg/ml in coating buffer (15 mM sodium carbonate, 35 mM sodium hydrogen carbonate, pH 6.9). Uncoated antibody was removed by washing 5 times with distilled water. Samples and purified standards to be quantitated were diluted to approximately 1 μg/ml in conjugate buffer (0.1 M Tris-HCl, pH 7.0, 0.1 M NaCl, 0.2% v/v Tween 20, 0.2% w/v Hammersten casein). The samples were titrated in the microtitre wells in 2-fold dilutions to give a final volume of 01 ml in each well and the plates incubated at room temperature for 1 hour with shaking. After the first incubation step the plates were washed 10 times with distilled water and then incubated for 1 hour as before with 0.1 ml of a mouse monoclonal anti-human kappa (clone GD12) peroxidase conjugated antibody (The Binding Site, code MP135) at a dilution of 1 in 700 in conjugate buffer. The plate was washed again and substrate solution (0.1 ml) added to each well. Substrate solution contained 150 μl N,N,N,N-tetramethylbenzidine (10 mg/ml in DMSO), 150 μl hydrogen peroxide (30% solution) in 10 ml 0.1 M sodium acetate/sodium citrate, pH 6.0. The plate was developed for 5-10 minutes until the absorbance at 630 nm was approximately 1.0 for the top standard. Absorbance at 630 nm was measured using a plate reader and the concentration of the sample determined by comparing the titration curves with those of the standard.

c) Determination of Affinity Constants by BiaCore Analysis.

The binding interaction between hTNF40 and human TNF was investigated using BIA technology. An affinity purified goat polyclonal antibody, directed against the constant region of hTNF40, was immobilised on the dextran polymer sensor chip surface using standard NHS/EDC chemistry. Relatively low levels (200-500 RU) of hTNF40 were captured to ensure mass transport effects were minimised. Human TNF at different concentrations was passed over the captured hTNF40 to allow assessment of the association kinetics. Following the injection of ligand, buffer was passed over the surface so that the dissociation could be measured. The association and dissociation rate constants for the interaction between solid phase hTNF40 and human TNF were calculated, and a $K_D$ value was derived.

Example 1

CDR-Grafting of hTNF40

The molecular cloning of genes for the variable regions of the heavy and light chains of the hTNF40 antibody and their use to produce chimeric (mouse-human) hTNF40 antibodies has been described above. The nucleotide and amino acid sequences of the murine hTNF40 Vl and Vh are shown in FIGS. 6 and 7 (SEQ ID NOS:103 and 105), respectively. This example describes the CDR-grafting of the hTNF40 antibody.

CDR-Grafting of hTNF40 Light Chain

Alignment of the framework regions of hTNF40 light chain with those of the four human light chain subgroups (Kabat et al., 1991, supra) revealed that hTNF40 was most homologous to antibodies in human light chain subgroup 1. Consequently, for constructing the CDR-grafted light chain, the framework regions chosen corresponded to those of the human group I consensus sequence.

A comparison of the amino acid sequences of the framework regions of murine hTNF40 and the consensus human group 1 light chains is given in FIG. 1 and shows that there are 22 differences (underlined) between the two sequences. Analysis of the contribution that any of these framework differences might have on antigen binding identified 2 residues for investigation; these are at positions 46 and 60. Based on this analysis, two versions of the CDR-grafted light chain were constructed. In the first of these, hTNF40-gLI (SEQ ID NO:8), residues 46 and 60 are derived from the hTNF40 light chain while in the second, hTNF40-gL2 (SEQ ID NO:10), all residues are human consensus except residue number 60 which is from the hTNF40 light chain.

Construction of CDR-Grafted Light Chain hTNF40-gL1.

The construction of hTNF40-gLI is given below in detail. The following overlapping oligonucleotides (P7982-P7986) were used in the Polymerase Chain Reactions (PCR) to assemble a truncated grafted light chain. The assembled fragment lacks the antibody leader sequence and the first 17 amino acids of framework 1.

```
oligo 1 P7982:
                                              (SEQ ID NO: 56)
5'GAATTCAGGGTCACCATCACTTGTAAAGCCAGTCAGAACGTAGGTACT

AACGTAGCCTGGTATCAGCAAA3'

oligo 2 P7983:
                                              (SEQ ID NO: 57)
5'ATAGAGGAAAGAGGCACTGTAGATGAGGGCTTTTGGGGCTTTACCTGG

TTTTTGCTGATACCAGGCTACGT3'
```

-continued oligo 3 P7984:

(SEQ ID NO: 58)

5'TACAGTGCCTCTTTCCTCTATAGTGGTGTACCATACAGGTTCAGCGGA

TCCGGTAGTGGTACTGATTTCAC3' oligo 4 P7985:

(SEQ ID NO: 59)

5'GACAGTAATAAGTGGCGAAATCTTCTGGCTGGAGGCTACTGATCGTGA

GGGTGAAATCAGTACCACTACCG3' oligo 5 P7986:

(SEQ ID NO: 60)

5'ATTTCGCCACTTATTACTGTCAACAGTATAACATCTACCCACTCACAT

TCGGTCAGGGTACTAAAGTAGAAATCAAACGTACGGAATTC3'

Fwd P7981:

(SEQ ID NO: 61)

5'GAATTCAGGGTCACCATCACTTGTAAAGCC3'

Bwd P7980:

(SEQ ID NO: 62)

5'GAATTCCGTACGTTTGATTTCTACTTTAGT3'

Figure 12:
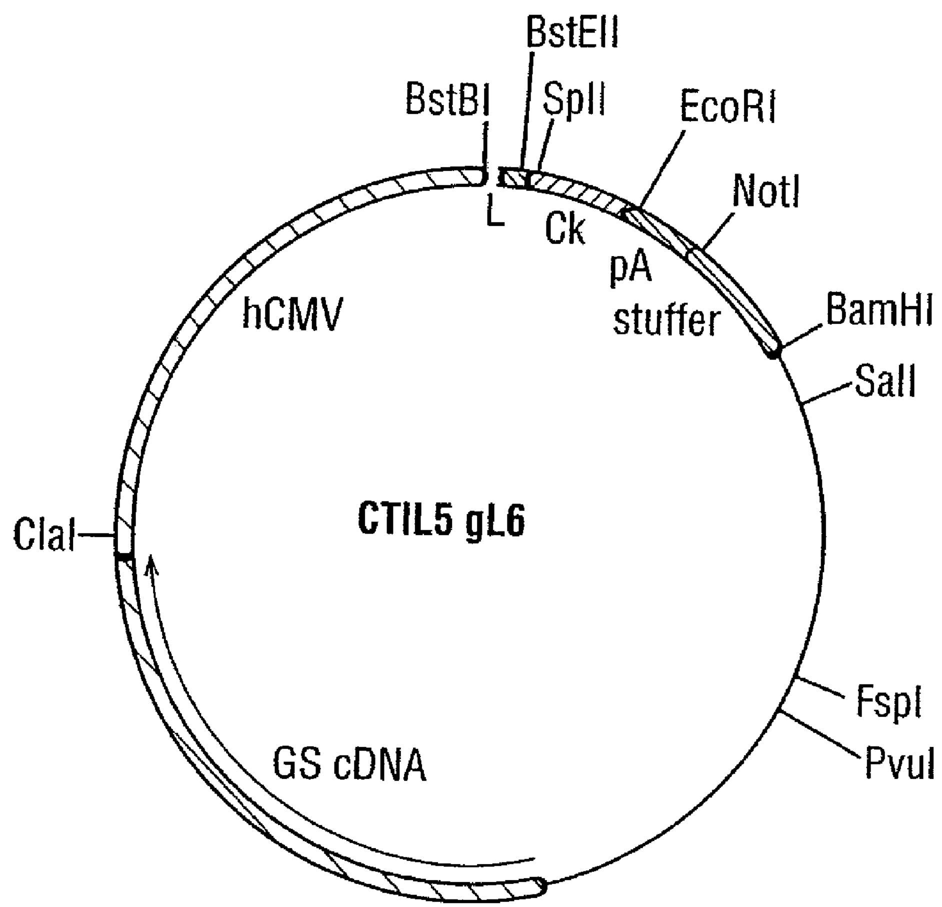
FIG. 12 shows vector CTIL5-gL6.

A PCR reaction, 100 μl, was set up containing, 10 mM Tris-HCl pH 8.3, 1.5 mM $MgCl_2$, 50 mM KCl, 0.01% w/v gelatin, 0.25 mM each deoxyribonucleoside triphosphate, 2 pmoles of P7982, P7983, P7984, P7985, P7986, 10 pmoles of P7980, P7981 and 1 unit of Taq polymerase. Reactions were cycled through 94° C. for 1 minute, 55° C. for 1 minute and 72° C. for 1 minute. After 30 cycles, each reaction was analysed by electrophoresis on an agarose gel and the PCR fragment excised from the gel and recovered using a Mermaid Kit. The recovered fragment was restricted with the enzymes BstEII and SpII in the appropriate buffer. The resulting product was finally electrophoresed on an agarose gel and the 270 base pair DNA fragment recovered from a gel slice and ligated into vector CTIL5-gL6 (FIG. 12), that had previously been digested with the same enzymes. The above vector provides the missing antibody leader sequence and the first 17 amino acids of framework 1.

The ligation mixture was used to transform *E. coli* strain LM1035 and resulting colonies analysed by PCR, restriction enzyme digests and nucleotide sequencing. The nucleotide and amino acid sequence of the VI region of hTNF40-gLI is shown in FIG. 8 (SEQ ID NO:8).

Construction of CDR-Grafted Light Chain hTNF40-gL2.

hTNF40-gL2 (SEQ ID NO:10) was constructed using PCR. The following oligonucleotides were used to introduce the amino acid changes:

R1053:

(SEQ ID NO: 63)

5'GCTGACAGACTAACAGACTGTTCC3'

R5350:

(SEQ ID NO: 64)

5'TCTAGATGGCACACCATCTGCTAAGTTTGATGCAGCATAGATCAGGAG

CTTAGGAGC3'

R5349:

(SEQ ID NO: 65)

5'GCAGATGGTGTGCCATCTAGATTCAGTGGCAGTGGATCAGGCACAGAC

TTTACCCTAAC3'

R684:

(SEQ ID NO: 66)

5'TTCAACTGCTCATCAGAT3'

Two reactions, each 20 μl, were set up each containing 10 mM Tris-HCl pH 8.3, 1.5 mM $MgCl_2$, 50 mM KCl, 0.01% w/v gelatin, 0.25 mM each deoxyribonucleoside triphosphate, 0.1 μg hTNF40-gL1, 6 pmoles of R1053/R5350 or R5349/R684 and 0.25 units Taq polymerase. Reactions were cycled through 94° C. for 1 minute, 55° C. for 1 minute and 72° C. for 1 minute. After 30 cycles, each reaction was analysed by electrophoresis on an agarose gel and the PCR fragments excised from the gel and recovered using a Mermaid Kit.

Aliquots of these were then subjected to a second round of PCR. The reaction, 100 μl, contained 10 mM Tris-HCl pH 8.3, 1.5 mM $MgCl_2$, 50 mM KCl, 0.01% w/v gelatin, 1/5 of each of the PCR fragments from the first set of reactions, 30 pmoles of R1053 and R684 and 2.5 units Taq polymerase. Reaction temperatures were as above. After the PCR, the mixture was extracted with phenol/chloroform and then with chloroform and precipitated with ethanol. The ethanol precipitate was recovered by centrifugation, dissolved in the appropriate buffer and restricted with the enzymes BstEII and SpII. The resulting product was finally electrophoresed on an agarose gel and the 270 base pair DNA fragment recovered from a gel slice and ligated into the vector pMR15.1 (FIG. 4) that had previously been digested with the same enzymes.

The ligation mixture was used to transform *E. coli* LM1035 and resulting colonies analysed by PCR, restriction enzyme digests and nucleotide sequencing. The nucleotide and amino acid sequence of the VI region of hTNF40-g1L2 is shown in FIG. 9 (SEQ ID NO:10).

CDR-Grafting of hTNF40 Heavy Chain

CDR-grafting of hTNF40 heavy chain was accomplished using the same strategy as described for the light chain hTNF40 heavy chain was found to be most homologous to human heavy chains belonging to subgroup 1 and therefore the consensus sequence of the human subgroup 1 frameworks was chosen to accept the hTNF40 heavy chain CDRs.

To investigate the requirement of a homologous human framework to act as an acceptor framework for CDR-grafting, a second framework, human group 3, was selected to humanise hTNF40 heavy chain.

A comparison of hTNF40 with the two different frameworks region is shown in FIG. 2 where it can be seen that hTNF40 differs from the human subgroup 1 consensus at 32 positions (underlined) (FIG. 2) and differs from the human subgroup 3 consensus at 40 positions (underlined) (FIG. 2). After analysis of the contribution that any of these might make to antigen binding, residues 28, 38, 46, 67, 69 and 71 were retained as donor in the CDR-grafted heavy chain gh1hTNF40.1, using the group 1 framework. Residues 27, 28, 30, 48, 49, 69, 71, 73, 76 and 78 were retained as donor in the CDR-grafted heavy chain, gh3hTNF40.4 using the group 3 framework. Residues 28, 69 and 71 were retained as donor in the CDR-grafted heavy chain, gh1hTNF40.4 using the group 1 framework.

Construction of CDR-Grafted Heavy Chain gh1hTNF40.4 gh1hTNF40.4 (SEQ ID NO:12) was assembled by subjecting overlapping oligonucleotides to PCR in the presence of the appropriate primers. The following oligonucleotides were used in the PCR:

Group 1 graft
oligo 1 P7989:

(SEQ ID NO: 67)

5'GAAGCACCAGGCTTCTTAACCTCTGCTCCTGACTGGACCAGCTGCACC

TGAGAGTGCACGAATTC3'

-continued oligo 2 P7990:
(SEQ ID NO: 68)
5'GGTTAAGAAGCCTGGTGCTTCCGTCAAAGTTTCGTGTAAGGCCTCAGG

CTACGTGTTCACAGACTATGGTA3' oligo 3 P7991:
(SEQ ID NO: 69)
5'CCAACCCATCCATTTCAGGCCTTGTCCCGGGGCCTGCTTGACCCAATT

CATACCATAGTCTGTGAACACGT3' oligo 4 P7995:
(SEQ ID NO: 70)
5'GGCCTGAAATGGATGGGTTGGATTAATACTTACATTGGAGAGCCTATT

TATGTTGACGACTTCAAGGGCAGATTCACGTTC3' oligo 5 P7992:
(SEQ ID NO: 71)
5'CCATGTATGCAGTGCGTTGTGGAGGTGTCTAGAGTGAACGTGAATCTG

CCCTTGAA3' oligo 6 P7993:
(SEQ ID NO: 72)
5'CCACAAGCACTGCATACATGGAGCTGTCATCTCTGAGATCCGAGGACA

CCGCAGTGTACTAT3' oligo 7 P7994:
(SEQ ID NO: 73)
5'GAATTCGGTACCCTGGCCCCAGTAGTCCATGGCATAAGATCTGTATCC

TCTAGCACAATAGTACACTGCGGTGTCCTC3'

Fwd: P7988:
(SEQ ID NO: 74)
5'GAATTCGTGCACTCTCAGGTGCAGCTGGTC3'

Bwd P7987:
(SEQ ID NO: 75)
5'GAATTCGGTACCCTGGCCCCAGTAGTCCAT3'

The assembly reaction, 100 μl, contained 10 mM Tris-HCl pH 8.3, 1.5 mM $MgCl_2$, 50 mM KCl, 0.01% w/v gelatin, 0.25 mM each deoxyribonucleoside triphosphate, 2 pmole of each of p7989, p7990, p7991, p7995, p7992, p7993 and p7994, 10 pmoles of each of p7988 and p7987 and 1 unit Taq polymerase. Reactions were cycled through 94° C. for 1 minute, 55° C. for 1 minute and 72° C. for 1 minute. After 30 cycles, the reaction was extracted with phenol/chloroform (1/1), then with chloroform and precipitated with ethanol. After centrifugation, the DNA was dissolved in the appropriate restriction buffer and digested with ApaLI and KpnI. The resulting fragment was isolated from an agarose gel and ligated into pMR14 (FIG. 5) that had previously been digested with the same enzymes. pMR14 contains the human gamma 4 heavy chain constant region when pMR14 is cleaved with ApaLI and KpnI, the cleaved vector is able to receive the digested DNA such that the 3' end of the digested DNA joins in reading frame to the 5' end of the sequence encoding the gamma 4 constant region. Therefore, the heavy chain expressed from this vector will be a gamma 4 isotype. The ligation mixture was used to transform *E. coli* LM1035 and resulting bacterial colonies screened by restriction digest and nucleotide sequence analysis. In this way, a plasmid was identified containing the correct sequence for gh1hTNF40.4 (FIG. 10) (SEQ ID NO:12).

Construction of CDR-Grafted Heavy Chain gh3hTNF40.4 gh3hTNF40.4 (SEQ ID NO:14) was assembled by subjecting overlapping oligonucleotides to PCR in the presence of the appropriate primers. The following oligonucleotides were used in the PCR:

Group 3 graft oligo 1 P7999:
(SEQ ID NO: 76)
5'GATCCGCCAGGCTGCACGAGACCGCCTCCTGACTCGACCAGCTGAACC

TCAGAGTGCACGAATTC3' oligo 2 P8000:
(SEQ ID NO: 77)
5'TCTCGTGCAGCCTGGCGGATCGCTGAGATTGTCCTGTGCTGCATCTGG

TTACGTCTTCACAGACTATGGAA3' oligo 3 P8001
(SEQ ID NO: 78)
5'CCAACCCATCCATTTCAGGCCCTTTCCCGGGGCCTGCTTAACCCAATT

CATTCCATAGTCTGTGAAGACGT3' oligo 4 P7995:
(SEQ ID NO: 70)
5'GGCCTGAAATGGATGGGTTGGATTAATACTTACATTGGAGAGCCTATT

TATGTTGACGACTTCAAGGGCAGATTCACGTTC3' oligo 5 P7997:
(SEQ ID NO: 79)
5'GGAGGTATGCTGTTGACTTGGATGTGTCTAGAGAGAACGTGAATCTGC

CCTTGAA3' oligo 6 P7998
(SEQ ID NO: 80)
5'CCAAGTCAACAGCATACCTCCAAATGAATAGCCTGAGAGCAGAGGACA

CCGCAGTGTACTAT3' oligo 7 P7993:
(SEQ ID NO: 81)
5'GAATTCGGTACCCTGGCCCCAGTAGTCCATGGCATAAGATCTGTATCC

TCTAGCACAATAGTACACTGCGGTGTCCTC3'

Fwd P7996:
(SEQ ID NO: 82)
5'GAATTCGTGCACTCTGAGGTTCAGCTGGTC3'

Bwd P7987:
(SEQ ID NO: 75)
5'GAATTCGGTACCCTGGCCCCAGTAGTCCAT3'

The assembly reaction, 100 μl, contained 10 mM Tris-HCl pH 8.3, 1.5 mM $MgCl_2$, 50 mM KCl, 0.01% w/v gelatin, 0.25 mM each deoxyribonucleoside triphosphate, 2 pmole of each of p7999, p8000, p8001, p7995, p7997, p7998 and p7993, 10 pmoles of each of p7996 and p7987 and 1 unit Taq polymerase. Reactions were cycled through 94° C. for 1 minute, 55° C. for 1 minute and 72° C. for 1 minute. After 30 cycles, the reaction was extracted with phenol/chloroform (1/1), then with chloroform and precipitated with ethanol. After centrifugation, the DNA was dissolved in the appropriate restriction buffer and digested with ApaLI and KpnI. The resulting fragment was isolated from an agarose gel and ligated into pMR14 (FIG. 5) that had previously been digested with the same enzymes. pMR14 contained the human gamma 4 heavy chain constant region. When pMR14 is cleaved with ApaL1 and KpnI, the cleaved vector is able to receive the digested DNA such that the 3' end of the digested DNA joins in reading frame to the 5' end of the sequence encoding the gamma 4 constant region. Therefore, the heavy chain expressed from this vector will be a gamma 4 isotype. The ligation mixture was used to transform *E. coli* LM1035 and resulting bacterial colonies screened by restriction digestion and nucleotide sequence analysis. In this way, a plasmid was identified containing the correct sequence for gh3hTNF40.4 (SEQ ID NO:14) (FIG. 11).

Production of CDR-Grafted Modified Fab Fragment.

A CDR-grafted, modified Fab fragment, based on antibody hTNF40, was constructed using the *E. coli* vector pTTO-1. The variable regions of antibody hTNF40 are sub-cloned into this vector and the intergenic sequence optimised to create pTTO(CDP870). The pTTO expression vector is designed to give rise to soluble, periplasmic accumulation of recombinant proteins in *E. coli*. The main features of this plasmid are:

(i) tetracycline resistance marker—antibiotic not inactivated by the product of resistance gene, hence selection for plasmid-containing cells is maintained;

(ii) low copy number—origin of replication derived from plasmid p15A, which is compatible with plasmids containing colE1 derived replicons;

(iii) strong, inducible tac promoter for transcription of cloned gene(s);

(iv) $lacI_q$ gene—gives constitutive expression of the lac repressor protein, maintaining the tac promoter in the repressed state until induction with IPTG/allolactose;

(v) OmpA signal sequence—gives periplasmic secretion of cloned gene(s); and (vi) translational coupling of OmpA signal sequence to a short lacZ peptide, giving efficient initiation of translation.

The vector has been developed for expression of modified Fab fragments from a dicistronic message by the design of a method to select empirically the optimum intergenic sequence from a series of four purpose-built cassettes. The application of this in the construction of pTTO(CDP870) is described.

Materials and Methods

DNA Techniques

Standard procedures were used for protocols including DNA restriction, agarose gel electrophoresis, ligation and transformation. Restriction enzymes and DNA modifying enzymes were obtained from New England Biolabs or Boehringer Mannheim, and were used according to the supplier's recommendations. DNA fragments were purified from agarose using the GeneClean protocol (BIO 101). Oligonucleotides were supplied by Oswel Oligonucleotide Service and were synthesized at the 40 nm scale. Plasmid DNA was isolated using Plasmid DNA Mini/Midi kits from Qiagen. PCR was performed using Perkin Elmer 'Amplitaq' as recommended. DNA sequencing was performed using the Applied Biosystems Taq cycle sequencing kit.

Shake Flask Induction

*E. coli* W3110 cultures were grown in L-broth supplemented with tetracycline (7.5 μg/ml). For inductions, fresh overnight cultures (grown at 30° C.) were diluted to $OD_{600}$ of 0.1 into 200 ml L-broth in a 2 L baffled flask and were grown at 30° C. in an orbital incubator. At $OD_{600}$ of 0.5, IPTG was added to 200 μM. Samples (normalised for OD) were taken at intervals.

Periplasmic Extraction

Culture samples were chilled on ice (5 minutes) then cells were harvested by centrifugation. Following resuspension in extraction buffer (100 mM Tris-HCl, 10 mM EDTA, pH 7.4) samples were incubated overnight at 30° C., then clarified by centrifugation.

Assembly Assay

Modified Fab concentrations were determined by ELISA. Plates were coated at 4° C. overnight with anti-human Fd 6045 (2 μg/ml in coating buffer, physiological saline, 100 μl per well). After washing, 100 μl of sample was loaded per well; purified A5B7 gamma-1 Fab', initially, at 2 μg/ml, was used as a standard. Samples were serially diluted 2-fold across the plate in sample conjugate buffer (per litre: 6.05 g trisaminomethane; 2.92 g NaCl; 0.1 ml Tween-20; 1 ml casein (0.2%)); plates were incubated for 1 hour at room temperature, with agitation. Plates were washed and dried, then 1001 of anti-human C-kappa (GD12)-peroxidase was added (diluted in sample conjugate buffer). Incubation was carried out at room temperature for 1 hour with agitation. Plates were washed and dried, then 100 μl of substrate solution was added (10 ml sodium acetate/citrate solution (0.1 M pH 6); 100 μl $H_2O_2$ solution; 100 μl tetramethylbenzidine solution (10 mg/ml in dimethylsulphoxide)). Absorbance at 630 nm was read 4-6 minutes after substrate addition.

Construction of Plasmid pTTO 1

(a) Replacement of the pTTQ9 Polylinker

Figure 14:
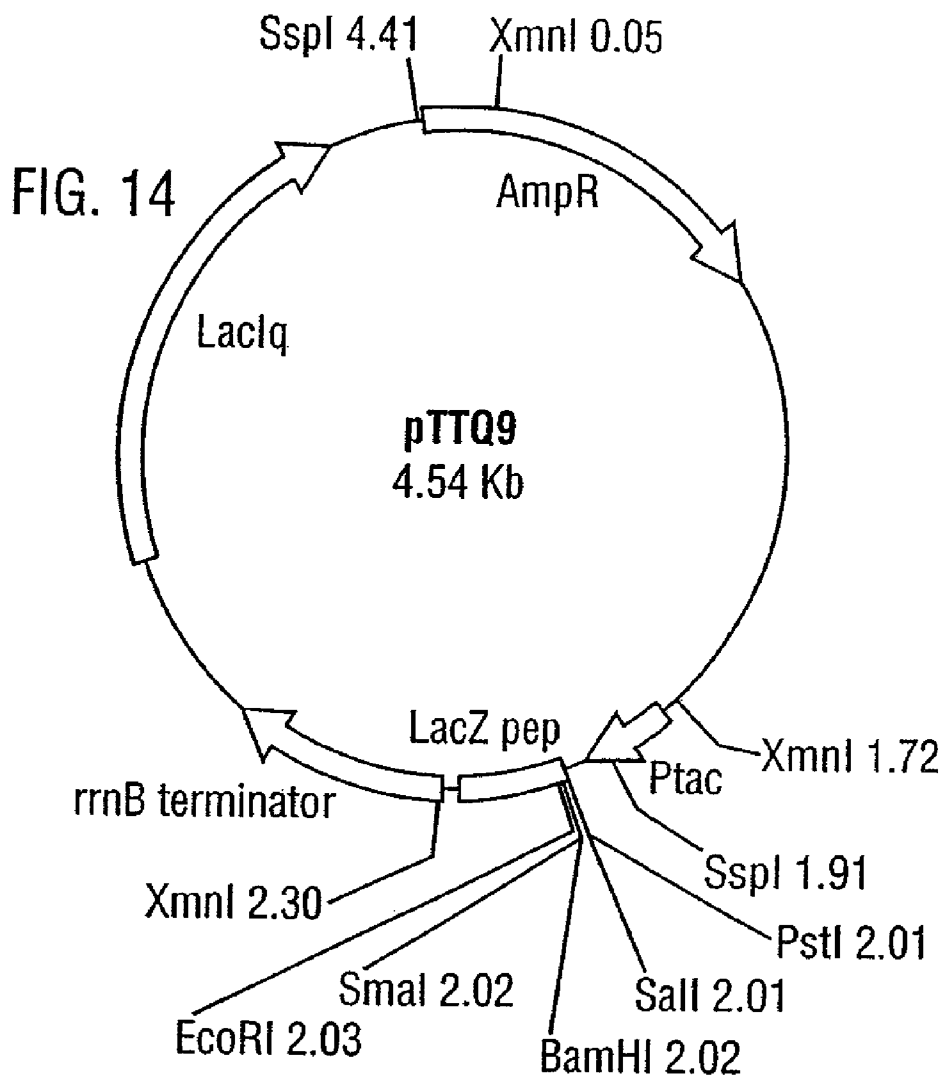
FIG. 14 shows vector pTTQ9.

Plasmid pTTQ9 was obtained from Amersham and is shown in FIG. 14. An aliquot (2 μg) was digested with restriction enzymes SalI and EcoRI, the digest was run on a 1% agarose gel and the large DNA fragment (4520 bp) was purified. Two oligonucleotides were synthesized which, when annealed together, encode the OmpA polylinker region shown in FIG. 15. This sequence has cohesive ends which are compatible with the SalI and EcoRI ends generated by restriction of pTTQ9. By cloning this oligonucleotide 'cassette' into the pTTQ9 vector, the SalI site is not regenerated, but the EcoRI site is maintained. The cassette encodes the first 13 amino acids of the signal sequence of the *E. coli* outer-membrane protein Omp-A, preceded by the Shine Dalgarno ribosome binding site of the OmpA gene. In addition restriction sites for enzymes XbaI, MunI, StyI and SplI are present. The MunI and StyI sites are within the coding region of the OmpA signal sequence and are intended as the 5' cloning sites for insertion of genes. The two oligonucleotides which make up this cassette were annealed together by mixing at a concentration of 5 pmoles/μl and heating in a waterbath to 95° C. for 3 minutes, then slow cooling to room temperature. The annealed sequence was then ligated into the SalI/EcoRI cut pTTQ9. The resulting plasmid intermediate, termed pTQOmp, was verified by DNA sequencing.

(b) Fragment Preparation and Ligation

Figure 16:
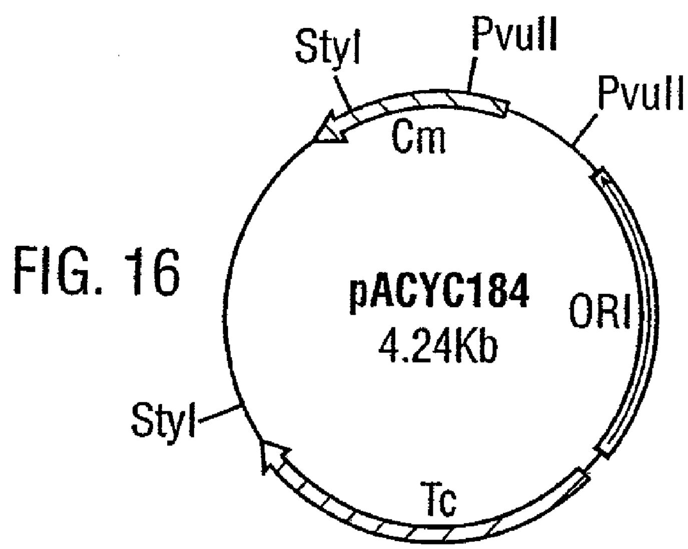
FIG. 16 shows vector pACYC184.

Plasmid pTTO-1 was constructed by ligating one DNA fragment from plasmid pACYC184 to two fragments generated from pTQOmp. Plasmid pACYC184 was obtained from New England Biolabs, and a restriction map is shown in FIG. 16. An aliquot (2 μg) was digested to completion with restriction enzyme StyI, then treated with Mung Bean Nuclease; this treatment creates blunt ends by cutting back 5' base overhangs. Following phenol extraction and ethanol precipitation, the DNA was restricted with enzyme PvuII, generating fragments of 2348, 1081, 412 and 403 bp. The 2348 bp fragment was purified after agarose gel electrophoresis. This fragment encodes the tetracycline resistance marker and the p15A origin of replication. The fragment was then treated with calf intestinal alkaline phosphatase to remove 5' terminal phosphates, thereby preventing the self-ligation of this molecule.

An aliquot (2 μg) of plasmid pTQOmp was digested with enzymes SspI and EcoRI, and the 2350 bp fragment was purified from unwanted fragments of 2040 bp and 170 bp following agarose gel electrophoresis; this fragment encodes the transcriptional terminator region and the $lacI^q$ gene. Another aliquot (2 μg) of pTQOmp was digested with EcoRI and XmnI, generating fragments of 2289, 1670, 350 and 250 bp. The 350 bp fragment, encoding the tac promoter, OmpA signal sequence and multicloning site, was gel purified.

Figure 17:
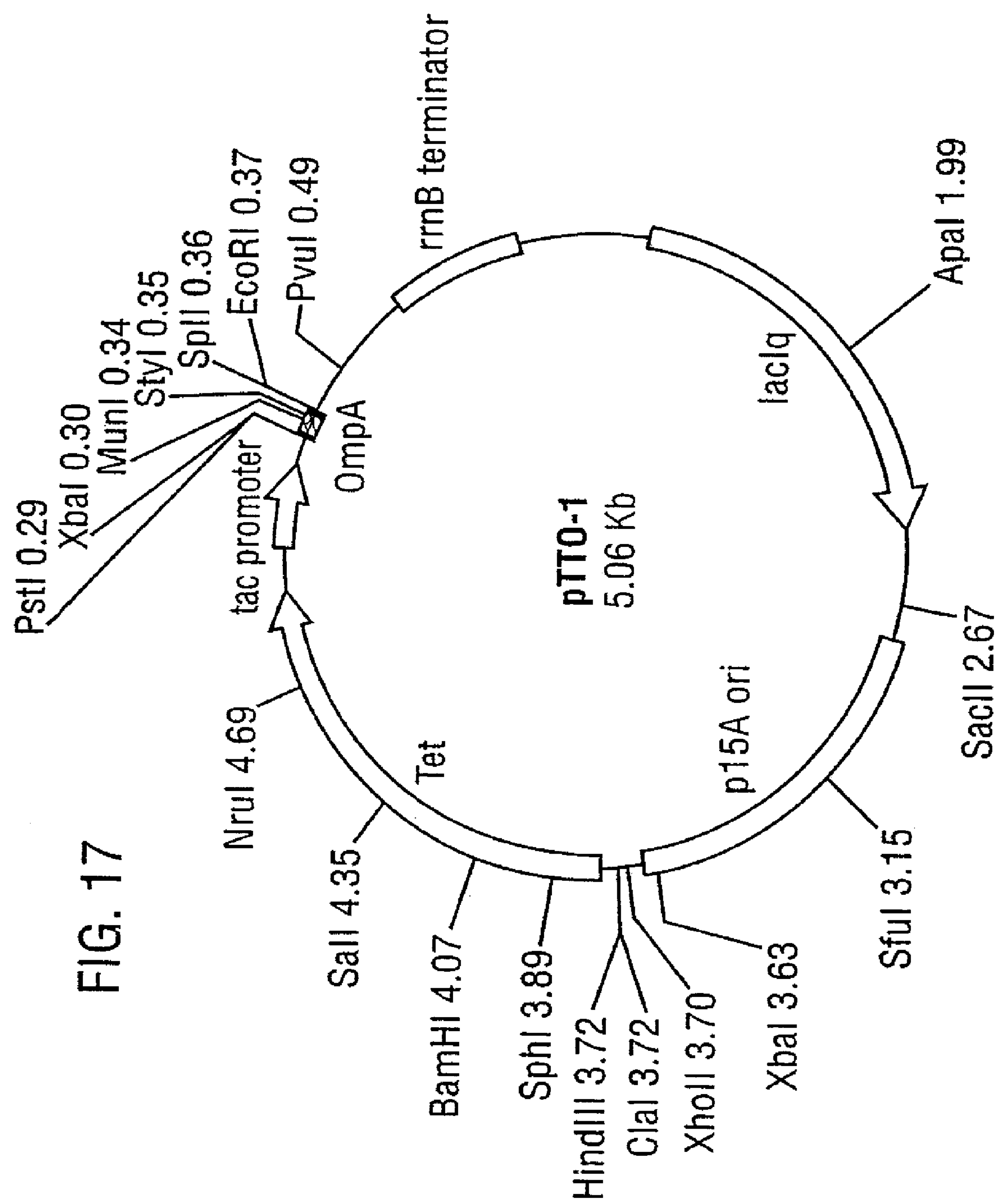
FIG. 17 shows vector pTTO-1.
Figure 18:
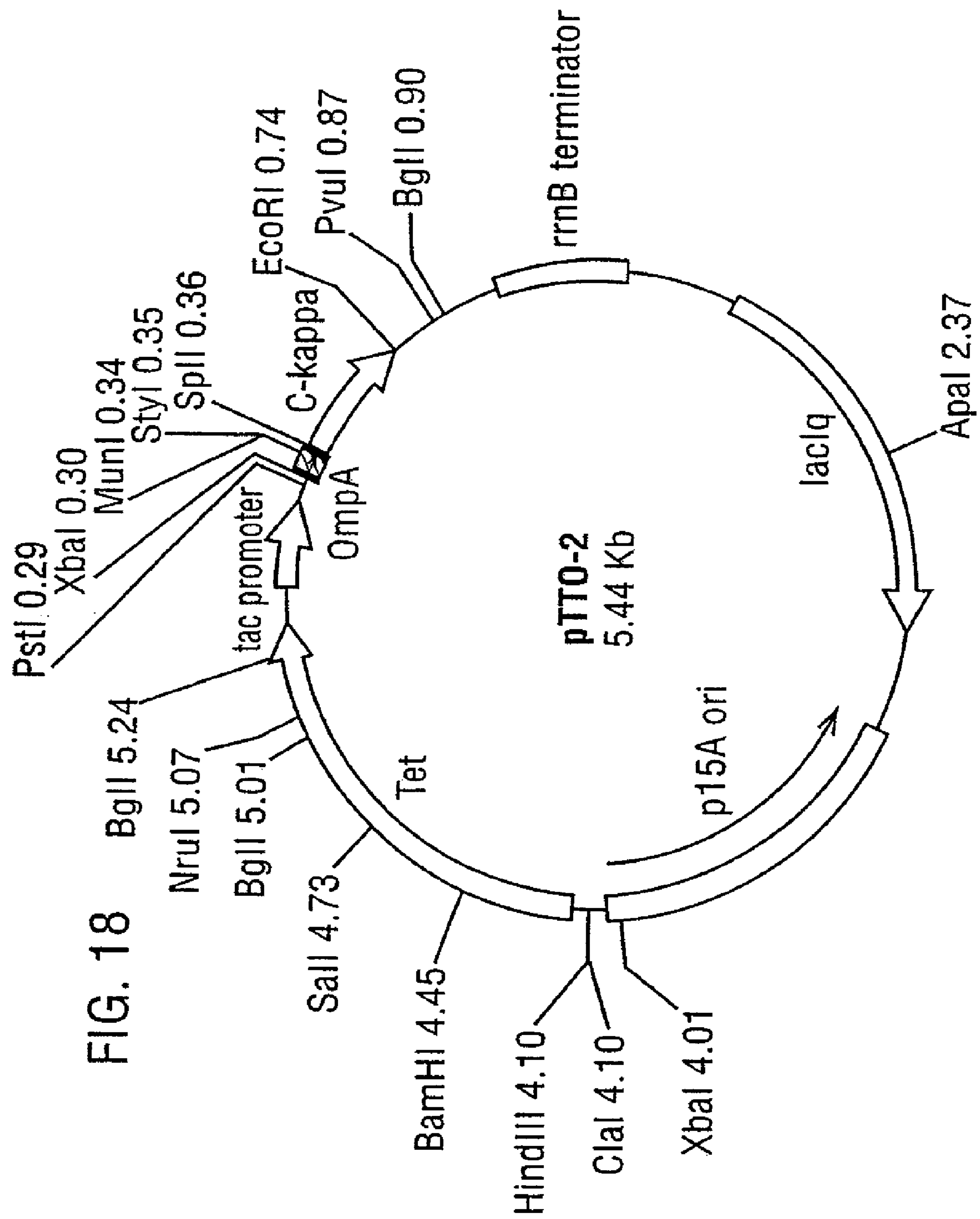
FIG. 18 shows vector pTTO-2.

The three fragments were then ligated, using approximately equimolar amounts of each fragment, to generate the plasmid pTTO-1. All cloning junctions were verified by DNA sequencing. The restriction map of this plasmid is shown in FIG. 17. Plasmid pTTO-2 was then created by insertion of DNA encoding the human Ig light chain kappa constant domain. This was obtained as a SplI-EcoRI restriction fragment from plasmid pHC132, and inserted into the corresponding sites in pTTO-1. Plasmid pTTO-2 is shown in FIG. 18.

Insertion of Humanized hTNF40 Variable Regions into pTTO-2

The variable light chain region hTNF40gL1 (SEQ ID NO:8) was obtained by PCR 'rescue' from the corresponding vector for mammalian cell expression pMR10.1. The OmpA leader sequence replaces the native Ig leader. The sequence of the PCR primers is shown below:

```
5' primer:
                                        (SEQ ID NO: 83)
CGCGCGGCAATTGCAGTGGCCTTGGCTGGTTTCGCTACCGTAGCGCAAGC

TGACATTCAAATGACCCAGAGCCC

3' primer:
                                        (SEQ ID NO: 84)
TTCAACTGCTCATCAGATGG
```

Following PCR under standard conditions, the product was purified, digested with enzymes MunI and SplI then gel purified. The purified fragment was then inserted into the MunI/SplI sites of pTTO-2 to create the light chain intermediate pTTO(hTNF40L).

The variable heavy chain region of gh3hTNF40.4 was obtained in the same way from the vector pGamma-4. The sequence of the PCR primers is shown below:

```
5' primer:
                                        (SEQ ID NO: 85)
GCTATCGCAATTGCAGTGGCGCTAGCTGGTTTCGCCACCGTGGCGCAAGC

TGAGGTTCAGCTGGTCGAGTCAGGAGGC

3' primer:
                                        (SEQ ID NO: 86)
GCCTGAGTTCCACGACAC
```

Following PCR the product was purified, digested with enzymes NheI and ApaI then sub-cloned into the vector pDNAbEng-G1 (FIG. 19). After verification by DNA sequencing, the heavy chain was restricted with enzyme EcoRI and sub-cloned into the EcoRI site of pTTO (hTNF40L) to create the *E. coli* expression plasmid pTTO (hTNF40).

Optimisation of Intergenic Sequence for Modified Fab Expression

In the pTTO vector, modified Fab expression occurs from a dicistronic message encoding first light chain then heavy chain. The DNA sequence between the two genes (intergenic sequence, IGS) can influence the level of expression of the heavy chain by affecting the rate of translational initiation. For example, a short intergenic sequence may result in translational coupling between the light and heavy chains, in that the translating ribosome may not fully dissociate from the mRNA after completing light chain synthesis before initiating heavy chain synthesis. The 'strength' of any Shine Dalgarno (SD) ribosome binding site (homology to 16S rRNA) can also have an effect, as can the distance and sequence composition between the SD and the ATG start codon. The potential secondary structure of mRNA around the ATG is another important factor; the ATG should be in a 'loop' and not constrained within a 'stem', while the reverse applies to the SD. Thus by modifying the composition and length of the IGS it is possible to modify the strength of translational initiation and therefore the level of heavy chain production. It is likely that an optimum rate of translational initiation needs to be achieved to maximise expression of the heavy chain of a given modified Fab. For example, with one modified Fab, a high level of expression may be tolerated, but for a different modified Fab with different amino acid sequence, a high level of expression might prove toxic, perhaps because of different efficiencies of secretion or folding. For this reason, a series of four intergenic sequences were designed (FIG. 20), permitting the empirical determination of the optimum IGS for the hTNF40-based modified Fab. IGS1 and IGS2 have very short intergenic sequences (−1 and +1 respectively) and might be expected to give closely coupled translation; the SD sequences (underlined) are subtly different. These two sequences will most likely confer a high level of translational initiation. IGS3 and IGS4 have a longer distance between start and stop codons (+13) and differ in their sequence composition; IGS3 has a 'stronger' SD sequence. All sequences were studied for secondary structure (using n/fold program) and 'optimised' as far as possible; however, with tight coupling of translation of the two chains the lack of ribosomal dissociation means that the mRNA may not be 'naked', preventing secondary structure formation.

Cloning of IGS Variants

The IGS cassettes shown in FIG. 20 have flanking SacI and MunI cloning sites. They were built by annealing complementary oligonucleotide pairs. A vector fragment was prepared by digesting pTTO(hTNF40) with SacI and NotI, and a heavy chain fragment was prepared by digesting pDNAbEngG1 (hTNF40H) with MunI and NotI. Three-way ligations were then performed, using equimolar amounts of the two restriction fragments and approximately 0.05 pmoles of each annealed oligo cassette. This created the four expression plasmids pTTO(hTNF40 IGS-1), pTTO(hTNF40 IGS-2), pTTO(hTNF40 IGS-3), pTTO(hTNF40 IGS-4).

Shake Flask Expression Analysis

The four plasmids were transformed into *E. coli* strain W3110, along with the original expression construct, and then analysed for expression in shake flasks as described. The results of a typical experiment are shown in FIG. 21. The different intergenic sequences confer different expression profiles. IGS1 and IGS2 accumulate periplasmic modified Fab rapidly with a peak at 1 hour post induction, after which the level recovered falls. The peak is greater and the fall sharper for IGS1. These results are consistent with a high level of synthesis, as expected for close translational coupling for these constructs. IGS1 apparently confers a higher level of heavy chain expression than does IGS2. In this instance, it appears that this high level of expression is poorly tolerated, since periplasmic expression levels fall after the 1 hour peak. This is seen on the growth profile of the IGS1 culture (not shown), which peaks at 1 hour post induction before falling, suggesting cell death and lysis. IGS3 accumulates modified Fab more slowly but peaks at 2 hours post induction with a higher peak value (325 ng/ml/OD), before levels fall. The growth of this culture continued to 3 hours post induction and reached a higher peak biomass (not shown). This is consistent with a lower level of heavy chain synthesis. IGS4 accumulates material at a slower rate still and fails to reach the high peak of productivity of the other 3 constructs. All IGS variants out-perform the original vector significantly. The hypothesis that the different IGS sequences confer different rates of translational initiation is supported by these experimental results. For the hTNF40-based modified Fab it appears that a high rate of heavy chain translational initiation is poorly tolerated and is therefore not optimal. A slower rate, as conferred by IGS3, results in better growth characteristics and consequently a better yield accumulates over time.

Figure 22:
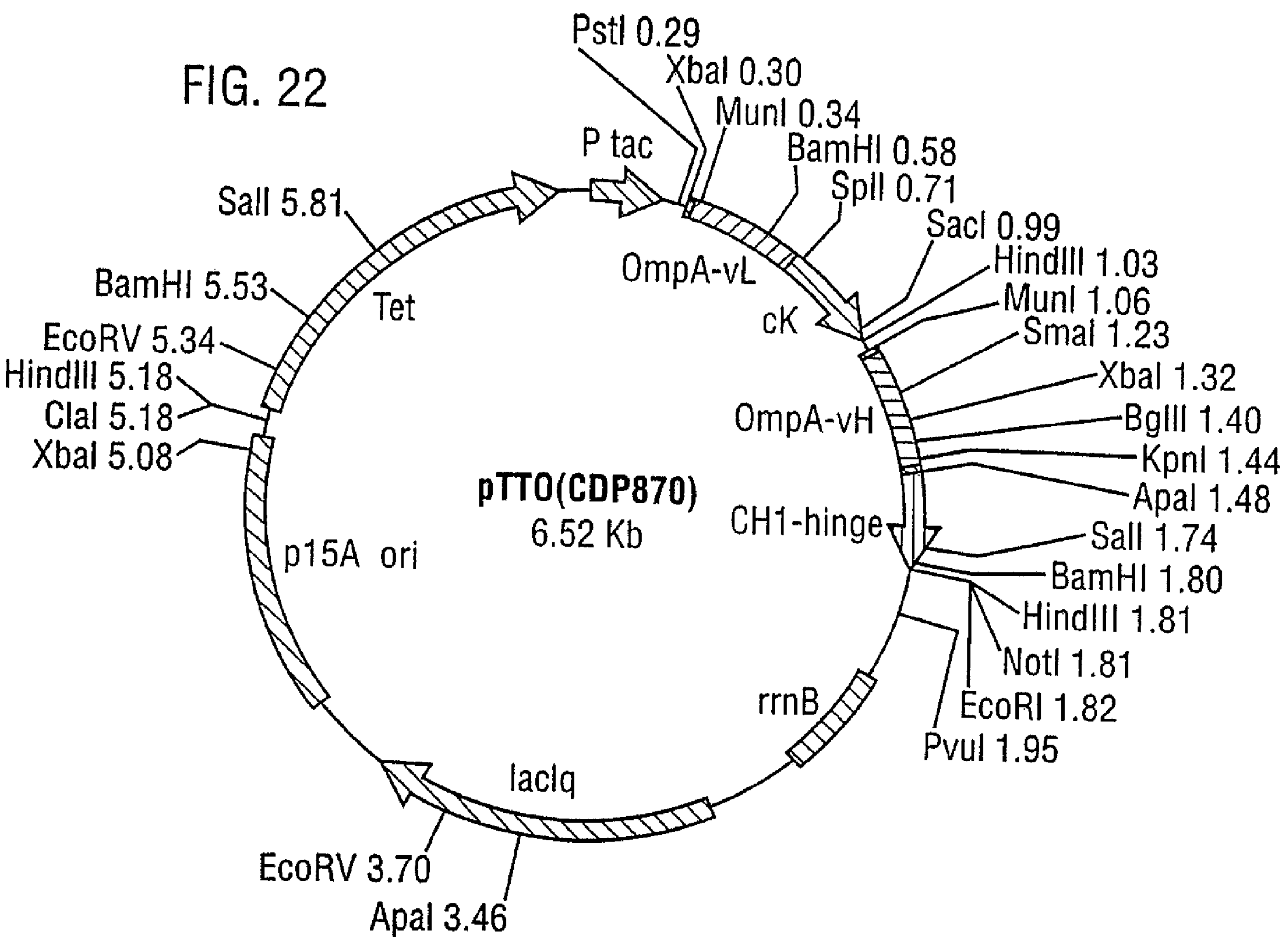
FIG. 22 shows vector pTTO(CDP870).

Following comparison of productivity in the fermenter the IGS3 construct was selected as the highest yielding and was termed pTTO(CDP870)—see FIG. 22.

The heavy chain encoded by the plasmid pTTO(CDP870) has the sequence given in SEQ ID NO:130 and the light chain has the sequence given in SEQ ID NO:128.

PEGylation of CDR-Grafted, hTNF40 Based Modified Fab.

The purified modified Fab is site-specifically conjugated with a branched molecule of PEG. This is achieved by activation of a single cysteine residue in a truncated hinge region of the modified Fab, followed by reaction with (PEG)-lysyl maleimide as previously described (A. P. Chapman et al., Nature Biotechnology 17, 780-783, 1999). The PEGylated molecule is shown in FIG. 13 and is called compound CDP870.

Efficacy of PEGylated CDR-Grafted, hTNF40-Based Modified Fab (CDP870) in Treating Rheumatoid Arthritis.

CDP870 has a long half-life of approximately 11 days.

We evaluated the safety and efficacy of intravenous CDP870 in a randomised double-blind placebo-controlled dose escalating trial in patients with RA.

Methods

Patients:

Patients aged between 18 and 75 years old and who satisfied the 1987 revised American College of Rheumatology (ACR) diagnostic criteria for rheumatoid arthritis (RA) (Arnett et al., Arthritis Rheum., 31, 315-324, 1988) were recruited from outpatient Rheumatology clinics at London, Cambridge, Norfolk and Norwich (United Kingdom). Patients were required to have clinically active disease as defined by having at least 3 of the following criteria: ≧6 painful or tender joints; ≧45 minutes of early morning stiffness; and erythrocyte sedimentation rate (ESR) ≧28 mm/hr. They must have failed to respond to at least one Disease Modifying Anti-Rheumatic Drug (DRARD) and have been off treatment for at least 4 weeks. Corticosteroids were permitted if the dose was ≧7.5 mg/day of prednisolone. Pregnant women, nursing women and women of childbearing potential not using an effective method of contraception were excluded. Patients were also excluded if they had a previous history of malignancy, concomitant severe uncontrolled medical conditions, previous failure of TNFαα-neutralizing therapy or allergy to polyethylene glycol. Written informed consent was obtained from each patient before enrollment. The study was approved by the local research ethics committees.

Treatment Protocol:

36 RA patients were divided into 3 groups, each to receive an increasing dose of the trial drug (1, 5 or 20 mg/kg). Each group of 12 was randomly divided into 8 to receive CDP870 and 4 to receive placebo. CDP870 was given as a single intravenous infusion (100 ml in total) over 60 minutes. Placebo (sodium acetate buffer) was given similarly as a single intravenous infusion of 100 ml over 60 minutes. Treatment was given on an outpatient basis. After 8 weeks, all patients had the opportunity to receive an infusion of either 5 or 20 mg/kg of CDP870 in open fashion.

Clinical Assessment:

RA disease activity was assessed based on the World Health Organization and International League of Associations for Rheumatology (Boers et al., J. Rheumatol—Supplement, 41, 86-89, 1994) and European League Against Rheumatism (EULAR) (Scott et al., Clin. Exp. Rheumatol., 10, 521-525, 1992) core data sets with 28 joint counts. Changes in disease activity were assessed by Disease Activity Score (Prevoo et al., Arthritis Rheum., 38, 44-48, 1995) and the ACR responses criteria (Felson et al., Arthritis Rheum., 38, 727-735, 1995). Assessments were carried out before treatment and at 1, 2, 4, 6 and 8 weeks after therapy. Patients were also assessed for safety and tolerance of the study drug. Haematology, biochemistry, anti-CDP870 antibodies and adverse events were assessed at each visit.

CDP870 Plasma Concentration and Anti-CDP870 Antibodies:

CDP870 was measured by enzyme-linked immunosorbent assay (ELISA). Serial dilutions of patients' plasma were incubated in microtitre plates (Nunc) coated with recombinant human TNFα (Strathmann Biotech GmbH, Hannover). Captured CDP870 was revealed with horseradish peroxidase conjugated goat anti-human kappa light chain (Cappel, ICN) followed by tetramethylbenzidine (TMB) substrate.

Antibodies to CDP870 was screened (at 1/10 plasma dilution) using a double antigen sandwich ELISA with biotinylated CDP870 as the second layer. Bound antibodies were revealed using HRP-streptavidin and TMB substrate. The assay was calibrated using a hyperimmune rabbit IgG standard. A unit of activity is equivalent to 1 μg of the rabbit standard.

Statistical Analysis

The study was exploratory in nature and the sample size was based on previous experience with similar agents. Efficacy of CDP870 was analysed by calculating disease activity score (DAS) and ACR20/50 responses for intention to treat and per-protocol using a closed testing procedure. The disease activity score was calculated as follows: DAS=0.555×square root of (28 tender joints)+0.284×square root of (28 swollen joints)+0.7×In(ESR)+0.0142×(patient's global assessment). First, the pooled active groups were compared to placebo. If this comparison was significant at the 5% level, each dosage group was compared to placebo. All comparisons were two tailed with a significance level of 5%. All P-values were derived from exploratory analysis and should not be used for inferential interpretation.

Results

Demography:

36 patients with RA were recruited. Their demographic details are given in Table 6. The mean age was 56 years and 30 patients were female. The mean duration of RA was 13 years and 21 patients were rheumatoid factor positive. Patients in the different groups have similar demographic characteristics. In the blinded dosing period, 6/12 placebo-treated patients withdrew from the study for deteriorating RA≧4, weeks after dosing. 2/24 CDP870-treated patients withdrew, both in the 1 mg/kg group, for deteriorating RA/lost to follow up >4 weeks after dosing. The difference was statistically significant (p=0.009, Fisher exact test).

TABLE 6

Demographic details (mean ± standard deviation)

| | Number | Sex (M:F) | Age | Duration of Disease | Rheumatoid Factor | Number of previous DMARDs |
|---|---|---|---|---|---|---|
| Placebo | 12 | 1.11 | 51 ± 18 | 12 ± 8 | 8 (67%) | 5 ± 1 |
| 1 mg/kg | 8 | 1:7 | 59 ± 7 | 12 ± 7 | 4 (50%) | 4 ± 1 |
| 5 mg/kg | 8 | 2:6 | 54 ± 13 | 13 ± 5 | 5 (63%) | 5 ± 2 |
| 20 mg/kg | 8 | 2.6 | 61 ± 11 | 14 ± 13 | 4 (50%) | 4 ± 2 |

Figure 23:
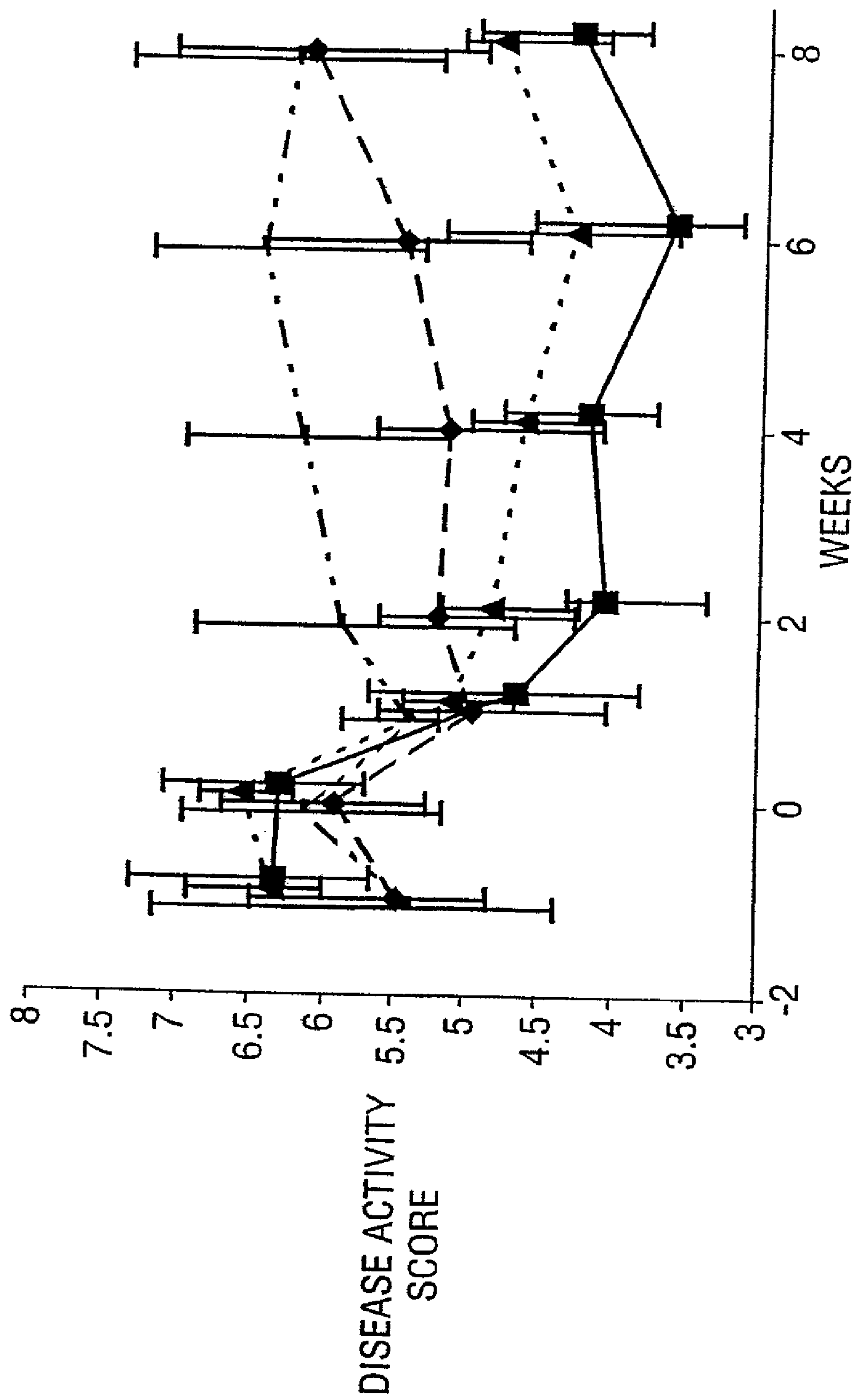
FIG. 23 shows the disease activity score (DAS) in patients treated with different doses of CDP870 and placebo. Median and IQ ranges are presented for the per-protocol population with last observation carried forward. Small squares indicate placebo, diamonds indicate 1 mg/kg, triangles, indicate 5 mg/kg and large squares indicate 20 mg/kg.
Figure 24A:
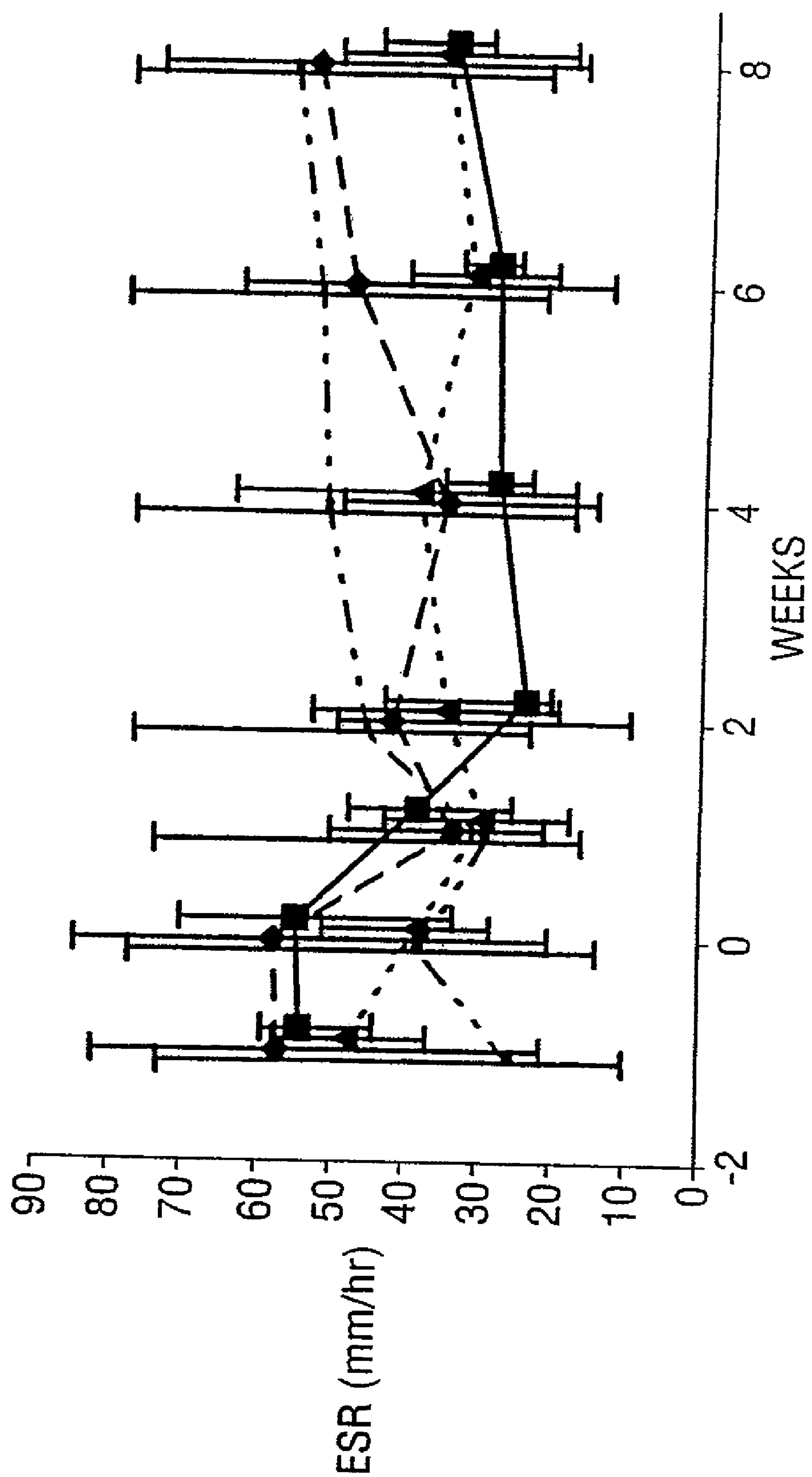
FIG. 24 shows the erythrocyte sedimentation rate (ESR) (FIG. 24A), C reactive protein (CRP) (FIG. 24B), tender joint count (FIG. 24C), swollen joint count (FIG. 24D), patient's assessment of pain (FIG. 24E), disability index (FIG. 24F), patient's global assessment of disease activity (FIG. 24G), physician's global assessment of disease activity (FIG. 24H) in patients treated with different doses of CDP870 and placebo. Median and IQ range are presented for the per-protocol population with last observation carried forward. Small squares indicate placebo, diamonds indicate 1 mg/kg, triangles indicate 5 mg/kg and large squares indicate 20 mg/kg.
Figure 24B:
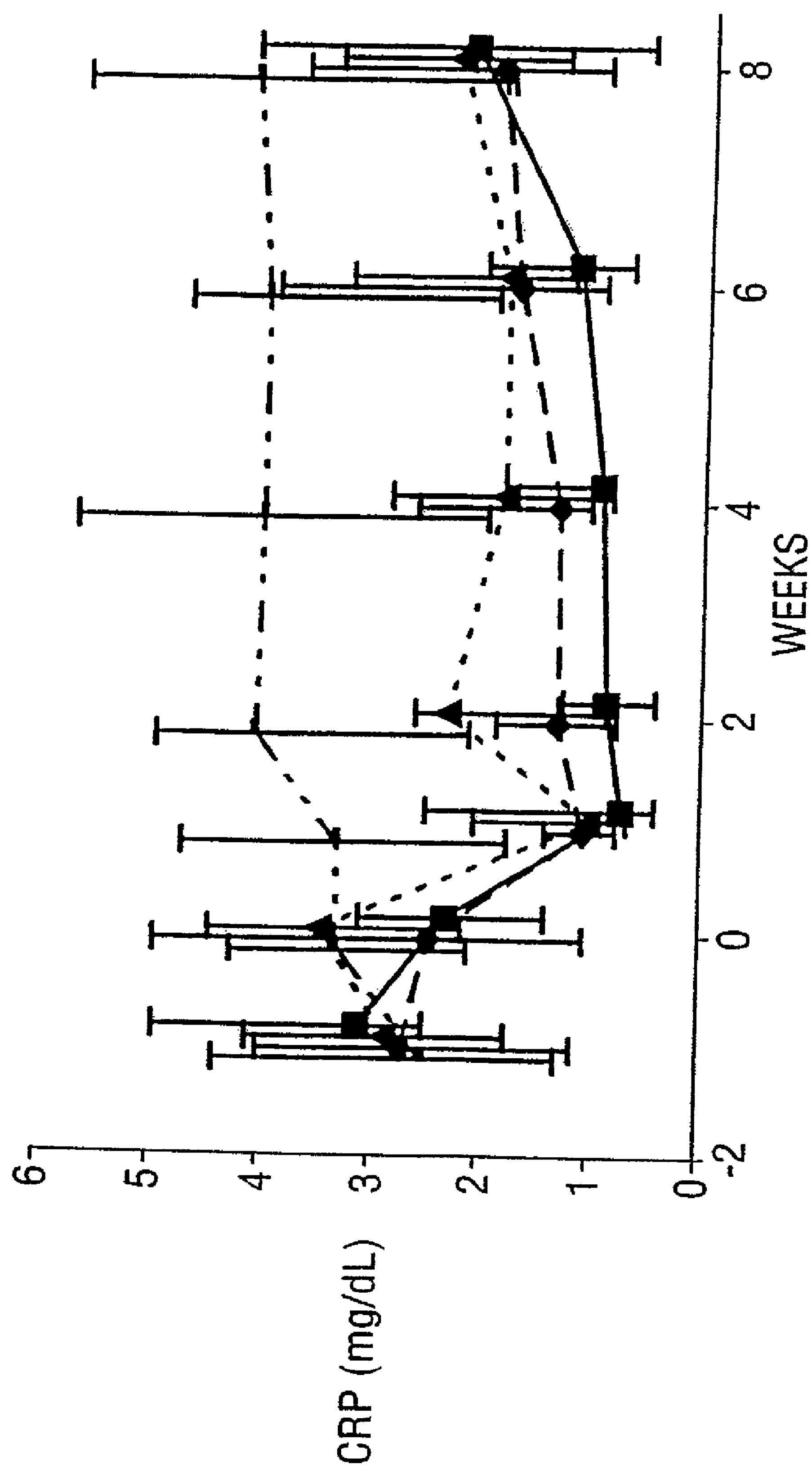
Figure 24C:
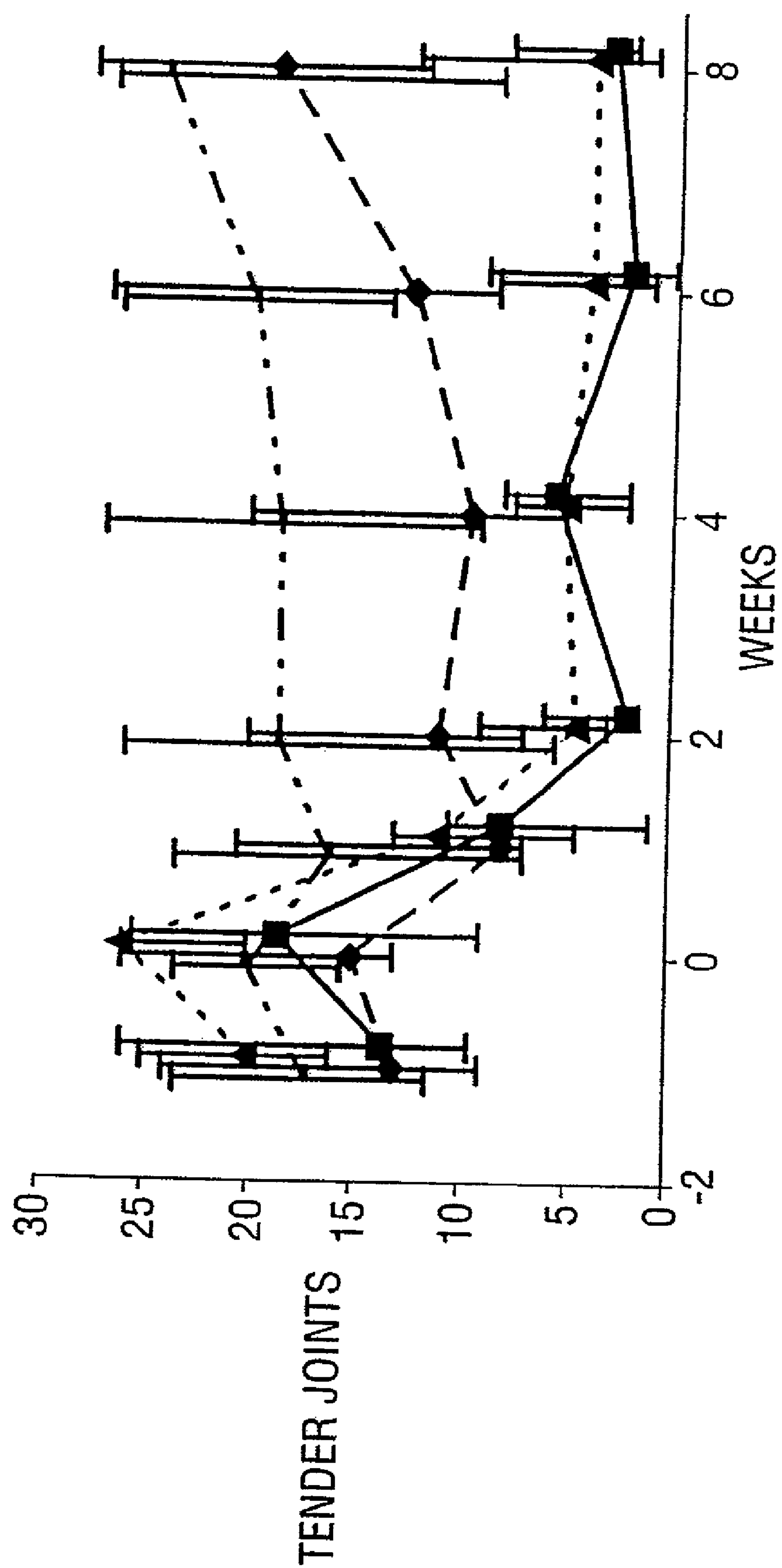
Figure 24D:
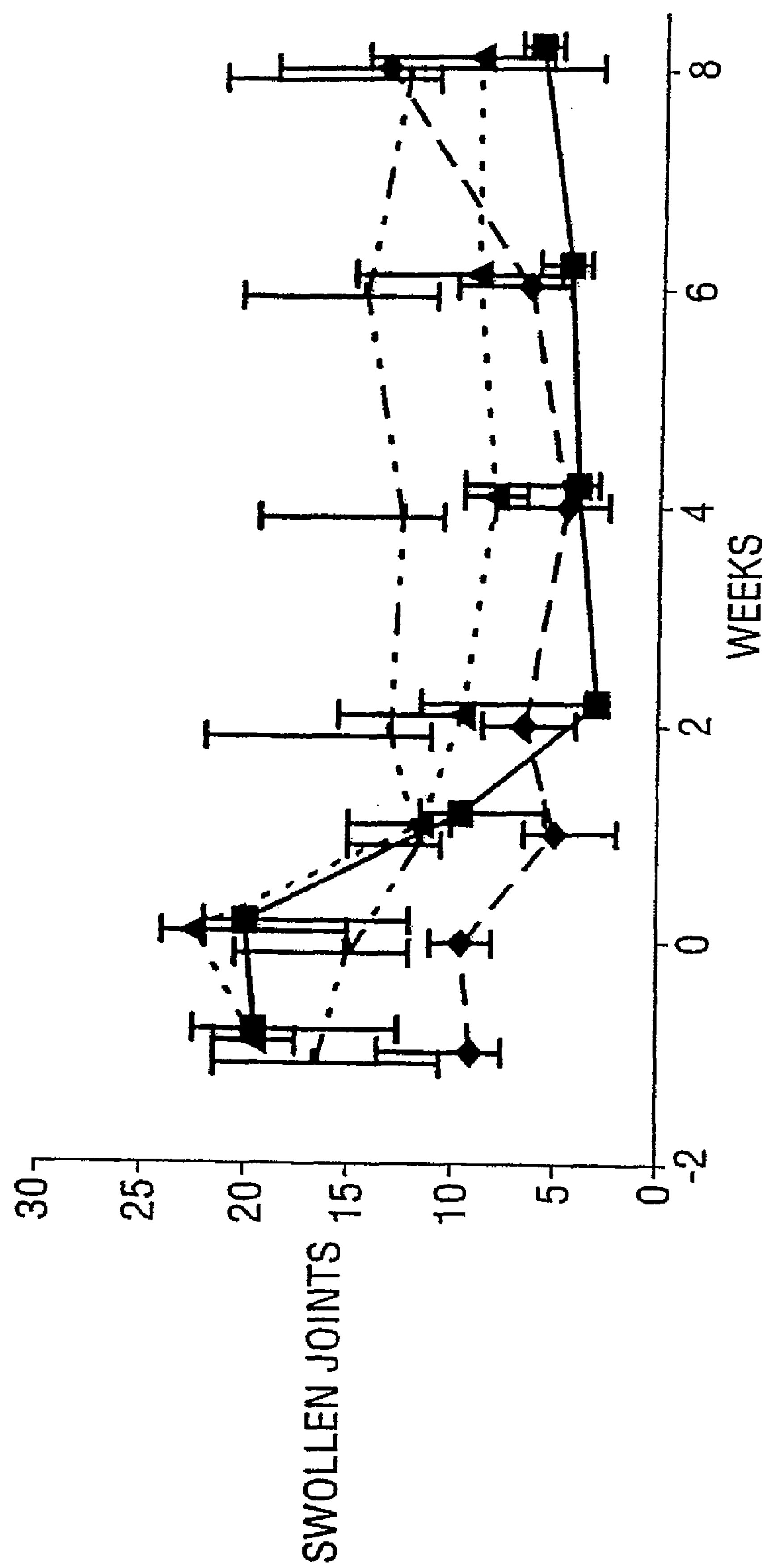
Figure 24E:
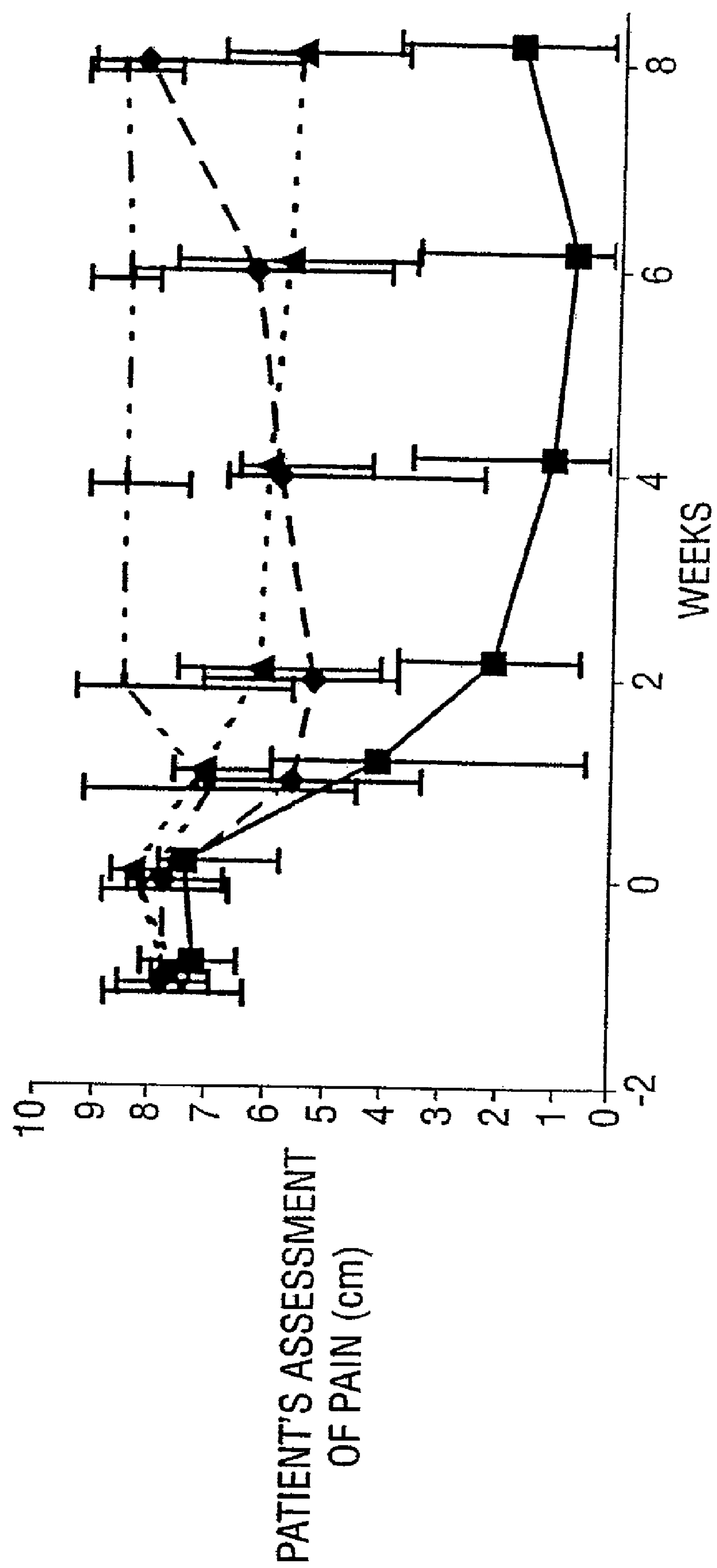
Figure 24F:
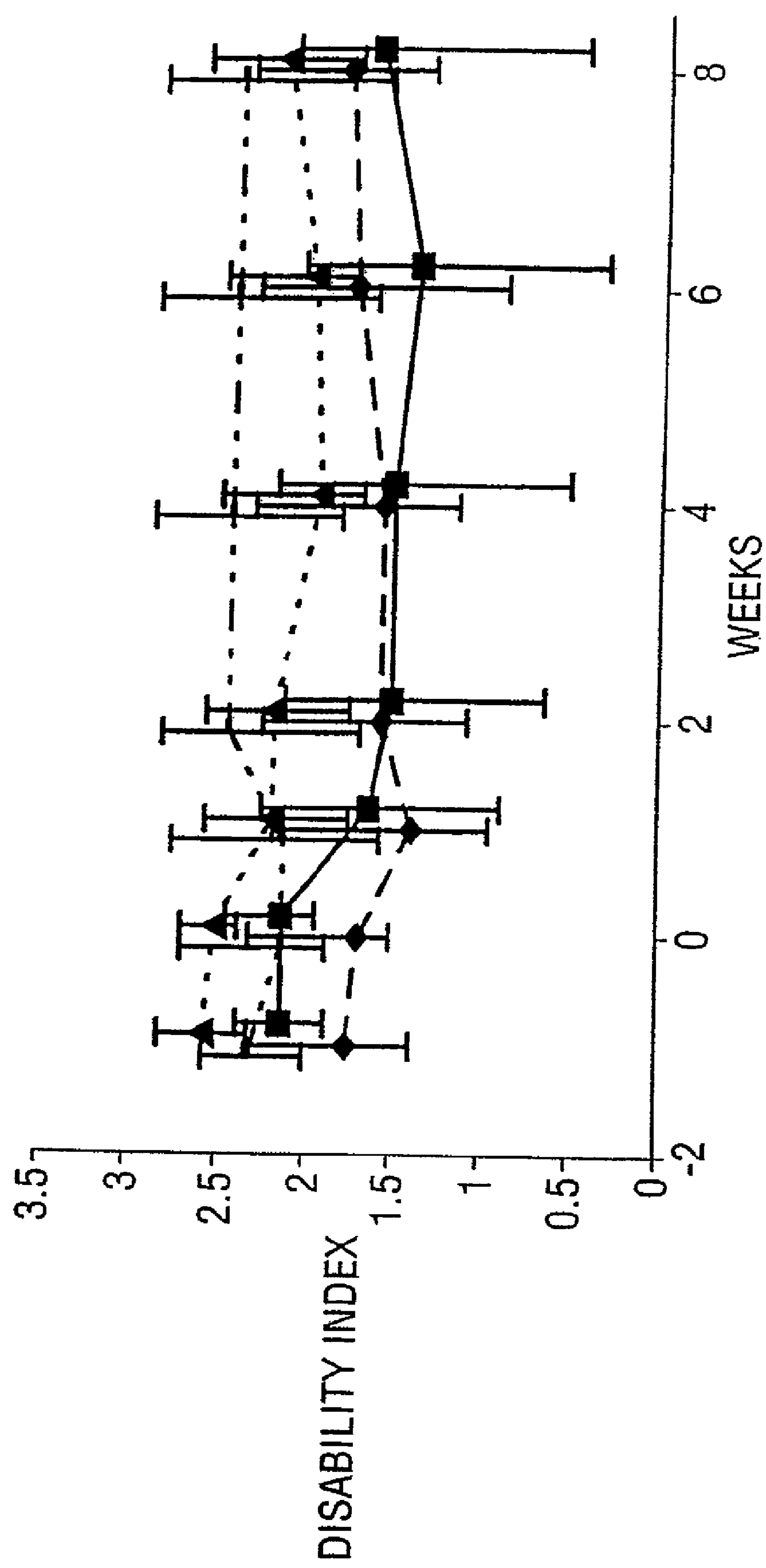
Figure 24G:
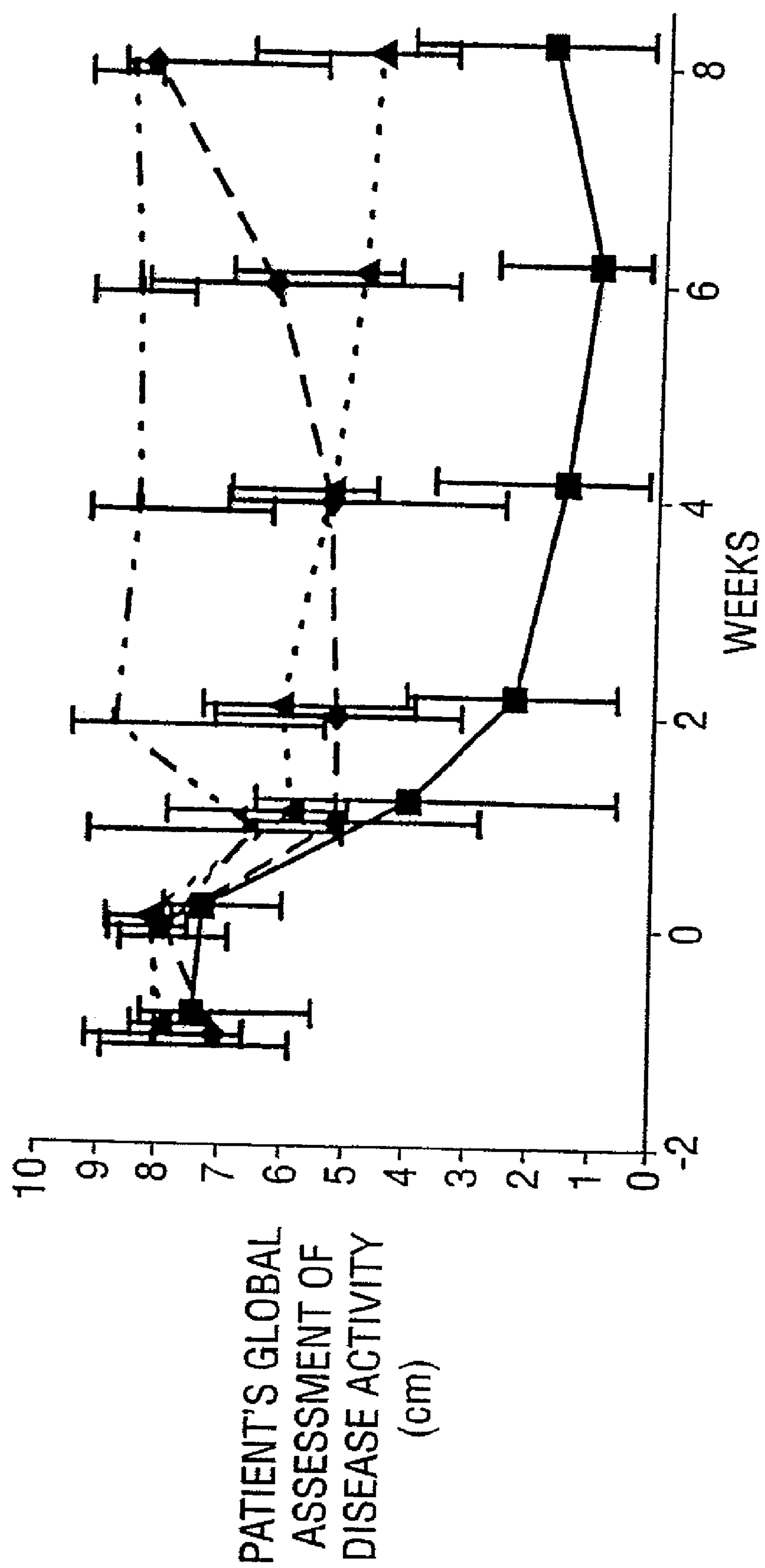
Figure 24H:
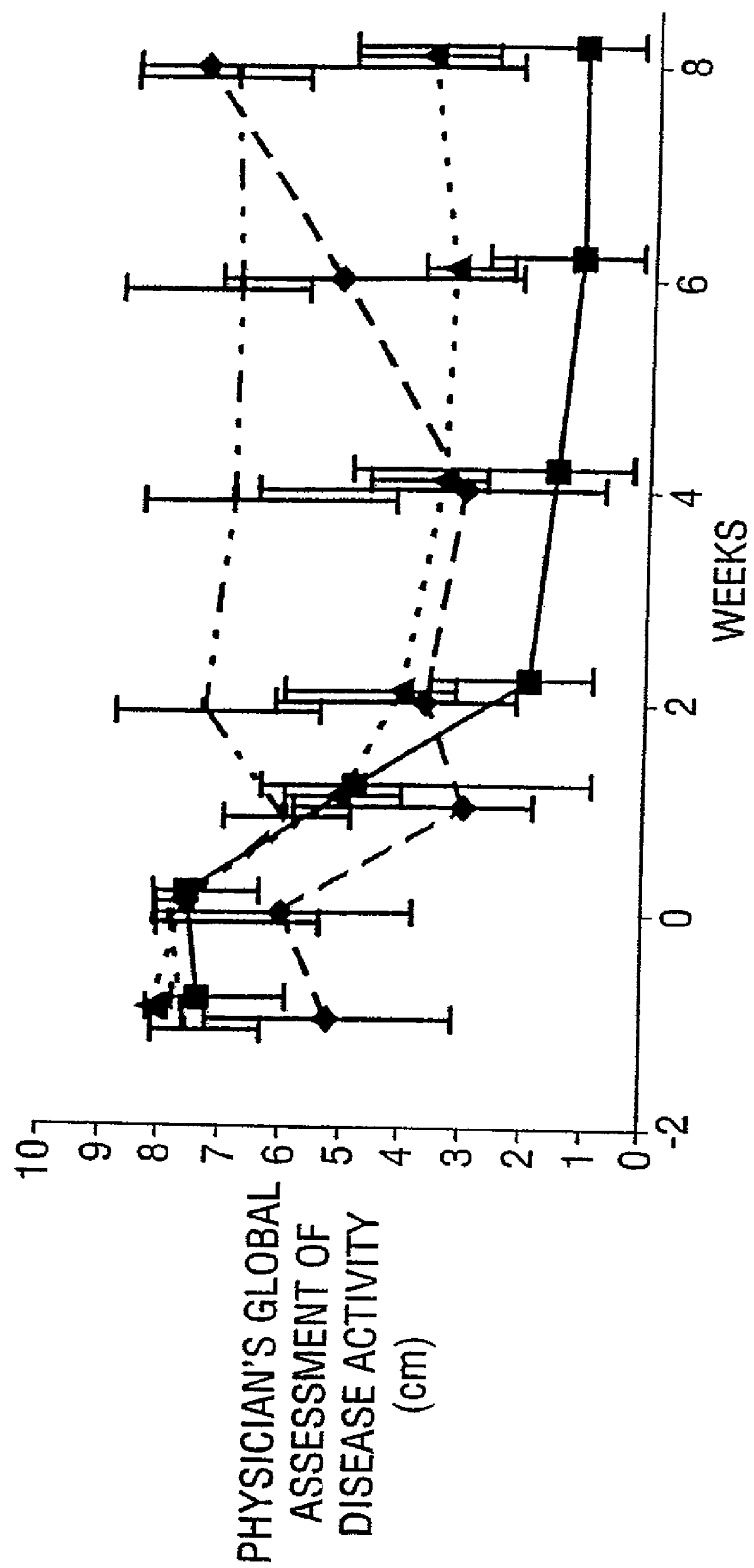

Clinical Efficacy:

The proportion of patients with ACR20 improvement for the per-protocol population with last observation carried forward was 16.7, 50, 87.5 and 62.5% after placebo, 1, 5 and 20 mg/kg CDP870 (combined treatment effect p=0.012) at 4 weeks and 16.7, 25, 75 and 75% (p=0.032) at 8 weeks. Reduction in DAS scores (median) for the per-protocol population with last observation carried forward was 0.15, 1.14, 1.91 and 1.95 after placebo, 1, 5 and 20 mg/kg CDP870 (combined treatment effect p=0.001) at 4 weeks and 0.31, 0.09, 2.09 and 1.76 (p=0.008) at 8 weeks (FIG. 23). Changes in individual components of the World Health Organization and International League of Associations for Rheumatology core data set are shown in FIG. 24.

Following the open label dose of CDP870, similar beneficial effects were achieved. Of the 36 patients recruited into the study, 32 received a second infusion of CDP870. The proportion of patients with ACR20 improvement from pre-first infusion was 72.2 and 55.6% after 5 and 20 mg/kg CDP870 at 4 weeks and 55.6 and 66.7% at 8 weeks.

Adverse Events

Treatment was well tolerated with no infusion-related reaction. No allergic reaction or skin rash was reported. In the double-blind phase, there were 19, 38, 8 and 14 adverse events in the placebo, 1, 5 and 20 mg/kg groups respectively. The commonest was headache with 9 episodes in 5 patients (1 placebo, 3 at 1 mg/kg, 1 at 20 mg/kg). One patient who received placebo and 3 patients who received CDP870 (1 at 5 mg/kg and 2 at 20 mg/kg) developed lower respiratory tract infections. These were reported as mild or moderate. They were treated with oral antibiotics and resolved over 1-2 week period. Three patients each in the 1 and 5 mg/kg groups and one in the 20 mg/kg group developed a urinary tract infection 1-2 months after CDP870 treatment. One adverse event was described as severe which was an episode of neck pain occurring 3 days after infusion with 1 mg/kg. Increase in anti-nuclear antibody was seen in 4 patients: 1 in the placebo group (negative to 1/40), 2 in the 1 mg/kg group (negative to 1/40, negative to 1/80) and 1 in the 20 mg/kg group (negative to 1/40). No change was found in anti-DNA or anti-cardiolipin antibodies.

CDP8 70 Plasma Concentration and Anti-CDP870 levels

As expected, for all dose levels of CDP870, the peak plasma concentration occurred at the end of infusion and was dose proportional with plasma concentration declining slowly thereafter. The plasma concentration profile of CDP870 appeared very similar to that previously observed in volunteers where the half-life was calculated to be approximately 14 days. On re-dosing, a similar profile to single dose infusion was observed.

Following a single intravenous infusion, anti-CDP870 levels were low or undetectable.

Discussion

Neutralizing TNFα is an effective treatment strategy in RA. Currently, this requires the use of biological agents, such as a chimeric mAb or a soluble receptor/human Fc fusion protein, which are expensive to manufacture. A therapeutic TNFα neutralizing agent needs to bind TNFα with high affinity and have a long plasma half-life, low antigenicity and high tolerability and safety. It also needs to be accessible to all patients with RA who would benefit from TNFα blockade. One technology that could achieve these objectives is the conjugation with polyethylene glycol of a TNFα binding antibody fragment made in *E. coli*. In this preliminary study, we find that CDP870, a PEGylated, anti-TNFα, modified Fab, is effective and well tolerated by patients with RA.

In vitro studies have shown that CDP870 has similar TNFα neutralizing activity to the murine anti-TNFα parent antibody. This study confirms that CDP870 reduced inflammation and improved symptoms in RA. Clinical improvement as measured by the ACR20 response criteria in the 5 and 20 mg/kg groups (75%, 75%) was comparable to etanercept (60%) (Moreland et al., Annals Int. Med., 130, 478-486, 1999) and infliximab (50%) (Maini et al., Lancet, 354, 1932-1939, 1999). At the middle and highest dosage levels tested, the therapeutic effect lasted 8 weeks which is comparable to previous other mAbs (Elliott et al., Lancet, 344, 1105-1110, 1994 and Rankin et al., Br. J. Rheumatol., 34, 334-342, 1995). Previous study has shown that the therapeutic effect of anti-TNFα antibody is related to its plasma half-life and the generation of circulating antibodies (Maini et al., Axthritis Rheum. 38, (Supplement): S186 1995 (Abstract)). Our study showed that CDP870 has a plasma half-life of 14 days which is equivalent to that of a whole antibody (Rankin et al., (supra)) and much longer than the half-life of unconjugated Fab' fragments. Further, CDP870 generated only very low levels of antibody response.

One of the important objectives of this study is to examine the tolerability and safety of administering this PEGylated Fab'. In our study, CDP870 appears well tolerated. Although further study will be needed to assess long term toxicity, especially the risk of demyelinating disease, infection and skin rashes that have been reported with etanercept and infliximab.

In summary, CDP870 is therapeutically effective in RA and was well tolerated in this short-term study.

The complete content of all publications, patents and patent applications cited in this description are herein incorporated by reference as if each individual publication, patent or patent application were specifically and individually indicated as being incorporated by reference.

The foregoing invention has been described above in some detail by way of illustration and example for the purposes of clarity of understanding. The above examples are provided for exemplification purposes only and are not intended to limit the scope of the invention, which has been described in broad terms before the examples. It will be readily apparent to one skilled in the art in light of the teachings of this invention that changes and modifications can be made without departing from the spirit and scope of the present invention.

What is claimed is:

1. An antibody molecule having specificity for human TNFα, comprising a) a heavy chain wherein the variable domain comprises
   (i) the sequence given in SEQ ID NO:1 for CDRH1,
   (ii) the sequence given in SEQ ID NO:2 or SEQ ID NO:7, for CDRH2, and
   (iii) the sequence given in SEQ ID NO:3 for CDRH3; and b) a light chain wherein the variable domain comprises
   (i) the sequence given in SEQ ID NO:4 for CDRL1,
   (ii) the sequence given in SEQ ID NO:5 for CDRL2, and
   (iii) the sequence given in SEQ ID NO:6 for CDRL3.

2. The antibody molecule of claim 1, which comprises SEQ ID NO:2 for CDRH2.

3. The antibody molecule of claim 1, which is a CDR-grafted antibody molecule.

4. The antibody molecule of claim 3, wherein the variable domains comprise human acceptor framework regions.

5. The antibody molecule of claim 4, wherein the human acceptor framework regions of the variable domain of the heavy chain are based on a human group 1 consensus sequence and comprise donor residues at positions 28, 69, and 71 according to Kabat numbering.

6. The antibody molecule of claim 4, wherein the human acceptor framework regions of the variable domain of the heavy chain are based on a human group 1 consensus sequence and comprise donor residues at positions 28, 38, 46, 67, 69, and 71 according to Kabat numbering.

7. The antibody molecule of claim 4, wherein the human acceptor framework regions of the variable domain of the heavy chain are based on a human group 3 consensus sequence and comprise donor residues at positions 27, 28, 30, 48 49, 69, 71, 73, 76, and 78 according to Kabat numbering.

8. The antibody molecule of claim 4, wherein the human acceptor framework regions of the variable domain of the light chain are based on human group 1 consensus sequence and comprise donor residues at positions 46 and 60 according to Kabat numbering.

9. The antibody molecule of claim 1, which is a Fab or Fab' fragment.

10. The antibody molecule of claim 1, which is a modified Fab' fragment, having at the C-terminal end of its heavy chain one or more amino acids to allow attachment of an effector or reporter molecule.

11. The antibody molecule of claim 10, wherein the additional amino acids form a modified hinge region containing one or two cysteine residues to which the effector or reporter molecule may be attached.

12. The antibody molecule of claim 10, having covalently attached to an amino acid at or towards the C-terminal end of its heavy chain an effector or reporter molecule.

13. The antibody molecule of claim 12, which comprises an effector molecule.

14. The antibody molecule of claim 13, wherein the effector molecule comprises one or more polymers.

15. The antibody molecule of claim 14, wherein the one or more polymers is/are an optionally substituted straight or branched chain polyalkylene, polyalkenylene or polyoxyalkylene polymer or a branched or unbranched polysaccharide.

16. The antibody molecule of claim 11, wherein a maleimide group is covalently linked to a single thiol group in the modified hinge region.

17. The antibody molecule of claim 16, wherein a lysine is covalently linked to the maleimide group.

18. The antibody molecule of claim 17, wherein a methoxypoly(ethyleneglycol) polymer having a molecular weight of about 20000 Da is attached to each of the amine groups of the lysine.

19. The antibody molecule of claim 15, wherein the polymer has an average molecular weight of about 500 to 50000 Da.

20. The antibody molecule of claim 19, wherein the polymer has an average molecular weight of about 25000 to 40000 Da.

21. The antibody molecule of claim 15, wherein the polymer is methoxypoly(ethyleneglycol) with a molecular weight of about 25000 to 40000 Da.

22. The antibody according to claim 21, which has the formula:

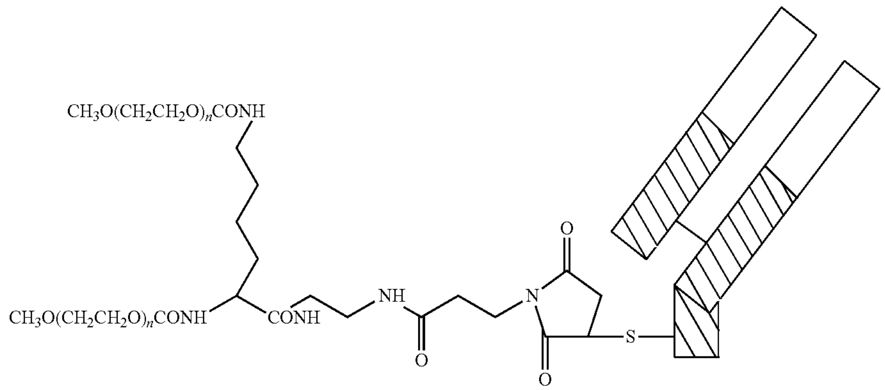

wherein n is about 420.

* * * * *